United States Patent
Koon et al.

(10) Patent No.: US 9,772,334 B2
(45) Date of Patent: Sep. 26, 2017

(54) INFLAMMATORY BOWEL DISEASE MARKERS AND THERAPIES FOR COLITIS-ASSOCIATED INTESTINAL FIBROSIS

(71) Applicant: THE REGENTS OF THE UNIVERSITY OF CALIFORNIA, Oakland, CA (US)

(72) Inventors: Hon Wai Koon, Los Angeles, CA (US); Charalabos Pothoulakis, Los Angeles, CA (US); Avinoam Dukler, Newbury Park, CA (US)

(73) Assignees: THE REGENTS OF THE UNIVERSITY OF CALIFORNIA, Oakland, CA (US); Avinoam Dukler, Newbury Park, CA (US)

( * ) Notice: Subject to any disclaimer, the term of this patent is extended or adjusted under 35 U.S.C. 154(b) by 0 days.

(21) Appl. No.: 14/743,909

(22) Filed: Jun. 18, 2015

(65) Prior Publication Data
US 2016/0161501 A1   Jun. 9, 2016

Related U.S. Application Data

(63) Continuation-in-part of application No. 14/648,207, filed as application No. PCT/US2013/074034 on Dec. 10, 2013, now Pat. No. 9,651,562.

(60) Provisional application No. 61/735,372, filed on Dec. 10, 2012.

(51) Int. Cl.
*A61K 38/00* (2006.01)
*G01N 33/68* (2006.01)

(52) U.S. Cl.
CPC . *G01N 33/6893* (2013.01); *G01N 2333/4721* (2013.01); *G01N 2333/4737* (2013.01); *G01N 2800/065* (2013.01)

(58) Field of Classification Search
None
See application file for complete search history.

(56) References Cited

U.S. PATENT DOCUMENTS

| 8,043,821 | B2 * | 10/2011 | Boga | G01N 33/54306 435/7.1 |
| 8,202,835 | B2 | 6/2012 | Hillman | |
| 2003/0171251 | A1 * | 9/2003 | Pepys | A61K 31/00 514/1 |
| 2009/0048167 | A1 * | 2/2009 | Hillman | A61K 38/1729 514/2.4 |

FOREIGN PATENT DOCUMENTS

WO   WO2010139195 A1   12/2010

OTHER PUBLICATIONS

Vermiere et al. C-Reactive Protein as a Marker for Inflammatory Bowel Disease, Inflamm. Bowel Dis. vol. 10, No. 5, Sep. 2004; p. 661, col. 1.*
Guani-Guerra et al., "Ant imi crobi al peptides: general overview and clinical implications in human health and disease", Clinical Immunology, vol. 135, No. 1, pp. 1-11 (2010).
Nijnik et al., "The roles of cathelicidin LL-37 in immune defences and novel clinical applications", Current Opinion in Hematology, vol. 16, No. 1, pp. 41-47 (2009).
Otte et al., "Role of antimicrobial peptides in inflammatory bowel disease", Polymers, vol. 3, No. 4, pp. 2010-2017 (2011).
International Search Report and Written Option dated Mar. 13, 2014 from corresponding International Application PCT/US2013/074034 filed Dec. 10, 2013 (WO2014/093297).

* cited by examiner

*Primary Examiner* — Jeanette Lieb
(74) *Attorney, Agent, or Firm* — Karen S. Canady; canady + lortz LLP

(57) ABSTRACT

Method of diagnosing and treating inflammatory bowel disease are disclosed herein. Inflammatory bowel disease can be treated and diagnosed using cathelicidin peptides and detection agents thereof. Specifically, method of treating and diagnosing Crohn's disease and ulcerative colitis are disclosed herein.

13 Claims, 43 Drawing Sheets

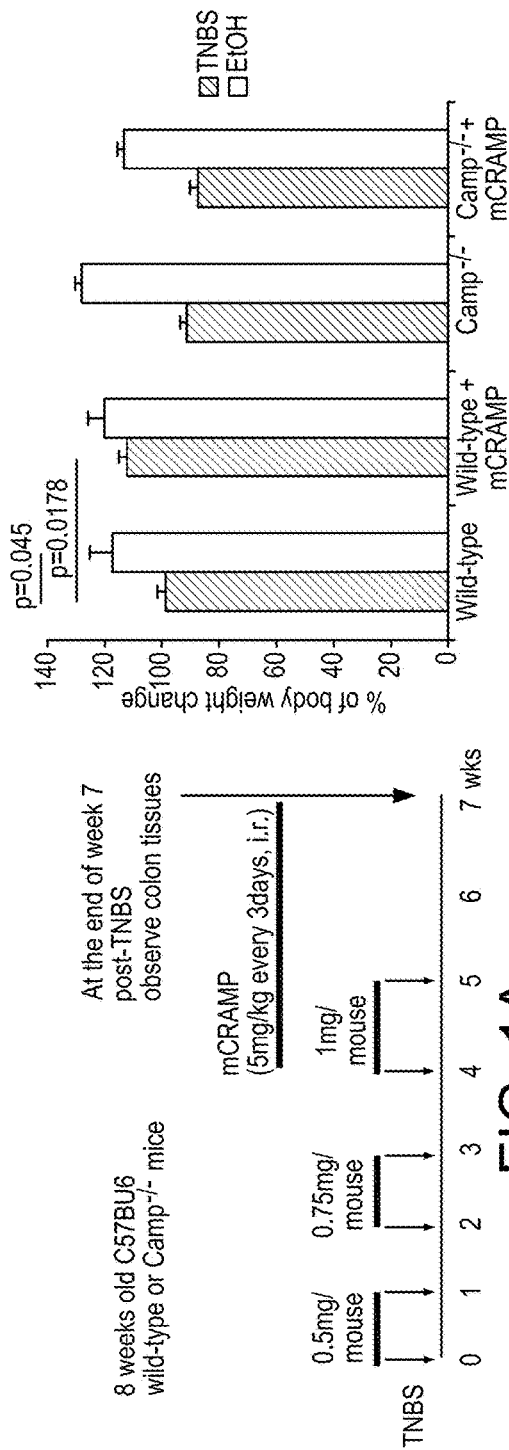
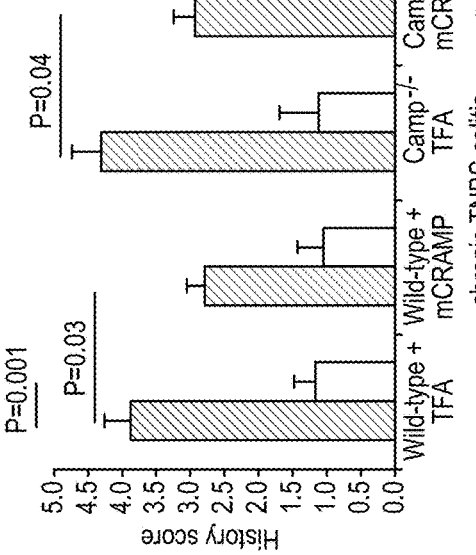
FIG. 1A
FIG. 1B
FIG. 1D

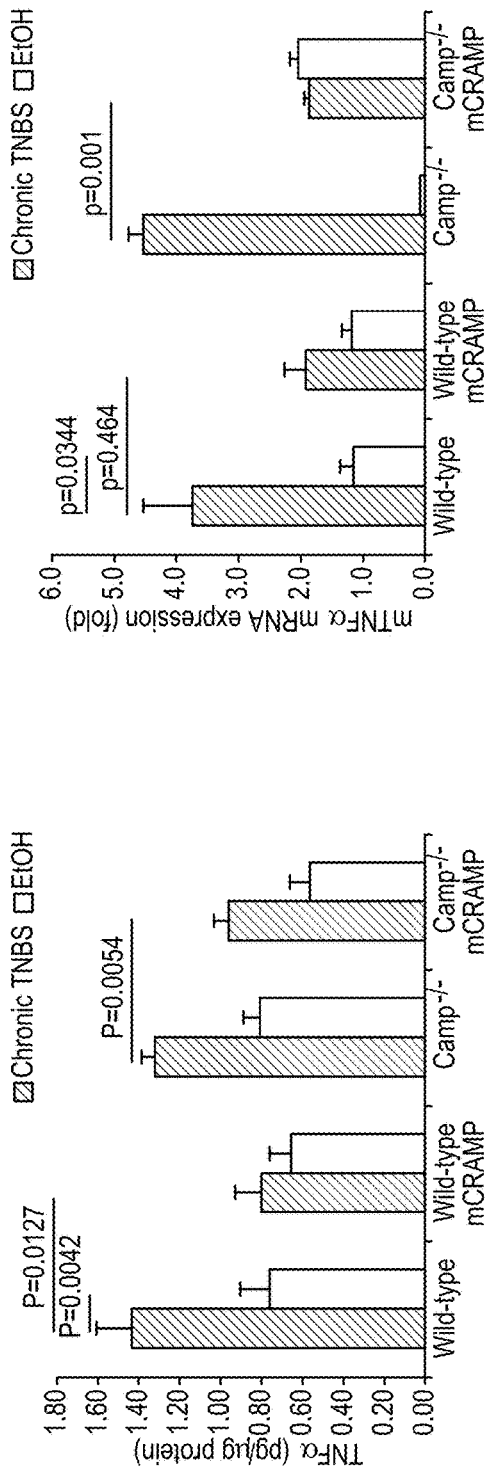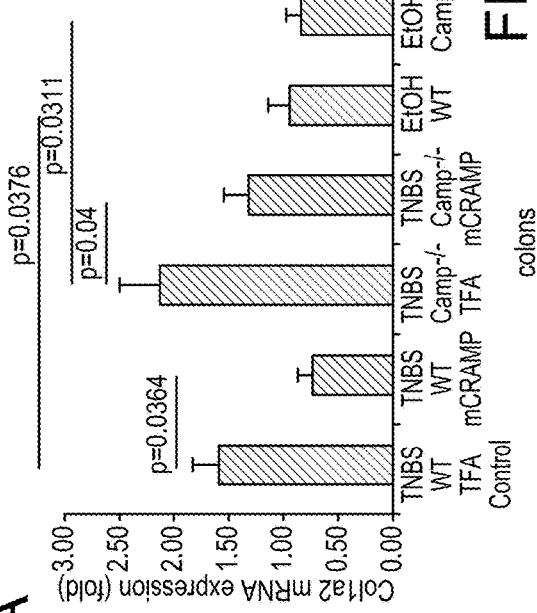
FIG. 2A  FIG. 2B  FIG. 2D

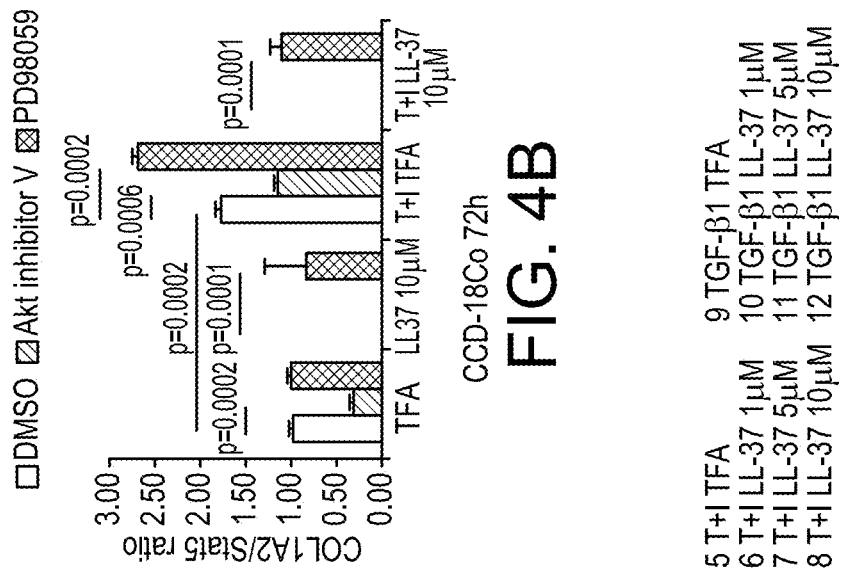
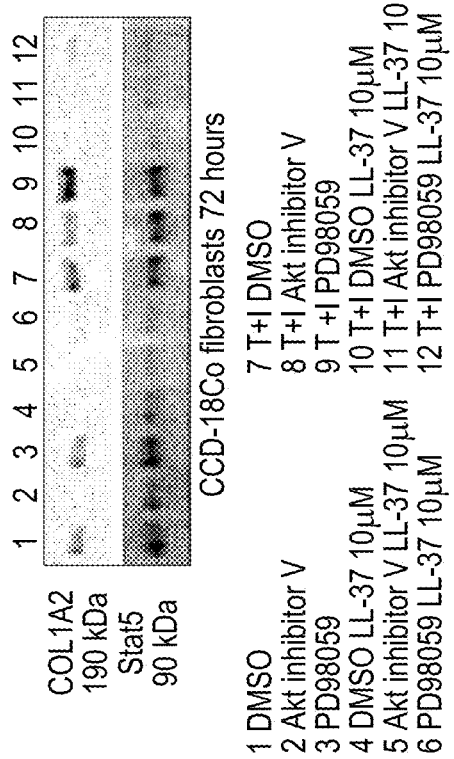
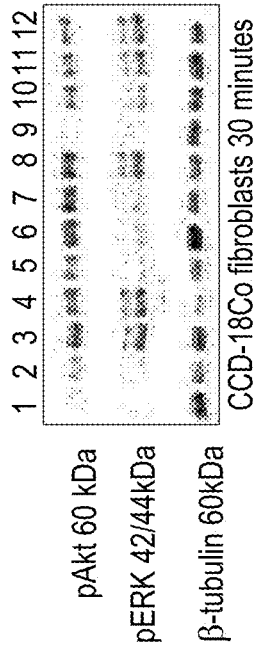
FIG. 4A
FIG. 4B
FIG. 4C

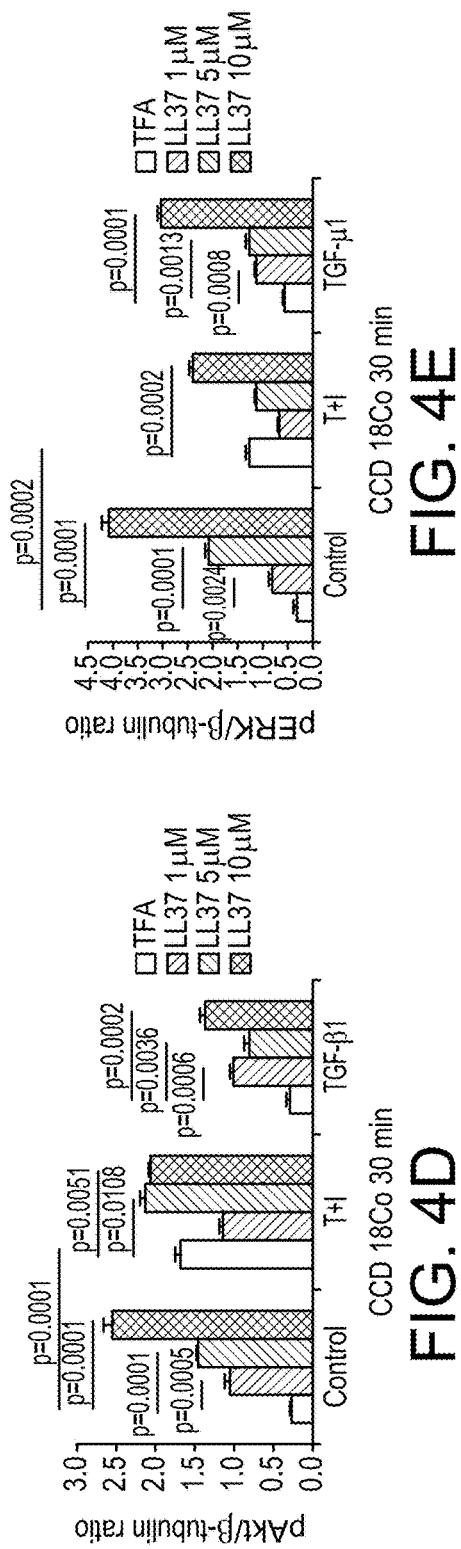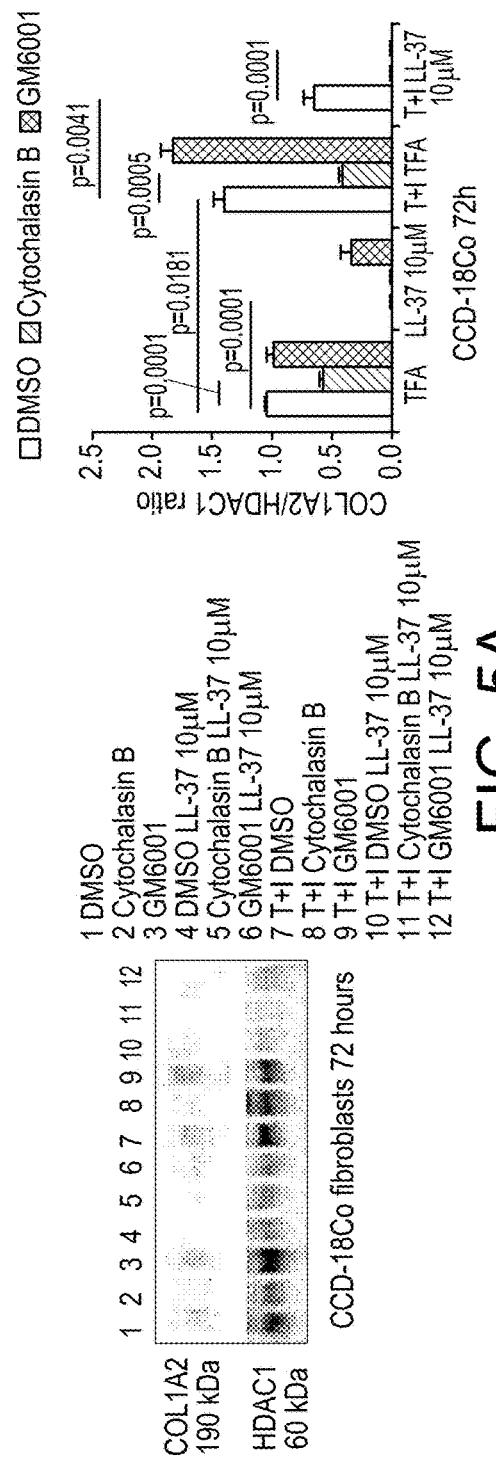
FIG. 4D
FIG. 4E
FIG. 5A

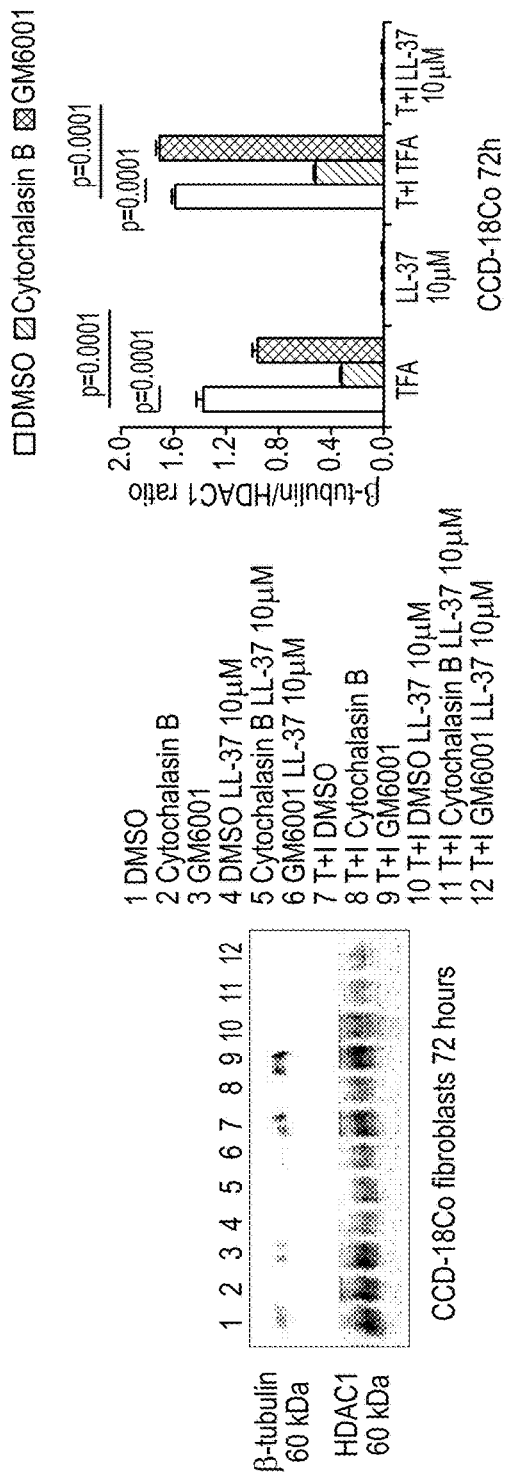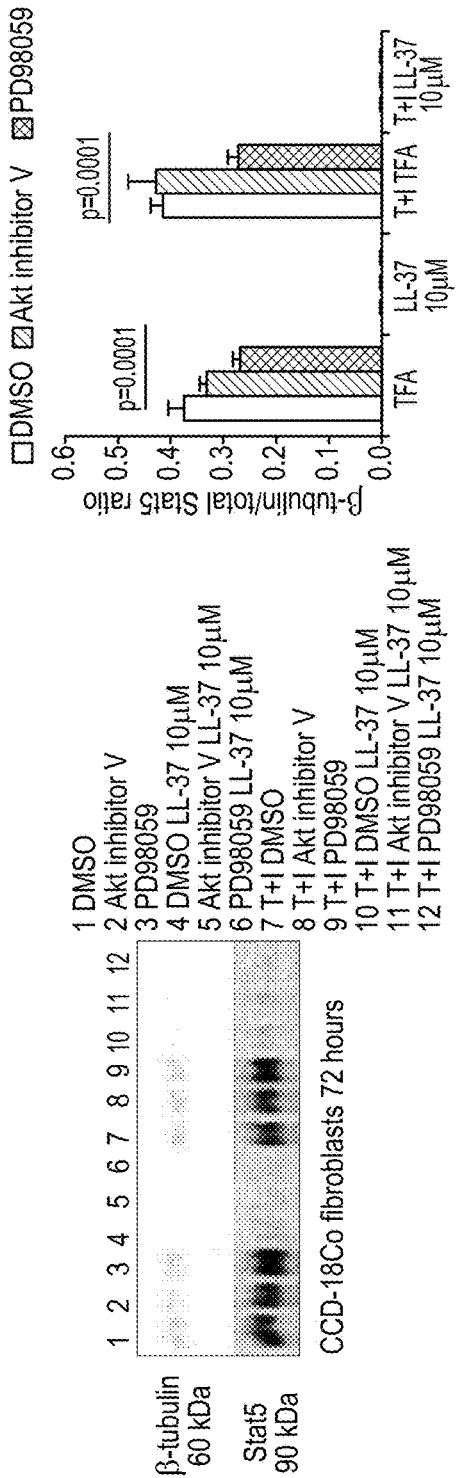

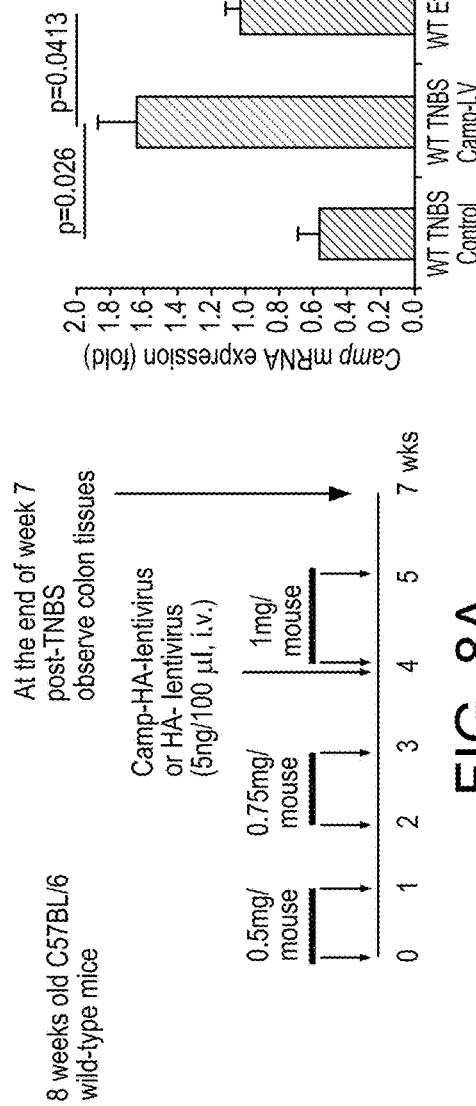
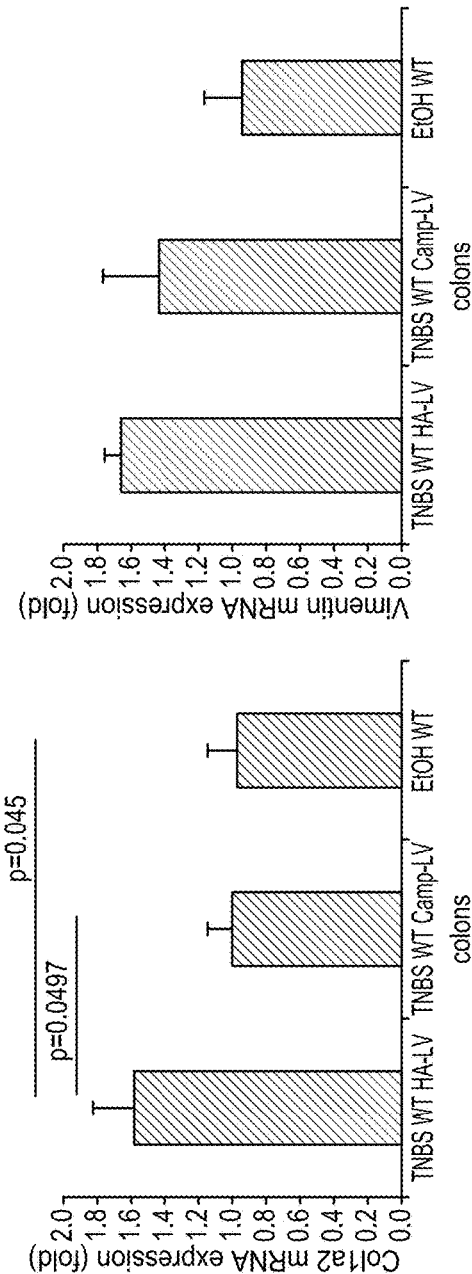
FIG. 8A, FIG. 8B, FIG. 8C, FIG. 8D

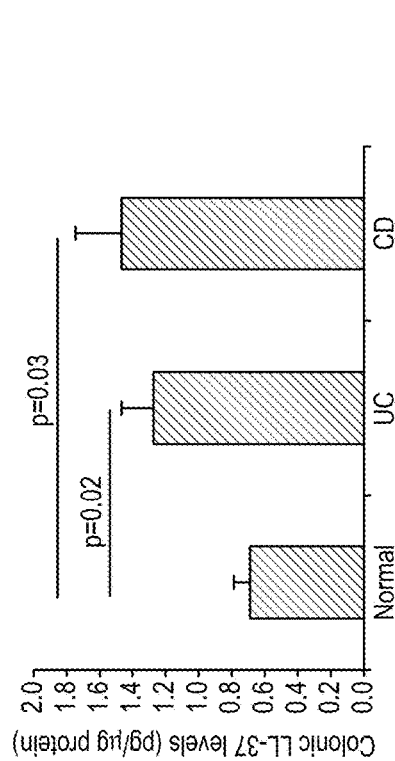
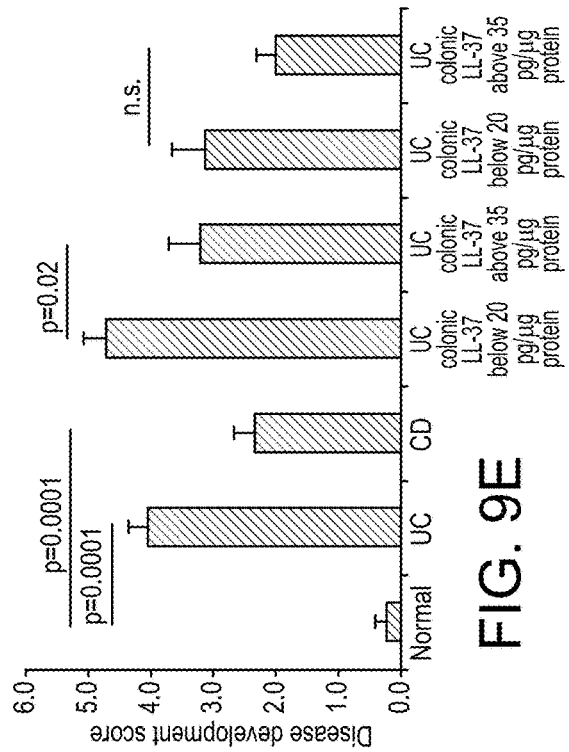
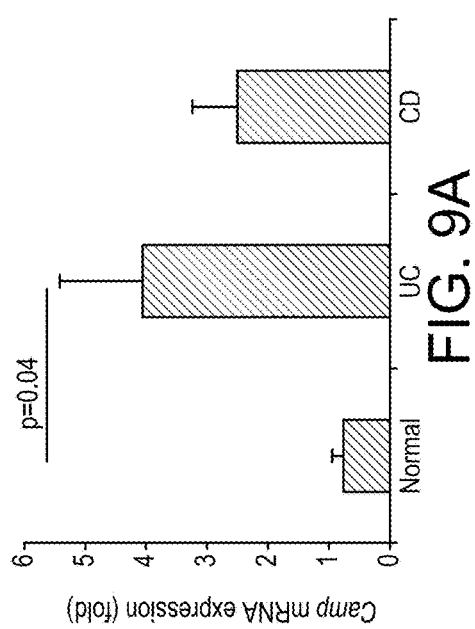

Disease development score is the sum of the following 5 categories

Disease free period 0-2 points
0= disease free for 2 years
1 = first year disease free
2= first 6 months disease free

Count of IBD related surgery in the last 2 years 0-3 points

Count of hospitalization since surgery (within 2 years after surgery): 0-1 point

WBC count ($10^9$ cells per liter): 0-2 points
3-5 leukopenia = +1
5-10 = normal = 0
11-17 = leukocytosis = +1

Anemia score (grams hemoglobin per deciliter): 0-2 points
normal male 14-18 grams/dl
normal female 12-16 grams/dl normal= 0
10-12 or 10-14 mild = 1
below 10 = severe = 2

FIG. 9A  FIG. 9B  FIG. 9D  FIG. 9E

Baseline characteristics (All groups)

| | All normal patients | | All Ulcerative Colitis | | All Crohn's Disease | | Statistical significance |
|---|---|---|---|---|---|---|---|
| | mean | sem | mean | sem | mean | sem | |
| Age of patients (2012) | 72.0 | 4.5 | 44.7 | 2.8 | 41.1 | 3.1 | n.s. UC vs. CD |
| Age of diagnosis | insufficient data | | 29.8 | 2.8 | 24.1 | 2.1 | n.s. UC vs. CD |
| Age of surgery | 70.0 | 4.5 | 42.7 | 2.9 | 37.3 | 3.3 | n.s. UC vs. CD |
| BMI | 21.1 | 0.8 | 22.7 | 0.7 | 23.8 | 1.0 | |
| Sex (male) | insufficient data | | 60% | | 60% | | n.s. among all groups |
| %of current anti-TNFα treatment | no data | | 21% | | 44% | | |
| % of current 6-MP or steroid treatment | no data | | 50% | | 44% | | |
| Histology score | 1.8 | 0.2 | 8.0 | 0.6 | 8.7 | 0.6 | p=0.0001 UC vs. Nor<br>p=0.0001 CD vs. Nor |
| C-reactive protein (mg/L) | no data | | 3.2 | 0.9 | 2.2 | 0.9 | |
| Erythrocyte sedimentation rate (mm/h) | no data | | 23.7 | 5.4 | 25.9 | 4.4 | |
| n | 17 | | 24 | | 24 | | |

FIG. 10A

Inclusion criteria:
Cedars Sinai Medical Center IBD patients
Male or female above age 18
Active UC involving colons
Active CD involving ileum
Able to make informed consent independently

Exclusion criteria:
No pregnant women
No prisoners
No patients under age 18

Baseline characteristics (UC groups)

| | UC colonic LL-37 below 20 pg/µg protein | | UC colonic LL-37 above 35 pg/µg protein | | Statistical significance |
|---|---|---|---|---|---|
| | mean | sem | mean | sem | |
| Age of patients (2012) | 46.5 | 3.8 | 42.3 | 4.4 | n.s. |
| Age of diagnosis | 28.2 | 3.9 | 32.0 | 4.2 | n.s. |
| Age of surgery | 44.9 | 4.1 | 40.0 | 4.4 | n.s. |
| BMI | 23.9 | 0.9 | 21.2 | 0.9 | n.s. |
| Sex (male) | 7 out of 13 | | 6 out of 10 | | |
| Smoking | 3 out of 13 | | 3 out of 10 | | |
| Colonic protein levels in the surgery biopsies (pg/µg protein) | | | | | |
| average LL-37 level | 11.80 | 1.80 | 59.30 | 6.60 | p=0.0001 |
| average TNFα level | 0.39 | 0.16 | 0.58 | 0.22 | n.s. |
| % of current anti-TNFα treatment | 10% | | 15% | | |
| % of current 6-MP or steroid treatment | 50% | | 50% | | |
| C-reactive protein (mg/L) | 4.3 | 1.4 | 1.3 | 0.3 | n.s. |
| Erythrocyte sedimentation rate (mm/h) | 27.3 | 8.1 | 16.4 | 4.9 | n.s. |
| Histology score | 7.9 | 1.0 | 8.4 | 1.2 | n.s. |
| n | 13 | | 10 | | |

FIG. 11A

Baseline characteristics (CD groups)

| | CD colonic LL-37 below 20 pg/µg protein | | CD colonic LL-37 above 35 pg/µg protein | | Statistical significance |
|---|---|---|---|---|---|
| | mean | sem | mean | sem | |
| Age of patients (2012) | 44.0 | 3.6 | 34.0 | 5.5 | n.s. |
| Age of diagnosis | 26.1 | 3.5 | 20.1 | 2.3 | n.s. |
| Age of surgery | 38.5 | 4.5 | 32.0 | 5.5 | n.s. |
| BMI | 23.0 | 1.0 | 25.0 | 2.5 | n.s. |
| Sex (male) | 8 out of 12 | | 4 out of 7 | | |
| Smoking | 0 out of 12 | | 2 out of 7 | | |
| Colonic protein levels in the surgery biopsies (pg/µg protein) | | | | | |
| average LL-37 level | 12.20 | 1.60 | 72.20 | 10.30 | $p=0.0001$ |
| average TNFα level | 0.20 | 0.04 | 0.30 | 0.06 | n.s. |
| % of current anti-TNFα treatment | 33% | | 50% | | |
| % of current 6-MP or steroid treatment | 44% | | 50% | | |
| C-reactive protein (mg/L) | 3.4 | 1.6 | 0.8 | 0.3 | n.s. |
| Erythrocyte sedimentation rate (mm/h) | 32.6 | 7.2 | 16.3 | 5.0 | n.s. |
| Histology score | 8.8 | 0.8 | 8.2 | 1.0 | n.s. |
| n | 12 | | 7 | | |

FIG. 11B

Inclusion criteria:

Cedars Sinai Medical Center IBD patients
Male or female above age 18
Active UC involving colons
Active CD involving ileum
Able to make informed consent independently

Exclusion criteria:

No pregnant women
No prisoners
No patients under age 18

FIG. 12A

| Baseline Characteristics | Normal mean | sem | UC mean | sem | CD mean | sem |
|---|---|---|---|---|---|---|
| Histology score | 2.6 | 0.3 | 7.5 | 0.4 | 8.4 | 0.4 |
| age | 66.3 | 1.9 | 44.9 | 1.9 | 42.6 | 2.0 |
| age of diagnosis | no data | | 30.9 | 1.8 | 26.5 | 1.5 |
| age of surgery | no data | | 42.3 | 2.0 | 39.3 | 2.1 |
| male sex % | 90 | | 60.0 | | 70.0 | |
| BMI | 24.9 | 0.5 | 22.9 | 0.5 | 24.2 | 0.7 |
| % of anti-TNF treatment | no data | | 23.0 | | 33.0 | |
| % of steroid treatment | no data | | 51.0 | | 53.0 | |
| n | 41 | | 52 | | 52 | |

FIG. 12B

| Baseline Characteristics | UC mean | sem | CD mean | sem | UC intestinal LL-37 below 20pg/µg protein mean | sem | UC intestinal LL-37 above 35pg/µg protein mean | sem | CD intestinal LL-37 below 20pg/µg protein mean | sem | CD intestinal LL-37 above 35pg/µg protein mean | sem |
|---|---|---|---|---|---|---|---|---|---|---|---|---|
| Histology score | 7.5 | 0.4 | 8.4 | 0.4 | 7.3 | 0.7 | 8.1 | 0.9 | 8.3 | 0.6 | 8.2 | 0.8 |
| age | 44.9 | 1.9 | 42.6 | 2.0 | 47.6 | 3.5 | 39.1 | 3.3 | 45.3 | 2.9 | 34.8 | 3.6 |
| age of diagnosis | 30.9 | 1.8 | 26.5 | 1.5 | 31.4 | 3.1 | 39.5 | 2.2 | 28.3 | 2.8 | 23.1 | 2.8 |
| age of surgery | 42.3 | 2.0 | 39.3 | 2.1 | 46.8 | 3.5 | 36.6 | 3.4 | 40.8 | 3.4 | 32.8 | 3.7 |
| male sex % | 60.0 | | 70.0 | | 38.0 | | 58.0 | | 68.0 | | 73.0 | |
| BMI | 22.9 | 0.5 | 24.2 | 0.7 | 23.2 | 0.9 | 22.7 | 1.2 | 24.3 | 1.0 | 26.1 | 1.7 |
| % of anti-TNF treatment | 23.0 | | 33.0 | | 6.0 | | 23.0 | | 26.0 | | 50.0 | |
| % of steroid treatment | 51.0 | | 53.0 | | 53.0 | | 46.0 | | 47.0 | | 58.0 | |
| n | 52 | | 52 | | 17 | | 13 | | 20 | | 13 | |

FIG. 13A

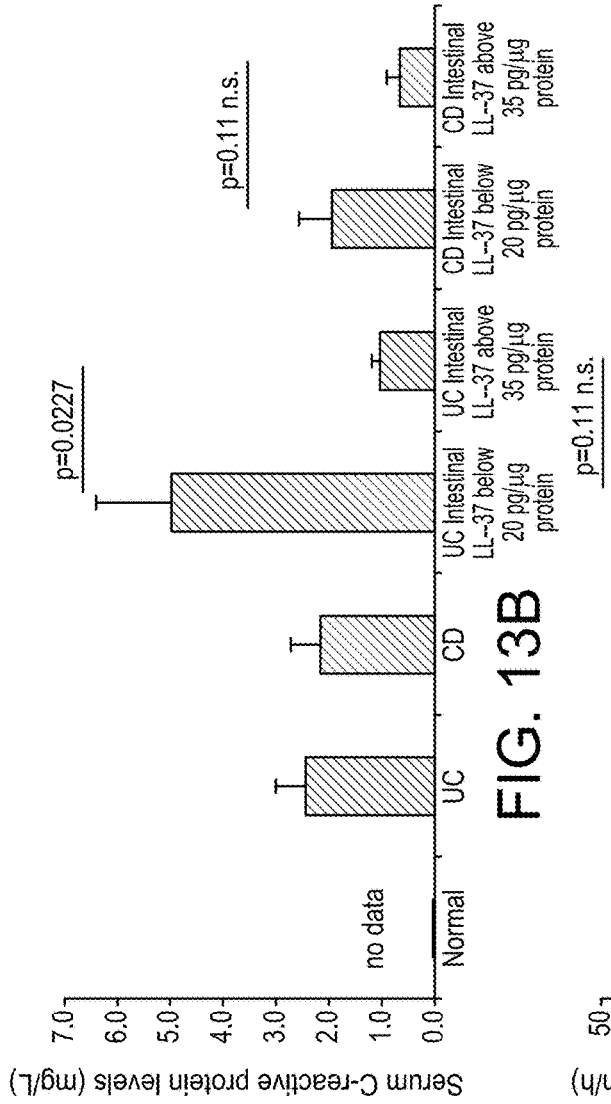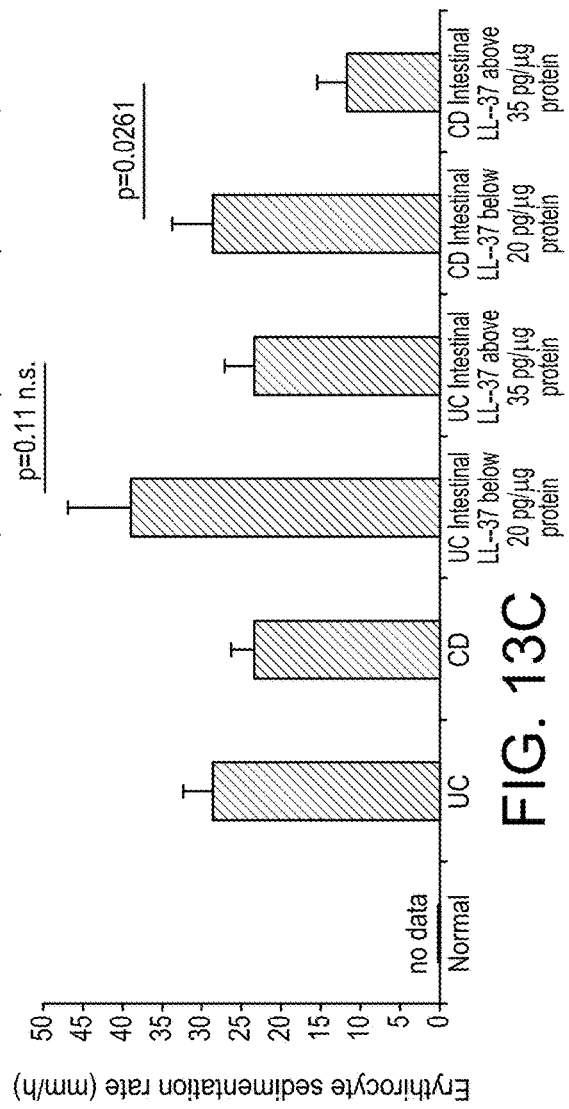

A

Inclusion criteria:

UCLA Ronald Reagan Medical Center
Healthy Normal and IBD patients
Male or female above age 18
Able to make informed consent independently Exclusion criteria:

No pregnant women
No prisoners
No patients under age 18

B

Baseline characteristics of blood samples

C

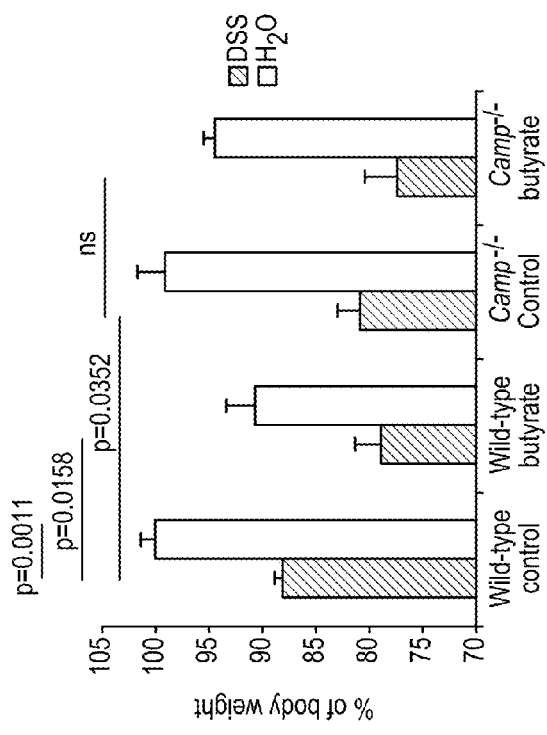
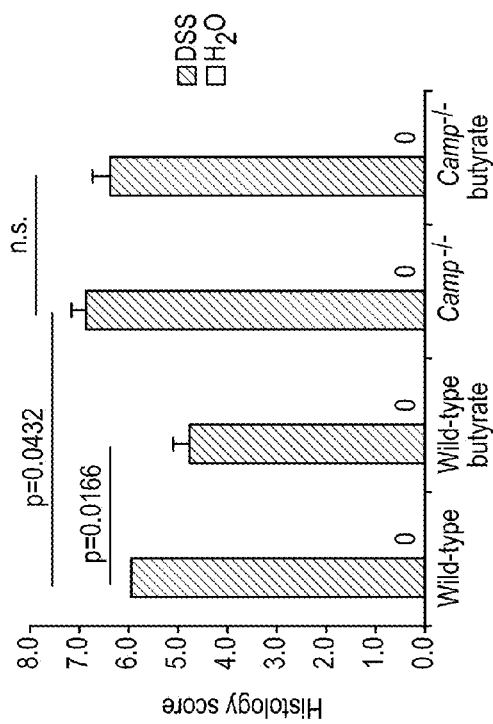
FIG. 15A
FIG. 15B
FIG. 15D

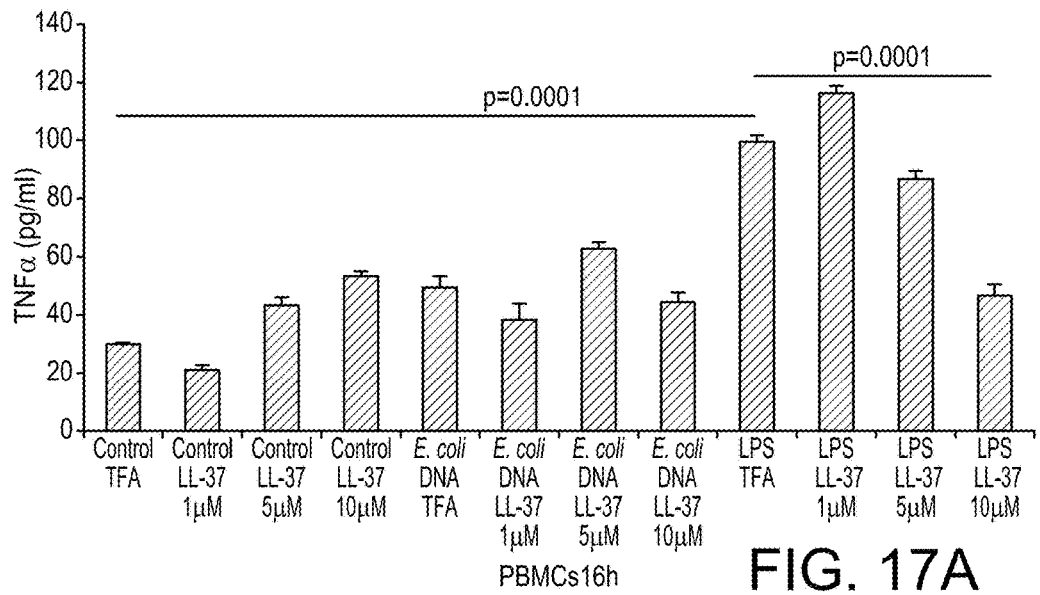
FIG. 17A
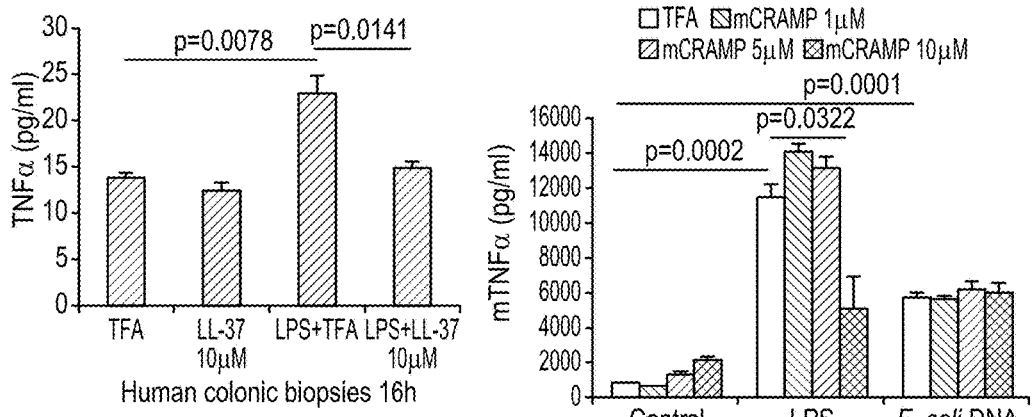
FIG. 17B
FIG. 17C
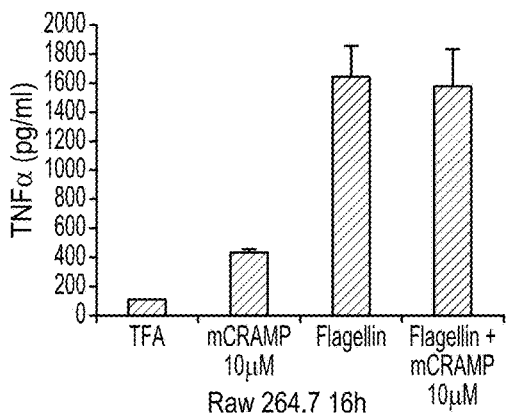
FIG. 17D
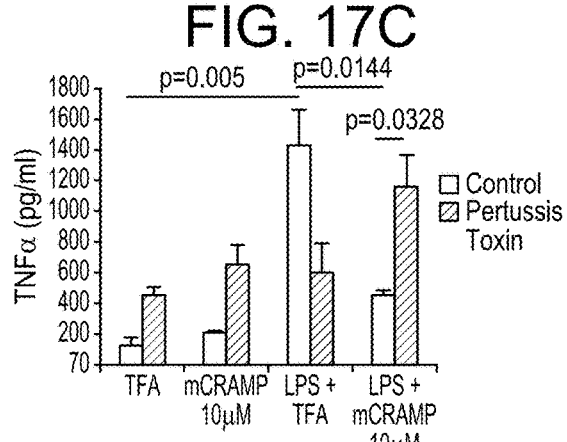
FIG. 17E

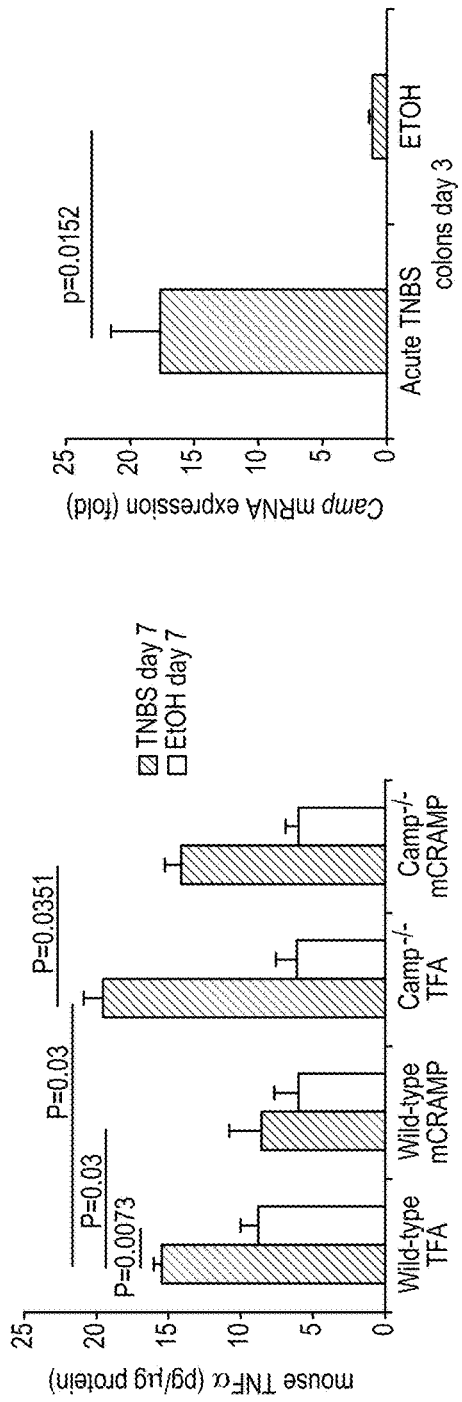
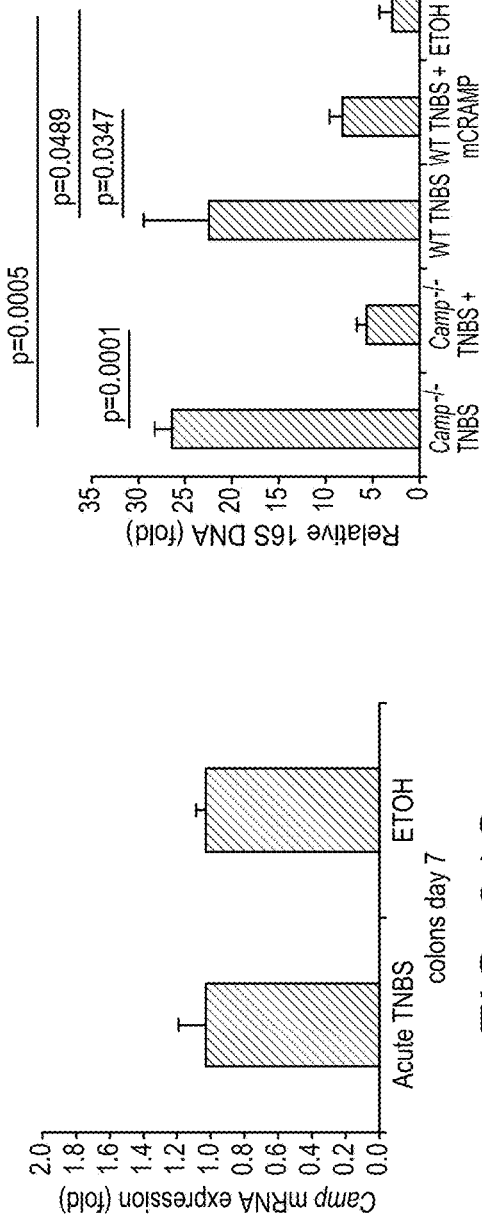
FIG. 21A
FIG. 21B
FIG. 21C
FIG. 21D

A

B

| Use low LL-37 to indicate presence of stricture | CD without stricture | CD with stricture | totals |
|---|---|---|---|
| Test postive (LL-37 <45) | 15 | 7 | 22 |
| Test negative (LL-37 >45) | 36 | 9 | 45 |
| totals | 51 | 16 | 67 |
| sensitivity | 0.4375 | specificity | 0.70588 |

| Use low LL-37 to indicate presence of stricture | CD without stricture | CD with stricture | totals |
|---|---|---|---|
| Test postive (LL-37 <45) | 15 | 7 | 22 |
| Test negative (LL-37 >45) | 36 | 9 | 45 |
| totals | 51 | 16 | 67 |
| sensitivity | 0.4375 | specificity | 0.70588 |

A

B

|  | not moderate /active UC | moderate /active UC | totals |
|---|---|---|---|
| Test positive (LL-37 <54 & CRP >2) | 2 | 3 | 5 |
| Test negative (LL-37 >54 or CRP <2) | 38 | 9 | 47 |
| totals | 40 | 12 | 52 |
| sensitivity | 0.25 | specificity | 0.95 |

A

Use CRP to indicate moderate/active UC
test positive CRP >2 = 1
test negative CRP <2 = 0
PMS 0-4 = Not moderate/active UC
PMS 5-8 = moderate/active UC
ROC = 0.771

| | Not active UC | Active UC | totals |
|---|---|---|---|
| Test positive (CRP >2) | 3 | 3 | 6.0 |
| Test negative (CRP <2) | 37 | 9 | 46.0 |
| totals | 40 | 12 | 52.0 |
| sensitivity | 0.25 | specificity | 0.925 |

D.

| | UC not in remission | UC in remission | totals |
|---|---|---|---|
| Test positive (CRP <0.5) | 11 | 20 | 31.0 |
| Test negative (CRP >0.5) | 14 | 6 | 20.0 |
| totals | 25 | 26 | 51.0 |
| sensitivity | 0.76923 | specificity | 0.56 |

INFLAMMATORY BOWEL DISEASE MARKERS AND THERAPIES FOR COLITIS-ASSOCIATED INTESTINAL FIBROSIS

CROSS REFERENCE TO RELATED APPLICATIONS

This application is a Continuation-in-part of U.S. application Ser. No. 14/648,207 filed May 28, 2015, which is a 371 National Phase application of PCT International Application No. PCT/US2013/074034 filed December 2013, which claims the benefit under 35 U.S.C. §119(e) to U.S. Application No. 61/735,372 filed Dec. 10, 2012, the disclosures of which are incorporated by reference in their entireties.

STATEMENT AS TO RIGHTS TO INVENTIONS MADE UNDER FEDERALLY SPONSORED RESEARCH AND DEVELOPMENT

This invention was made with Government support of Grant No. DK01084256, awarded by the National Institutes of Health. The Government has certain rights in the invention.

FIELD OF THE INVENTION

This invention relates to the use of a class of anti-microbial peptides for the detection and treatment of inflammatory disorders. Specifically, the anti-microbial peptide cathelicidin is useful for the detection and treatment of inflammatory bowel disease.

BACKGROUND

Chronic inflammatory disease is characterized by chronic, or persistent, inflammation. Chronic inflammatory disease encompasses a large number of diseases, many of which comprise a genetic component. Chronic inflammatory disease can develop as a result of a patient's exposure to harmful stimuli. For example, exposure to certain foods and environmental factors may trigger the development of chronic inflammatory disease. Chronic inflammatory disease can result in pain, fatigue, and digestive problems. Furthermore, the chronic nature of the inflammation may lead to tissue damage which can lead to a variety of additional problems. For example, chronic inflammation in the liver and digestive tract can lead to neurological changes such as fatigue and changes in personality. Chronic inflammation can also alter normal function of organs which can cause systemic disease and disorders in afflicted patients.

Examples of chronic inflammatory disease include celiac disease, vasculitis, lupus, chronic obstructive pulmonary disease (COPD), inflammatory bowel disease, atherosclerosis, arthritis, and psoriasis. Specifically, inflammatory bowel disease is a broad class of chronic inflammatory diseases. Examples of inflammatory bowel diseases are Crohn's disease, ulcerative colitis, collagenous colitis, lymphocytic colitis, ischaemic colitis, diversion colitis, Behcet's disease, indeterminate colitis. While many of these diseases have genetic components, the specific triggers and underlying biochemical causes for the onset of the diseases remain unknown. Furthermore, because the triggers and underlying biochemical causes of the diseases remain largely unknown, treatment regimes merely target reducing the symptoms without eliminating the disease or the chronic inflammation entirely.

Because the inflammation is not easily controlled, constant medication is often administered to lessen the symptoms and side effects of the inflammation. The medications often include antibiotics, aminosalicylates, corticosteroids, immune modifiers, and biologic therapies. However, the medication will often lead additional pain such as aching joints and headache, fatigue, digestive problems, fever, skin irritation and sensitivity, stomach pain and irritation, dizziness, increased blood pressure, fluid retention, cataracts, glaucoma, high blood sugar, increased risk of infection, osteoporosis, weak bones, suppressed adrenal gland hormone production, and increased risk of bruising and bleeding. Accordingly, even though the inflammation may lessen and worsen throughout the course of the chronic disease with the aid of medical therapies, it is often very difficult to treat and persists with most known treatment regimes.

Inflammatory bowel disease is a debilitating disease that is difficult to treat and incur high treatment cost to patients (Park K T, Bass D. Inflammatory bowel disease-attributable costs and cost-effective strategies in the United States: a review. Inflamm Bowel Dis. 2010; 17(7):1603-9). Inflamed colonic tissues express elevated levels of tumor necrosis factor alpha (TNFα) and other proinflammatory mediators, leading to tissue damage including apoptosis and loss of gut function (Ngo B, Farrell C P, Barr M, Wolov K, Bailey R, Mullin J M, et al. Tumor necrosis factor blockade for treatment of inflammatory bowel disease: efficacy and safety. Curr Mol Pharmacol. 2010; 3(3):145-52). Despite availability of medication like anti-TNFα antibodies, alternative therapeutic solutions are still being actively studied for better efficacy and safety (Rutgeerts P, Vermeire S, Van Assche G. Biological therapies for inflammatory bowel diseases. Gastroenterology. 2009; 136(4):1182-97).

The two major forms of Inflammatory Bowel Disease (IBD) are ulcerative colitis (UC) and Crohn's disease (CD). IBD is a chronic and remitting disease causing inflammation of the intestinal diseases. UC and CD have symptoms and pathologies in common, but they differ in the severity and location of the inflammation along the intestinal tract. Inflammation in UC patients is limited to the mucosal layer, and involves only the rectum and colon, while inflammation in CD patients penetrates the entire wall of the intestine and can occur anywhere along the intestinal tract. A clear diagnosis of the type of IBD is crucial to treatment decisions.

UC typically is characterized by ulcers in the colon and chronic diarrhea mixed with blood, weight loss, blood on rectal examination, and occasionally abdominal pain. UC patients may also present with a variety of other symptoms and extraintestinal manifestations including but not limited to anemia, weight loss, iritis, seronegative arthritis, ankylosing spondylitis, sacroiliitis, erythema nodosum, and pyoderma gangrenosum. Toxic megacolon is a life threatening complication of UC and requires urgent surgical intervention. UC usually requires treatment to go into remission. UC therapy includes anti-inflammatories, immunosuppressants, steroids, and colectomy (partial or total removal of the large bowel, which is considered curative). There is a significantly increased risk of colorectal cancer in UC patients several years after diagnosis, if involvement is beyond the splenic flexure, and a significant risk of primary sclerosing cholangitis, a progressive inflammatory disorder of the bile ducts.

Crohn's disease (CD) is also an IBD feat can affect the colon with symptoms similar to UC. Unlike UC, CD may affect any part of the gastrointestinal tract, and the inflammation penetrates deeper into the layers of the intestinal tact. Patients with CD may have symptoms and intestinal complications including abdominal pain, diarrhea, occult blood, vomiting, weight loss, anemia, fecal incontinence, intestinal obstructions, perianal disease, fistulae, and strictures, and apthous ulcers of the mouth. Extraintestinal complications include skin rashes, arthritis, uveitis, seronegative arthritis, peripheral neuropathy, episcleritis, fatigue, depression, erythema nodosum, pyoderma gangrenosum, growth failure in children, headache, seizures, and lack of concentration. The risk of small intestine malignancy is increased in CD patients. CD is believed to be an autoimmune disease, while it is uncertain whether there is an autoimmune component to UC. There is no known drug or surgical cure for CD; treatment focuses on controlling symptoms and maintaining remission to prevent relapse. Surgery is used for complications of Crohn's (e.g. strictures, fistulae, bleeding), and to remove segments of the intestine with active disease, but there is a high risk of recurrence; thus surgery is not considered curative.

Crohn's disease (CD) is a member of the broad class of inflammatory bowel diseases. One complication of CD is intestinal fibrosis. The intestine of CD patients develops strictures with overexpression of collagen (fibrogenic mediator) due to increased levels of transforming growth factor beta 1 (TGF-b1) and insulin like growth factor-1 (IGF-1), leading to obstruction of intestine and reduced gut motility. Intestines with strictures are unable to move, digest food or absorb nutrients. There is no satisfactory treatment of Crohn's disease associated fibrosis and stricture and surgery is often the only option for these patients. Recurrence of fibrosis or stricture formation is common in CD patients and leads to surgery that can be repeated several times and the disease progresses. Accordingly, intestinal fibrosis or stricture formation is a serious complication of CD and affects the daily live of these patients.

As described herein, cathelicidins are effective at significantly reducing intestinal fibrosis and treat inflammatory bowel diseases. Cathelicidins are a family of endogenous antimicrobial peptides which form a part of the innate immunity that protects the host from infection (Eckmann L. Defence molecules in intestinal innate immunity against bacterial infections. Curr Opin Gastroenterol. 2005; 21(2): 147-51). Cathelicidin exists in human as LL-37 and in mice as mCRAMP (Gudmundsson G H, Agerberth B, Odeberg J, Bergman T, Olsson B, Salcedo R. The human gene FALL39 and processing of the cathelin precursor to the antibacterial peptide LL-37 in granulocytes. Eur J Biochem. 1996; 238 (2):325-32; Gallo R L, Kim K J, Bernfield M, Kozak C A, Zanetti M, Merluzzi L, et al. Identification of CRAMP, a cathelin-related antimicrobial peptide expressed in the embryonic and adult mouse. J Biol Chem. 1997; 272(20): 13088-93). Cathelicidin is secreted from the apical surface that is facing exterior environment such as intestine (Schauber J, Rieger D, Weiler F, Wehkamp J, Eck M, Fellermann K, et al. Heterogeneous expression of human cathelicidin hCAP18/LL-37 in inflammatory bowel diseases. Eur J Gastroenterol Hepatol. 2006; 18(6):615-21) and salivary gland (Murakami M, Ohtake T, Dorschner R A, Gallo R L. Cathelicidin antimicrobial peptides are expressed in salivary glands and saliva. J Dent Res. 2002; 81(12):845-50) by epithelial cells (Schauber J, Rieger D, Weiler F, Wehkamp J, Eck M, Fellermann K, et al. Heterogeneous expression of human cathelicidin hCAP18/LL-37 in inflammatory bowel diseases. Eur J Gastroenterol Hepatol. 2006; 18(6):615-21) and immune cells such as macrophages (Koon H W, Shih D Q, Chen J, Bakirtzi K, Hing T C, Law I, et al. Cathelicidin signaling via the Toll-like receptor protects against colitis in mice. Gastroenterology. 2011; 141(5):1852-63 e1-3).

Cathelicidins possess antimicrobial effects (Ho S, Pothoulakis C, Koon H W. Antimicrobial peptides and colitis. Curr Pharm Des. 2012; 19(1):40-7). Cathelicidin deficient mice have increased chance of infection, have reduced angiogenesis and wound healing (Ramos R, Silva J P, Rodrigues A C, Costa R, Guardao L, Schmitt F, et al. Wound healing activity of the human antimicrobial peptide LL37. Peptides. 2011; 32(7):1469-76). A previous study showed that low plasma level of cathelicidin is associated with increased infectious disease mortality in patients undergoing hemodialysis (Gombart A F, Bhan I, Borregaard N, Tamez H, Camargo C A, Jr., Koeffler H P, et al. Low plasma level of cathelicidin antimicrobial peptide (hCAP18) predicts increased infectious disease mortality in patients undergoing hemodialysis. Clin Infect Dis. 2009; 48(4):418-24. LL-37 mRNA expression is increased in colon biopsies from ulcerative colitis (UC), but not Crohn's disease (CD) patients (Schauber J, Rieger D, Weiler F, Wehkamp J, Eck M, Fellermann K, et al. Heterogeneous expression of human cathelicidin hCAP18/LL-37 in inflammatory bowel diseases. Eur J Gastroenterol Hepatol. 2006; 18(6):615-21). However, it was unknown whether cathelicidin expression in inflammatory bowel disease patients is associated with disease activity.

Currently, IBD (such as UC and CD) can only be definitively diagnosed by colonoscopy, a rather invasive procedure; even this invasive procedure is incapable of diagnosing approximately 10% of patients undergoing colonoscopy (Burczynski, J. Mol. Diag. 8 (1): 51 (2006)). Furthermore, there is currently no satisfactory treatment or prevention of intestinal fibrosis and a limited number of effective treatments for the broader class of inflammatory bowel diseases.

Provided herein are methods of diagnosis and treatment of inflammatory bowel disease using cathelicidin. As described herein, intra-colonic and intravenous administration of cathelicidin significantly reduces intestinal fibrosis in an experimental Crohn's disease model. It is also shown herein that cathelicidin administration also significantly reduced TGF-b1- and IGF-1-induced collagen expression in human colonic fibroblasts. Furthermore, cathelicidin has been shown by others to possess anti-inflammatory effects in a chemical (dextran sulfate) acute colitis mouse model, a *Clostridium difficile* infection colitis model, but never in Crohn's disease chronic colitis model associated with fibrosis. As described herein, two in vivo models (chronic trinitrobenzene sulfonic acid (TNBS) with intracolonic cathelicidin peptide and intravenous cathelicidin expressing lentivirus) and one in vitro model (human colonic fibroblasts) were used to demonstrate that cathelicidins have anti-fibrogenic effects. This demonstrates that cathelicidin has direct anti-fibrogenic effects apart from its anti-microbial or anti-inflammatory effects. Thus, exogenous administration of cathelicidin represents a new therapeutic approach against Crohn's disease-associated intestinal fibrosis.

SUMMARY

In a first aspect, provided herein is a method of diagnosing inflammatory bowel disease. In certain embodiments, the method includes detecting cathelicidin protein expression with a probe that specifically binds cathelicidin in a biological sample from a patient. In specific embodiments, the biological sample is a colonic sample. In specific embodiments, the sample is selected from a group consisting of a blood sample, fecal sample, and intestinal sample. In specific embodiments, the sample is a colonic biopsy. In specific embodiments, the cathelicidin protein is the LL-37 peptide. In specific embodiments, the patient is a human.

In some embodiments, the inflammatory bowel disease is ulcerative colitis (UC). In exemplary embodiments, the biological sample is a blood sample. In some embodiments, a low cathelicidin protein expression level in the blood sample is indicative of moderate or active UC. In certain embodiments, the low cathelicidin protein expression level is 40 ng/ml or lower. In some embodiments, a high cathelicidin protein expression level is indicative of an UC that is in remission in the patient. In some embodiments, the high cathelicidin protein expression level is 50 ng/ml or greater.

In some embodiments, the inflammatory bowel disease is Crohn's disease. In some embodiments, the biological sample is a blood sample. In some embodiments, a low cathelicidin protein expression level is indicative that the patient has stricture associated with Crohn's disease. In certain embodiments, the low cathelicidin protein expression level is 45 ng/ml or lower. In some embodiments, a high cathelicidin protein expression level is indicative that the patient does not have stricture associated with Crohn's disease. In certain embodiments, the high cathelicidin protein expression level is 75 ng/ml or greater.

In a second aspect, provided herein is a method for treating a patient who has a likelihood of developing inflammatory bowel disease, the method comprising: (a) providing a biological sample from a patient; (b) applying the biological sample to a solid support mechanism; and (c) assaying the biological sample on the solid support mechanism to detect a cathelicidin peptide; wherein if a cathelicidin peptide is not detected or detected at low concentrations the patient is likely to develop inflammatory bowel disease; wherein if the patient is likely to develop inflammatory bowel disease the patient is administered a pharmaceutical composition to increase the patient's cathelicidin levels.

In specific embodiments, the biological sample is a colonic sample. In specific embodiments, the sample is selected from a group consisting of a blood sample, fecal sample, and intestinal sample. In specific embodiments, the sample is a colonic biopsy. In specific embodiments, the cathelicidin peptide is LL-37. In specific embodiments, the patient is a human. In specific embodiments, the assaying is performed using an ELISA. In specific embodiments, the assaying is performed using an assay selected from the group consisting of FACS, Western blot, immunohistochemistry, and RT-PCR. In specific embodiments, a low concentration of cathelicidin is less than 20 pg/ug. In specific embodiments, a high concentration of cathelicidin is greater than 35 pg/ug.

In a third aspect, provided herein is a method for determining the likelihood of a patient who previously suffered from inflammatory bowel disease to relapse, the method comprising detecting cathelicidin protein levels wherein high levels of cathelicidin protein are predictive of a longer disease free period compared to a patient who previously suffered from inflammatory bowel disease who has low levels of cathelicidin protein.

In specific embodiments, the cathelicidin protein levels are LL-37 peptide levels. In specific embodiments, the high levels of cathelicidin protein are further predictive of a lower chance of repeated surgery. In specific embodiments, the high levels of cathelicidin protein are further predicative of fewer inflammatory bowel disease related hospitalizations. In specific embodiments, the high levels of cathelicidin protein are further predictive of normal white blood cell counts.

In specific embodiments, the inflammatory bowel disease is Crohn's disease. In specific embodiments, the inflammatory bowel disease is ulcerative colitis. In specific embodiments, the cathelicidin protein levels are colonic cathelicidin protein levels. In specific embodiments, the biological sample is a colonic sample. In specific embodiments, the high levels of colonic cathelicidin protein are levels of LL-37 protein above 35 pg/ug. In specific embodiments, the high levels of colonic cathelicidin protein are levels of LL-37 protein below 20 pg/ug. In specific embodiments, the high levels of colonic cathelicidin protein have a significantly lower disease development score (approximately 45%), compared to those with lower colonic cathelicidin level.

In specific embodiments, the biological sample is a blood sample. In specific embodiments, the biological sample is a fecal sample or an intestinal sample.

In specific embodiments, high levels of cathelicidin protein are predictive of the patient not relapsing for at least 2 years. In specific embodiments, the cathelicidin protein levels are detected by ELISA. In specific embodiments, the cathelicidin levels are detected by assay selected from the group consisting of FACS, Western blot, immunohistochemistry, and RT-PCR.

In specific embodiments, the patient is a human.

In a fourth aspect, provided herein is a method for determining the likelihood of a patient to develop an inflammatory bowel disease, the method comprising detecting cathelicidin protein levels in a biological sample from the patient, wherein low levels of cathelicidin protein are predictive of a likelihood of a patient to develop an inflammatory bowel disease.

In specific embodiments, the cathelicidin protein levels are LL-37 peptide levels. In specific embodiments, the low levels of cathelicidin protein are further predictive of a higher chance of inflammatory bowel disease related surgery. In specific embodiments, the low levels of cathelicidin protein are further predicative of inflammatory bowel disease related hospitalizations. In specific embodiments, the low levels of cathelicidin protein are further predictive of abnormal white blood cell counts and anemia.

In specific embodiments, the inflammatory bowel disease is Crohns' disease. In specific embodiments, the inflammatory bowel disease is ulcerative colitis. In specific embodiments, the cathelicidin protein levels are colonic cathelicidin protein levels. In specific embodiments, the biological sample is a colonic sample. In specific embodiments, the high levels of colonic cathelicidin protein are levels of LL-37 protein above 35 pg/ug. In specific embodiments, the high levels of colonic cathelicidin protein are levels of LL-37 protein below 20 pg/ug. In specific embodiments, the high levels of colonic cathelicidin protein have a significantly lower disease development score (approximately 45%), compared to those with lower colonic cathelicidin protein levels.

In specific embodiments, the biological sample is a blood sample. In specific embodiments, the biological sample is a fecal sample or an intestinal sample. In specific embodiments, high levels of cathelicidin protein are predictive of the patient not developing an inflammatory bowel disease for at least 2 years.

In specific embodiments, the cathelicidin protein levels are detected by ELISA. In specific embodiments, the cathelicidin protein levels are detected by assay selected from the group consisting of FACS, Western blot, immunohistochemistry, and RT-PCR.

In specific embodiments, the patient is a human.

In a fifth aspect, provided herein is a method of treating inflammatory bowel disease, the method comprising administering to a subject with an inflammatory bowel disease a pharmaceutical composition to increase the patient's cathelicidin protein levels.

In specific embodiments, the inflammatory bowel disease is Crohn's disease. In specific embodiments, the inflammatory bowel disease is ulcerative colitis. In specific embodiments, the pharmaceutical composition comprises a cathelicidin peptide and a pharmaceutically acceptable carrier. In specific embodiments, the cathelicidin peptide is a LL-37 pepetide. In specific embodiments, the pharmaceutical composition is sodium butyrate. In specific embodiments, the pharmaceutical composition comprises a short chain fatty acid. In specific embodiments, the pharmaceutical composition comprises vitamin D. In specific embodiments, the pharmaceutical composition comprises a PPAR gamma agonist. In specific embodiments, the pharmaceutical composition comprises a lipopolysaccharide. In specific embodiments, the pharmaceutical composition comprises Salmononella. In specific embodiments, the pharmaceutical composition comprises a probiotic.

In specific embodiments, the pharmaceutical composition further comprises one or more therapies selected from the group consisting of cathelicidin peptide(s), sodium butyrate or analogs thereof, antibiotic(s), anti-inflammatory(ies), anti-diarrheals, laxatives, pain relievers, iron supplements, aminosalicylate(s), steroids, corticosteroid(s), immune modifier(s), immunosupressor(s), anti-CD52 agents, anti-TNFα agents, biologic therapy(ies), vitamin B-12 shots, surgery, sodium butyrate, and nutritional plans.

In specific embodiments, the anti-inflammatory(ies) is selected from a group comprising sufasalazine, mesalamine, NSAIDs, ImSAIDs, and corticosteroids.

In specific embodiments, the immunosupressor(s) is selected from a group comprising zathioprine, mercaptopurine, infliximab, adalimumab, certolizumab pegol, methodtrexate, cyclosporine, natalizumab, cyclosporine, and tacrolimus.

In specific embodiments, the antibiotic(s) is selected from a group comprising metronidazol and ciprofloxacin.

In specific embodiments, the anti-CD52 agent is Alemtuzumab®.

In specific embodiments, the nti-TNFα agent is Infliximab®.

In specific embodiments, the method is a method of treating Crohn's disease comprising administering a pharmaceutical composition to increase the in vivo concentration of cathelicidin protein.

In specific embodiments, the Crohn's disease is associated with fibrosis. In specific embodiments, the Crohn's disease is associated with strictures.

In specific embodiments, the pharmaceutical composition is administered intracolonically. In specific embodiments, the pharmaceutical composition is administered intravenously. In specific embodiments, the pharmaceutical composition is administered orally.

In specific embodiments, the pharmaceutical composition significantly reduces intestinal fibrosis. In specific embodiments, the pharmaceutical composition significantly reduces TGF-b1 and IGF-1 induced collagen expression in colonic fibroblasts. In specific embodiments, the significant reduction of collagen expression treats intestinal fibrosis. In specific embodiments, the significant reduction of collagen expression decreases intestinal fibrosis. In specific embodiments, the significant reduction of collagen expression prevents intestinal fibrosis.

In specific embodiments, the patient is human.

In a sixth aspect, provided herein is a method of reducing TGF-b1 and IGF-1 expression in colonic fibroblasts, the method comprising administering a cathelicidin peptide. In specific embodiments, the cathelicidin peptide is a LL-37 peptide. In specific embodiments, the colonic fibroblasts are human colonic fibroblasts.

In a seventh aspect, provided herein is a kit comprising: (a) a solid support comprising synthetic capture probes selective for a cathelicidin peptide; and (b) methods of using the kit wherein the methods comprise instructions for obtaining a biological sample from a patient, applying the biological sample to the solid support, and assaying the biological sample on the solid support mechanism to detect a cathelicidin peptide. In specific embodiments, the cathelicidin peptide is a LL-37 peptide. In specific embodiments, the assay is selected from a group consisting of ELISA assays, FACS assays, Western blot assays, immunohistochemistry assays, and RT-PCR assays.

In an eight aspect, provided herein is a kit comprising antibodies, a detectable label and instructions for treating and detecting inflammatory bowel disease, wherein the antibodies specifically recognize a cathelicidin peptide. In specific embodiments, the cathelicidin peptide is a LL-37 peptide.

In a ninth aspect, provided herein is a method for detecting an active inflammatory bowel disease in a patient. In an exemplary embodiment, the method includes the step of detecting cathelicidin protein levels and C-reactive protein (CRP) levels in a biological sample from the patient, wherein low levels of cathelicidin protein and high CRP levels are indicative of an active inflammatory bowel disease. In some embodiments, the cathelicidin protein levels are LL-37 peptide levels. In certain embodiments, the inflammatory bowel disease is ulcerative colitis (UC). In some embodiments, the cathelicidin protein levels and CRP protein levels are serum cathelicidin protein levels and serum CRP protein levels. In certain embodiments, the patient has active ulcerative colitis if the patient has a serum cathelicidin protein level of 55 ng/ml or below and a serum CRP level of 2 mg/L or above. In exemplary embodiments, the biological sample is a blood sample.

In some embodiments, the cathelicidin protein levels and CRP protein levels are detected using a cathelicidin binding probe and a CRP binding probe. In certain embodiments, the cathelicidin binding probe is an antibody that binds cathelicidin and the CRP binding probe is an antibody that binds CRP. In some embodiments, the cathelicidin binding probe and the CRP binding probe are attached to a solid support. In certain embodiments, the cathelicidin and CRP protein levels are detected by ELISA. In other embodiments, the cathelicidin protein levels are detected by assay selected from the group consisting of FACS, Western blot, and immunohistochemistry. In some embodiments, the patient is a human.

In a tenth aspect, provided herein is an antibody cocktail that includes a plurality of antibodies and a buffer solution. In some embodiments, the plurality of antibodies includes an anti-CRP antibody and an anti-cathelicidin antibody. In certain embodiments, the anti-cathelicidin antibody binds LL-37. In exemplary embodiments, the antibodies in the plurality of antibodies are monoclonal antibodies.

BRIEF DESCRIPTION OF THE DRAWINGS

FIGS. 1A-1D show that Cathelicidin reduces colonic inflammation in TNBS mediated chronic colitis in mice.

FIG. 1A is an illustration of the experimental plan of TNBS mediated chronic colitis. Wild-type and mCRAMP mice were injected with TNBS solution (0.5-1 mg per 20 g mice) in 30% ethanol or 30% ethanol only (vehicle control) under transient isoflurane anesthesia. FIG. 1B shows the percent of body weight change of different groups (from week 0 to week 7). All ethanol treated groups had approximately 20% body weight gain. TNBS treated wild-type mice suffered from significantly less body weight gain, compared to ethanol control (p=0.03). Administration of mCRAMP to TNBS treated wild-type restored the body weight gain (p=0.01). TNBS treated Camp$^{-/-}$ mice had significant body weight loss regardless of mCRAMP treatment, compared to TNBS treated wild-type mice (p=0.001) and ethanol treated Camp$^{-/-}$ mice (p=0.0001). FIG. 1C shows representative H&E images of colonic tissues. FIG. 1D shows the histology score was based on H&E staining images of colonic tissues. TNBS treatment in wild-type mice led to increased tissue damage with significantly higher histology score (p=0.001), compared to ethanol control. Treatment of mCRAMP significantly reduced histology score in wild-type mice (p=0.03) and Camp$^{-/-}$ mice (p=0.04). Results are representative of n=6 mice per group.

FIGS. 2A-2D show that cathelicidin reduces colonic collagen deposition in mice with chronic TNBS colitis. FIG. 2A shows that TNBS treatment significantly induced colonic TNFα protein (p=0.0042) expression. Intracolonic mCRAMP administration significantly reduced TNBS induced TNFα protein expression in WT (p=0.0127) and Camp$^{-/-}$ (p=0.0054) mice. FIG. 2B shows that TNBS treatment significantly induced colonic TNFα protein (p=0.0042) expression. Intracolonic mCRAMP administration significantly reduced TNBS induced TNFα protein expression in WT (p=0.0127) and Camp$^{-/-}$ (p=0.0054) mice. FIG. 2C shows Masson Trichrome staining for collagen in colonic tissues. Collagen was stained in blue. Collagen deposited in mucosal and submucosal layer of TNBS treated wild-type mice was reduced by CRAMP treatment. FIG. 2D shows quantitative real-time RT-PCR of collagen colla2 mRNA expression in colonic tissues of mice. TNBS treatment significantly induced colonic collagen deposition and colla2 mRNA (p=0.00376) expression. Intracolonic treatment of mCRAMP reduced colonic colla2 mRNA and collagen deposition in both WT (p=0.0364) and Camp$^{-/-}$ (p=0.04) mice. Results are representative of n=6 mice per group.

FIG. 3A shows colonic Camp mRNA expression levels of TNBS treated WT and Camp$^{-/-}$ mice were similar. Camp mRNA in Camp$^{-/-}$ mice was undetectable. FIG. 3B shows that colonic Camp mRNA expression levels among strictured CD patients and non-strictured CD patients were similar. FIGS. 3C and 3D show human colonic CCD-18Co fibroblasts were incubated with LL-37 (1-10 μM) or TFA 0.1% (vehicle) and/or TGF-β1 (50 ng/ml) and IGF-1 (10 ng/ml) for 48 hours. Collagen (COL1A2) and total ERK protein expression was detected by Western blot analyses and quantitative image densitometry. TGF-β1 and IGF-1 significantly induced COL1A2 mRNA expression in CCD-18Co fibroblasts (p=0.0341) which was reduced by 10 μM LL-37 (p=0.0001). FIG. 3E shows that CCD-18Co fibroblasts were treated with LL-37 (0-10 μM) and/or TGF-β1 (50 ng/ml) and IGF-1 (10 ng/ml) for 24 hours. TGF-β1 and IGF-1 induced COL1A2 mRNA expression in colonic fibroblasts (P=0.049) was inhibited by LL-37 (5-10 μM, p=0.001) in concentration dependent manner. FIG. 3F shows human primary colonic fibroblasts that were treated with LL-37 (0-10 μM) and/or TGF-β1 and IGF-1 for 24 hours. TGF-β1 and IGF-1 induced COL1A2 mRNA expression in colonic fibroblasts (P=0.0233) was inhibited by LL-37 (5-10 μM, p=0.0108 and p=0.0049) in concentration dependent manner. All experiments are representative of 3 independent experiments.

FIGS. 4A-4E show that cathelicidin inhibits TGF-β1 and IGF-1 mediated collagen synthesis via ERK activation in the human colonic fibroblasts. FIG. 4A shows CCD-18Co fibroblasts that were pretreated with DMSO, Akt inhibitor V (10 μM) or ERK inhibitor PD98059 (10 μM) for 30 minutes, followed by LL-37 (10 μM) or TFA 0.1% and/or TGF-β1 (50 ng/ml) and IGF-1 (10 ng/ml) for 72 hours. COL1A2 and Stat5 protein expression was detected by Western blot. FIG. 4B shows densitometry of Western blots. The inhibition of TGF-β1 and IGF-1 mediated COL1A2 expression by LL-37 was partially reversed by PD98059 (p=0.0001). FIG. 4C shows CCD-18Co fibroblasts that were pretreated with DMSO, Akt inhibitor V (10 μM) or ERK inhibitor PD98059 (10 μM) for 30 minutes, followed by LL-37 (10 μM) or TFA 0.1% and/or TGF-β1 (50 ng/ml) and/or IGF-1 (10 ng/ml) for 30 minutes. FIGS. 4D and 4E show densitometry of Western blots. LL-37 significantly induced Akt and ERK phosphorylation in concentration dependent manner.

FIGS. 5A-5C show that cathelicidin reduces collagen expression via inhibiting tubulin expression in colonic fibroblasts. FIG. 5A shows CCD-18Co fibroblasts that were pretreated with DMSO, cytoskeleton inhibitor cytochalasin B (10 μM) or matrix metalloproteinase (MMP) inhibitor OM6001 (10 μM) for 30 minutes, followed by LL-37 (10 μM) or TFA 0.1% and/or TGF-β1 (50 ng/ml) and IGF-1 (10 ng/ml) for 72 hours. Cytochalasin B but not OM6001 affected TGF-β1 and IGF-1 induced COL1A2 expression in CCD-18Co fibroblast (p=0.0005). Interference of cytoskeleton led to inhibition of collagen expression. FIG. 5B shows that cytochalasin B but not OM6001 affected TGF-β1 and IGF-1 induced β-tubulin expression in CCD-18Co fibroblasts (p=0.0005). Interference of cytoskeleton inhibited β-tubulin expression. FIG. 5C shows CCD-18Co fibroblasts that were pretreated with DMSO, Akt inhibitor V (10 μM) or ERK inhibitor PD98059 (10 μM) for 30 minutes, followed by LL-37 (10 μM) or TFA 0.1% and/or TGF-β-1 (50 ng/ml) and IGF-1 (10 ng/ml) for 72 hours. Both ERK and Akt pathways were not involved in the LL-37 mediated inhibition of β-tubulin expression in CCD-18Co fibroblasts. All experiments are representative of 3 independent experiments.

FIG. 6A shows CCD18Co fibroblasts that were exposed to TFA (vehicle), LL-37 (10 μM) and/or TGF-β-1 (50 ng/ml) and IGF-1 (10 ng/ml) for 24 hours. Tubulin distribution was visualized by tubulin tracker in green color and nuclei were identified by Hoechst 33342 in blue color. TGF-β-1 (50 ng/ml) and IGF-1 (10 ng/ml) did not affect tubulin distribution in cells. LL-37 shrunk the tubulin network. FIG. 6B shows CCD18Co fibroblasts that were exposed to cytochalasin B (10 μM) for 24 hours. Cytochalasin B also shrunk tubulin network in cells. Results are representative of 3 independent experiments.

FIG. 7A shows vimentin immunohistochemistry for fibroblasts in colonic tissues (in light brown spots). Fibroblasts accumulated in the mucosal and submucosal locations as collagen deposition. FIG. 7B shows the number of fibroblasts per field of image. Three different locations (3 separate images)

per sample were counted. Chronic TNBS colitis led to significantly increased fibroblast accumulation (P=0.0032) compared to ethanol control but it was not affected by mCRAMP administration. FIGS. 7C and 7D show colonic vimentin and α-smooth muscle actin mRNA expression levels were similar among WT and Camp−/− mice. mCRAMP administration did not affect colonic vimentin and α-SMA mRNA expression in colons. FIG. 7E shows CCD-18Co that was seeded on the upper modified Boyden chamber and incubated in 37° C. for 8 hours. Cell migration was not affected by LL-37 (0-10 µM). Results are representative of 3 independent experiments.

FIGS. 8A-8D show that intravenous administration of mCRAMP expressing lentivirus ameliorates TNBS mediated colonic fibrosis. FIG. 8A shows an illustration of experimental plan of TNBS mediated chronic colitis. Wild-type and mCRAMP mice were injected with TNBS solution (0.5-1 mg per 20 g mice) in 30% ethanol or 30% ethanol only (vehicle control) under transient isoflurane anesthesia. FIG. 8B shows colonic Camp mRNA expression that was significantly increased in the mCRAMP expressing Camp-LV group (p=0.026 or p=0.0413). FIG. 8C shows Colonic colla2 mRNA expression was significantly reduced in mCRAMP expressing Camp-LV group. FIG. 8D shows that colonic vimentin mRNA expression was not affected by Camp-LV infection. Results are representative of n=6 mice per group.

FIGS. 9A-9E show that high colonic LL-37 expression levels predicts good prognosis of the UC patients. FIG. 9A shows colonic Camp mRNA expression of 17 normal, 24 UC and 24 CD patients. Only UC patients have significantly higher Camp mRNA expression than normal patients (p=0.04). FIG. 9B shows colonic LL-37 protein levels in 17 normal, 24 UC and 24 CD patients. FIG. 9C shows cathelicidin immunohistochemistry of colons from normal, UC and CD patients. FIG. 9D shows the definition of disease development score. FIG. 9E shows disease development scores of normal, UC and CD patients. A low colonic LL-37 protein level is significantly associated with high disease development among UC patients (p=0.02 UC high LL-37 vs. UC low LL-37). Baseline characteristics and number of all groups are shown in FIGS. 10 and 11.

FIGS. 10A-10C show the baseline characteristics of all patient groups. FIG. 10A shows the baseline characteristics of all control, UC and CD groups. FIG. 10B shows the inclusion and exclusion criteria of the analysis. FIG. 10C shows the disease development scores of normal, UC and CD patients. But there is no correlation between disease development score of IBD patients and colonic Camp mRNA expression.

FIGS. 11A and 11B show the baseline characteristics of specific patient groups. FIG. 11A shows the baseline characteristics of low and high cathelicidin UC groups. FIG. 11B shows the baseline characteristics of low and high cathelicidin CD groups.

FIGS. 12A-12E show that intestinal cathelicidin protein levels vary among IBD patients. FIG. 12A Inclusion and exclusion criteria. FIG. 12B Baseline characteristics. FIG. 12C Intestinal CAMP mRNA expression of normal and IBD patients. UC, but not CD patients had significantly increased intestinal CAMP mRNA expression. FIG. 12D The average intestinal cathelicidin levels of were not altered in IBD. FIG. 12E Immunohistochemistry of cathelicidin in human intestinal biopsies. Cathelicidin was expressed in mucosal area of the intestines (brown color) with wide variation.

FIGS. 13A-13C show intestinal cathelicidin protein levels correlate with CRP or ESR levels. FIG. 13A Baseline characteristics. FIG. 13B Serum CRP levels. Low intestinal cathelicidin levels were significantly correlated to the high serum CRP levels in UC patients. FIG. 13C ESR levels. Low intestinal cathelicidin levels were significantly correlated to the high ESR levels in CD patients. CRP levels were not correlated to cathelicidin levels in UC patients. ESR levels were not correlated to cathelicidin levels in CD patients.

FIGS. 14A and 14B shows the inclusion and exclusion criteria as well as baseline characteristics of the patients. FIG. 14C show the plasma cathelicidin levels of UC, but not CD, patients were significantly decreased.

FIGS. 15A-15D show endogenous cathelicidin induction by sodium butyrate ameliorated DSS mediated colitis in mice. FIG. 15A is an illustration of the administration of DSS and/or sodium butyrate to mCRAMP deficient (Camp$^{-/-}$) and wild-type mice (i.e., the experimental plan). FIG. 15B shows that DSS colitis led to body weight loss. FIG. 15C shows that DDS colitis led to significant tissue damages and increased histology scores, wherein intraperitoneal sodium butyrate administration led to significant decrease of histology score in wild-type but not Camp$^{-/-}$ deficient mice. FIG. 15D shows that Camp$^{-/-}$ mice had significantly worse colitis than wild-type mice when exposed to DSS (see also FIG. 15C).

FIG. 16A shows that colonic TNFα levels by DSS exposed mice. Sodium butyrate treatment significantly reduced colonic TNFα levels in both wild-type and Camp$^{-/-}$ mice (p=0.04). The decrease of TNFα levels in Camp$^{-/-}$ mice was minimized (drop by 4 pg/µg protein), compared to wild-type mice (drop by 6 pg/µg protein). FIG. 16B shows that colonic microflora load (16S) was detected by PCR. Endogenous cathelicidin or sodium butyrate administration did not alter colonic 16S expression. FIG. 16C shows that colonic Camp mRNA expression. DSS significantly induced colonic Camp mRNA expression that was further augmented by sodium butyrate treatment. FIG. 16D shows that colonic mCRAMP and beta-tubulin protein expression was detected by Western blot analyses. Sodium butyrate administration increased colonic mCRAMP protein expression in DSS treated wild-type mice. FIG. 16E shows that serum starved Raw264.7 macrophages were treated with 5 mM of sodium butyrate for 6 and 24 hours. Both conditions significantly increased Camp mRNA expression in macrophages. FIG. 16F shows that serum starved human colonic epithelial NCM460 cells were treated with 5 mM of sodium butyrate for 16 hours. Cathelicidin protein level in conditioned media was significantly increased. All experiments are representative of 3 independent experiments.

FIGS. 17A-17E shows that cathelicidin inhibited LPS induced TNFα expression in macrophages was GPCR dependent. FIG. 17A shows that serum starved human PBMCs were incubated with E. coli DNA (0.5 µg/ml), LPS (0.1 µg/ml), LL-37 (1-10 µM) or TFA 0.1% (vehicle) for 16 hours. LL-37 (10 µM) significantly reduced LPS induced TNFα protein expression in conditioned media. LL-37 had no inhibitory effect against E. coli DNA induced TNFα expression. FIG. 17B shows that fresh human colonic biopsies were incubated with LPS (0.1 µg/ml), LL-37 (1-10 µM) or TFA 0.1% (vehicle) for 16 hours. LL-37 (10 µM) almost abolished LPS induced TNFα protein expression in conditioned media. FIG. 17C shows that serum starved Raw 264.7 macrophages were incubated with E. coli DNA (0.5 µg/ml), LPS (0.1 µg/ml), mCRAMP (1-10 µM) or TFA 0.1% (vehicle) for 16 hours. mCRAMP (10 μM) significantly reduced LPS induced TNFα protein expression in conditioned media. mCRAMP had no inhibitory effect against *E. coli* DNA induced TNFα expression. FIG. 17D shows that mCRAMP had no inhibitory effect against flagellin (50 ng/ml) induced TNFα expression. FIG. 17E shows that serum starved Raw264.7 macrophages were pretreated with pertussis toxin (500 ng/ml) overnight, followed by incubation with LPS (0.1 μg/ml), mCRAMP (1-10 μM) or TFA 0.1% (vehicle) for 16 hours. The inhibitory effect of cathelicidin against LPS induced TNFα expression was revered by pertussis toxin, suggesting GPCR dependent anti-inflammatory effect.

FIG. 18A shows that serum starved Raw264.7 macrophages were pretreated with mouse IGF-1 (80 pg/ml) for 30 minutes followed by incubation with LPS (0.1 μg/ml), TFA and mCRAMP (10 μM) for 16 hours. Addition of mouse IGF-1 reversed the mCRAMP mediated inhibition of LPS induced TNFα secretion. FIG. 18B shows that serum starved Raw264.7 macrophages were pretreated with DMSO, Akt inhibitor V Triciribine (10 μM) for 30 minutes, followed by incubation with LPS (0.1 μg/ml), TFA and mCRAMP (10 μM) for 16 hours. LPS induced TNFα expression is Akt dependent. FIGS. 18C-18E show that serum starved Raw 264.7 macrophages were incubated with LPS (0.1 μg/ml) with TFA and mCRAMP (10 μM) for 30 minutes. LPS induced Akt and ERK phosphorylation was significantly suppressed by mCRAMP. All experiments are representative of 3 independent experiments. FIG. 18A shows that summary of the anti-inflammatory mechanism of cathelicidin.

FIGS. 19A and 19B show that serum starved Raw464.7 macrophages were incubated with LPS (0.1 μg/ml), TFA and mCRAMP (10 μM) for 6 and 16 hours. mCRAMP did not alter LPS induced TNF mRNA expression in macrophages. FIG. 19C shows that serum starved Raw264.7 macrophages were pretreated with P2X7 receptor antagonist KN62 (10 μM) and FPR2 receptor antagonist WRW4 (10 μM) for 30 minutes, followed by incubation with LPS (0.1 μg/ml), TFA and mCRAMP (10 μM) for 16 hours. Inhibition of P2X7 and FPR2 did not alter the anti-inflammatory effect of cathelicidin. FIG. 19D shows that serum starved Raw264.7 macrophages were pretreated with DMSO (vehicle) or U0126 (10 μM) for 30 minutes, followed by incubation with LPS (0.1 μg/ml), TFA and mCRAMP (10 μM) for 16 hours. Inhibition of MAP kinase suppressed LPS induced TNFα expression. FIG. 19E shows that serum starved Raw264.7 macrophages were pretreated with insulin like growth factor receptor 1 (IGF-1R) AGL2263 (10 μM) and AG538 (10 μM) for 30 minutes, followed by incubation with LPS (0.1 μg/ml), TFA and mCRAMP (10 μM) for 16 hours.

FIG. 20A is an illustration of TNBS experimental plan. FIG. 20B shows the body weight change of TNBS treated groups. FIG. 20C shows the body weight change of ethanol treated normal groups. FIG. 20D shows H&E staining FIG. 20E shows the histological score of TNBS treated acute colitis groups. TNBS treated Camp$^{-/-}$ mice had lower body weight (p=0.0444) and higher histological score (p=0.04) than wild-type mice, reflecting more severe colitis. mCRAMP treatment significantly reduced histological damage in wild-type mice (p=0.0006) and Camp$^{-/-}$ mice (p=0.0484) with acute colitis. Experiments included n=6 mice per group.

FIGS. 21A-21D show that intracolonic mCRAMP administration significantly reduced colonic 16S expression in wild-type mice and Camp$^{-/-}$ mice with acute colitis. FIG. 21A shows colonic TNFα levels. TNBS induced colitis resulted in significantly elevated colonic TNFα p=0.0073 levels, compared to ethanol control group. TNBS treated Camp$^{-/-}$ mice had significantly higher colonic TNFα levels than wild-type mice. Administration of mCRAMP significantly reduced colonic TNFα levels in wild-type mice and Camp$^{-/-}$ mice with acute colitis. FIGS. 21B and 21C show colonic Camp mRNA expression of mice. Exposure to TNBS significantly induced colonic Camp mRNA expression on day 3 (p=0.0152) but not day 7. FIG. 21D shows the relative 16S DNA expression in colons. There was no significant difference in 16S expression among wild-type and Camp-/- mice. n=6 mice per group.

FIGS. 29A-D are receiver operating characteristics (ROC) curves showing the ability of CRP expression levels alone to diagnose moderate/active ulcerative colitis (UC) (FIG. 29A, ROC curve area=0.771) and UC remission (FIG. 29B, ROC curve area=0.712).

DETAILED DESCRIPTION

Overview

Figure 1C:
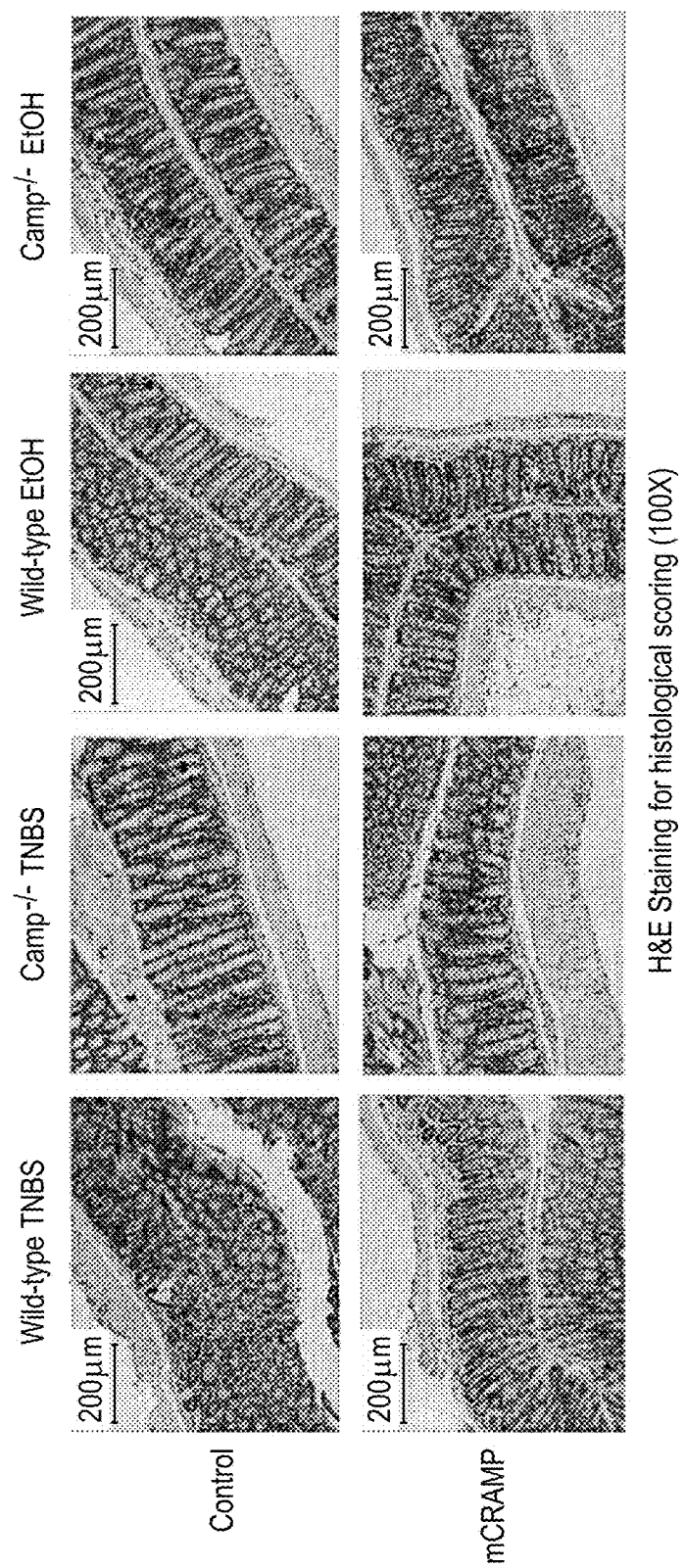
Figure 2C:
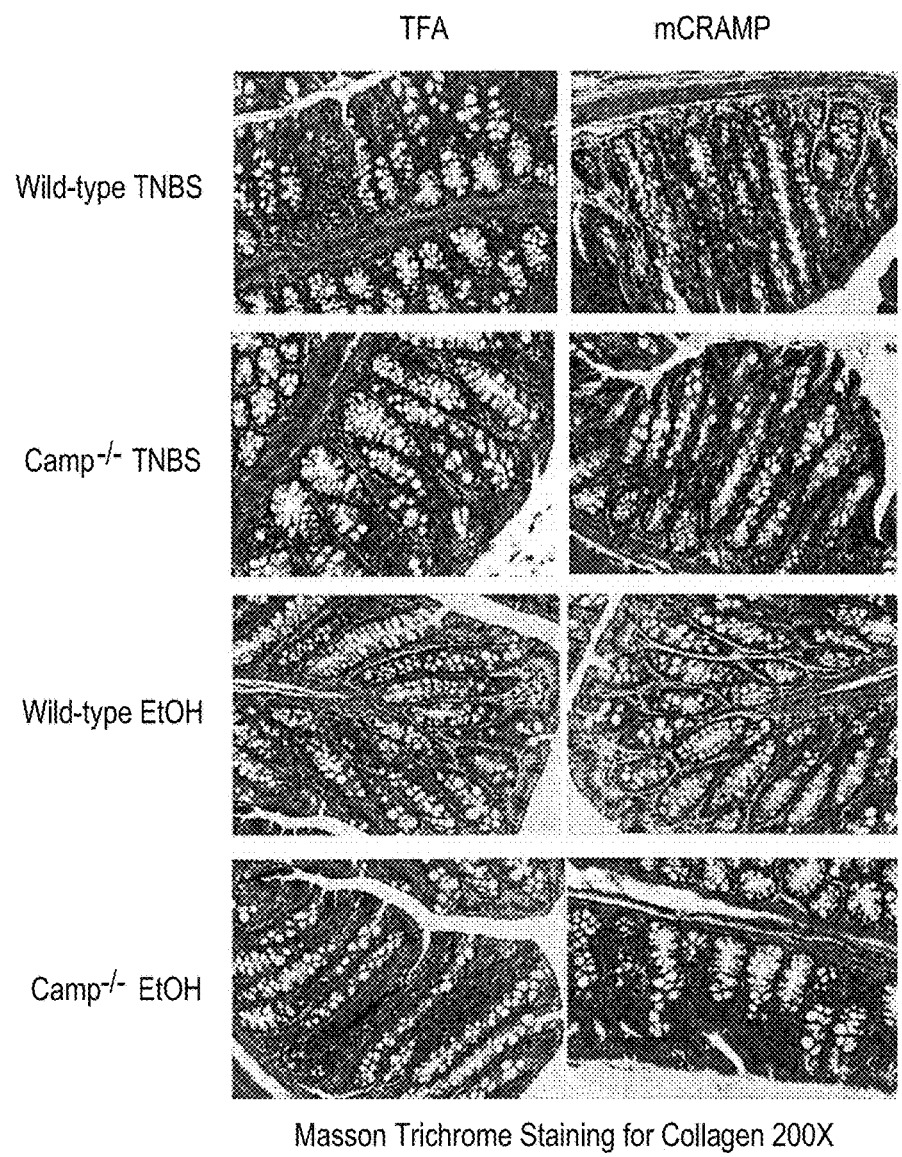
Figure 3A:
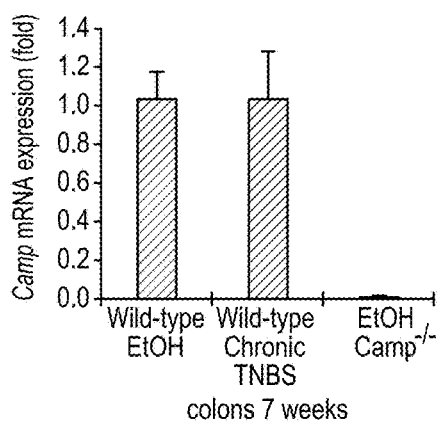
FIGS. 3A-3F show that cathelicidin reduces collagen expression in colonic fibroblasts.
Figure 3B:
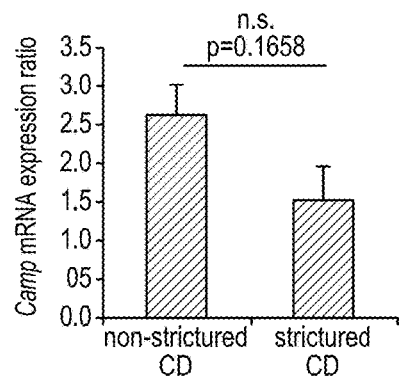
Figure 3C:
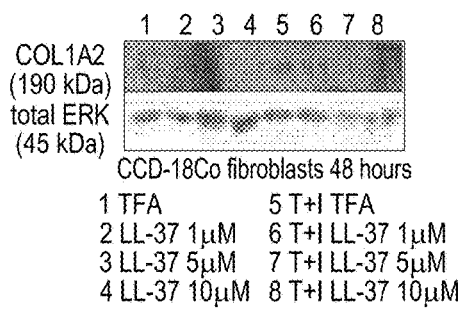
Figure 3D:
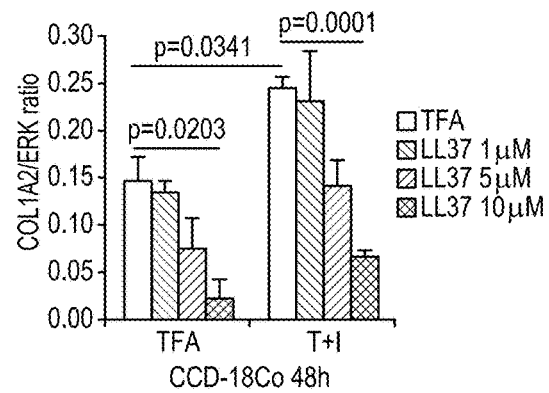
Figure 3E:
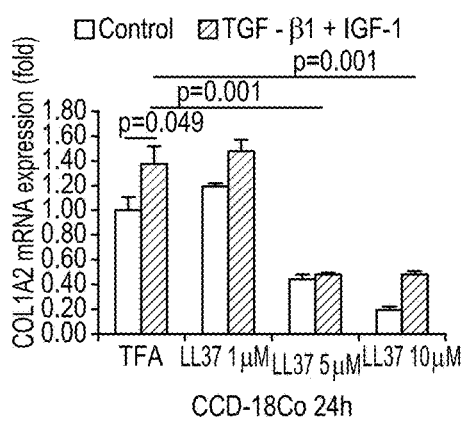
Figure 3F:
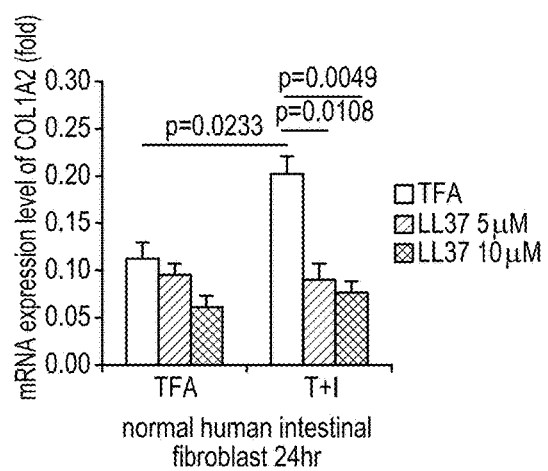
Figure 6A:
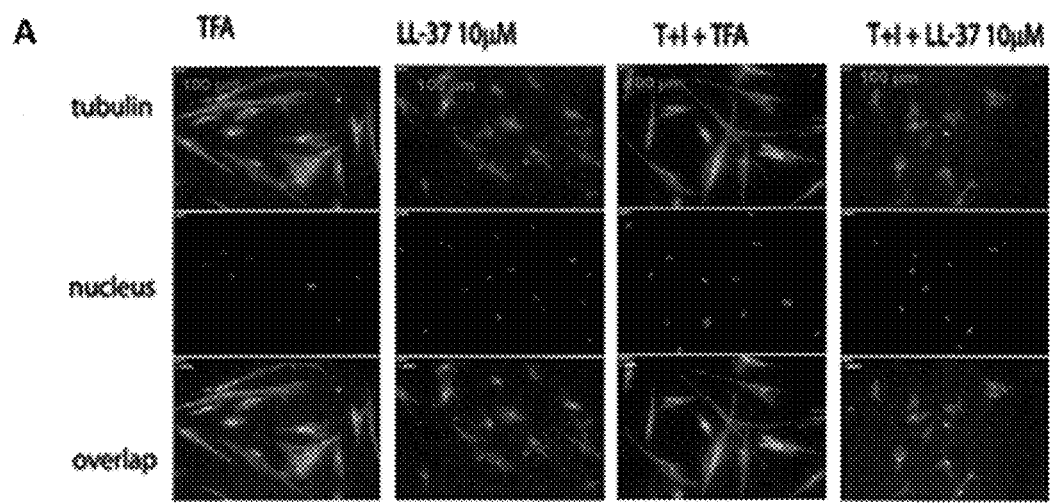
FIGS. 6A and 6B show that cathelicidin inhibits cytoskeleton tubulin distribution in colonic fibroblasts.
Figure 6B:
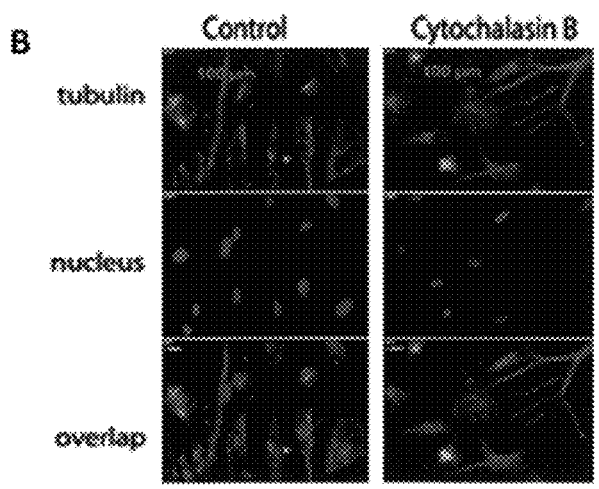
Figure 7A:
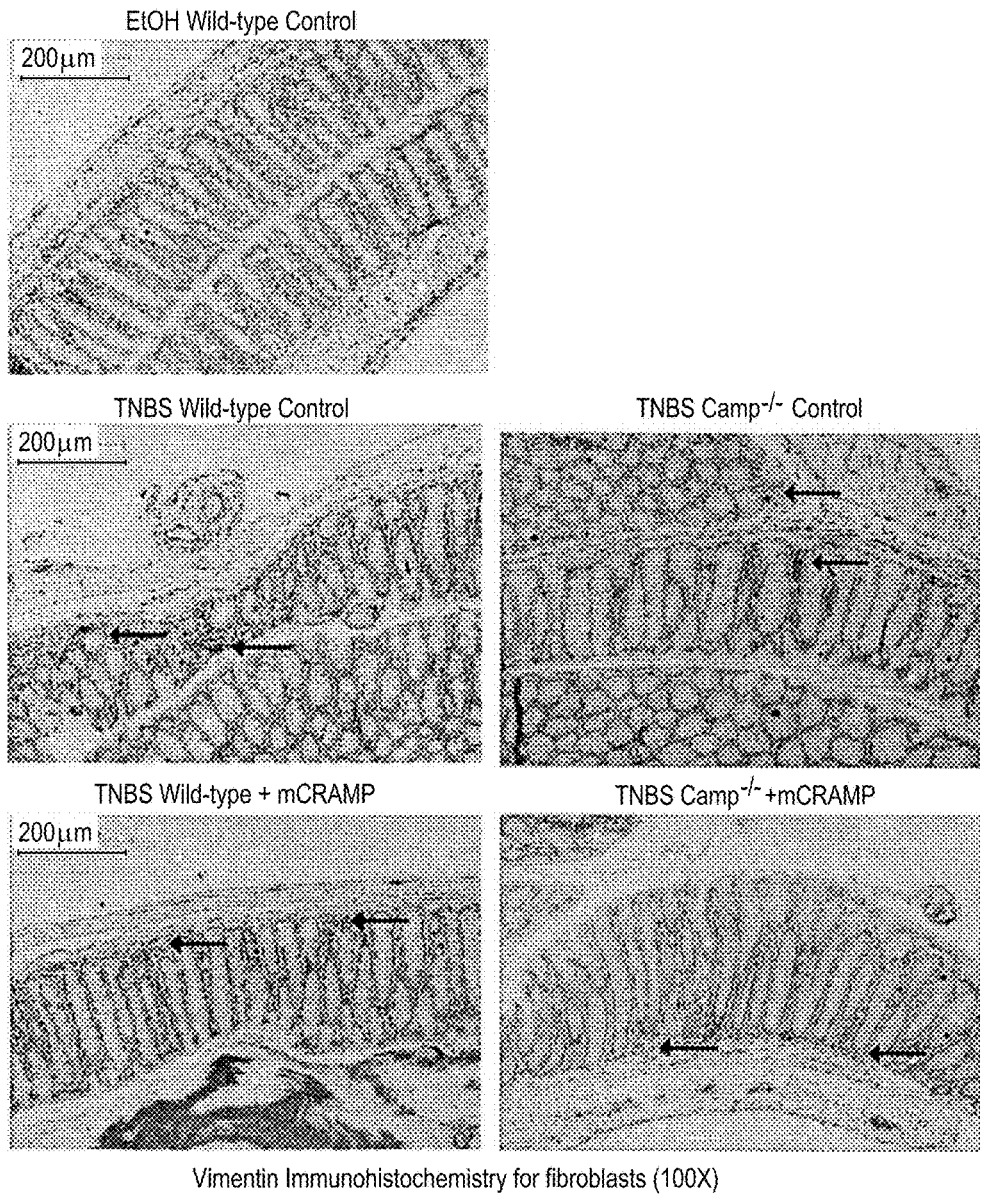
FIGS. 7A-7E show that cathelicidin does not affect colonic fibroblast infiltration in TNBS treated colitis.
Figure 7B:
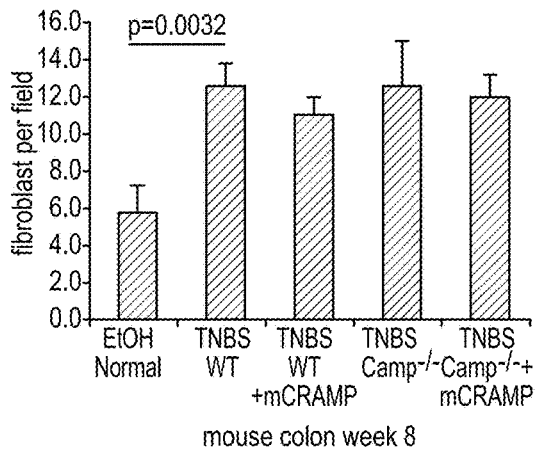
Figure 7C:
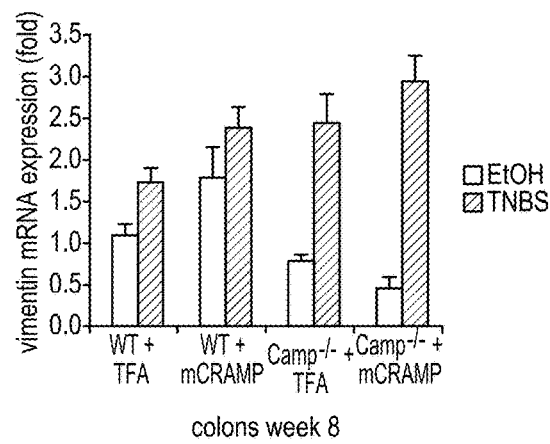
Figure 7D:
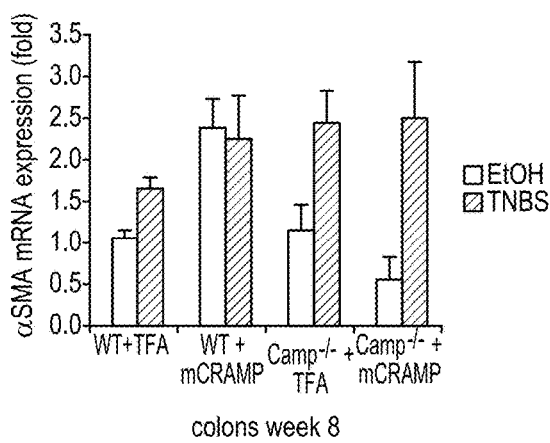
Figure 7E:
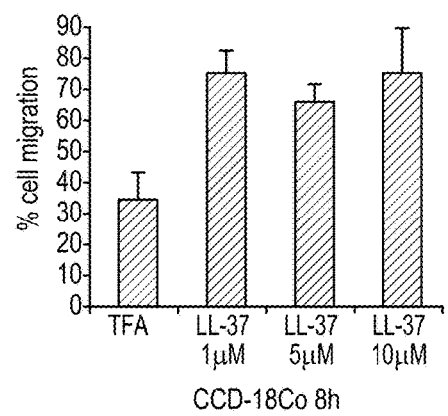
Figure 9C:
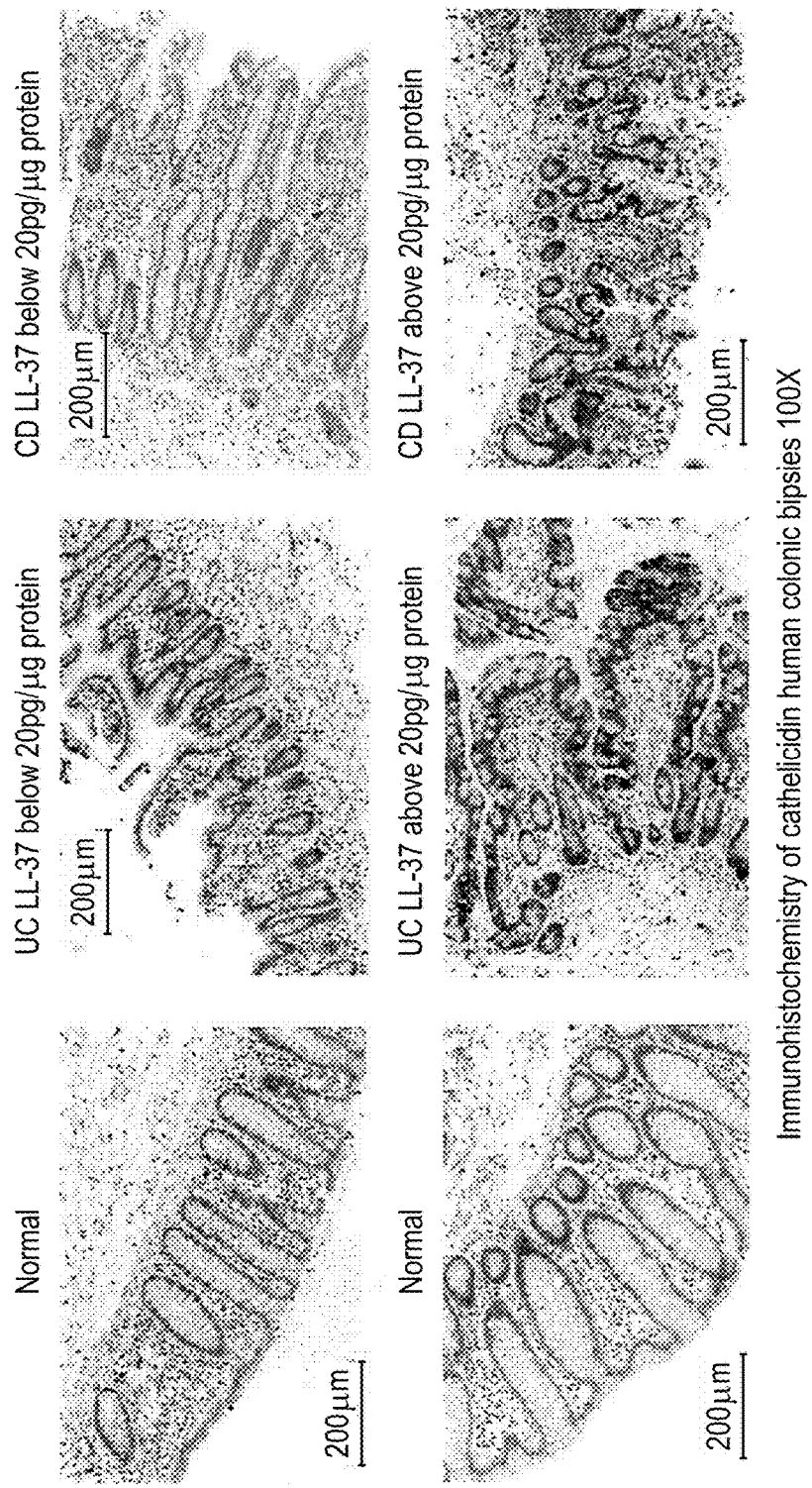
Figures 10B, 10C:
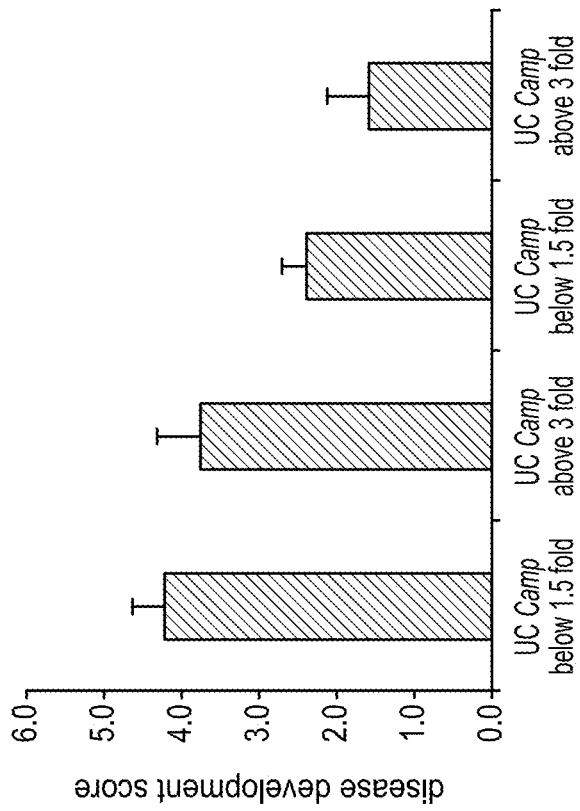

Inflammatory bowel disease patients are broadly classified into ulcerative colitis and Crohn's disease. Ulcerative colitis is a diffuse, non-specific inflammation of unknown etiology that affects the colon, and mainly invades the mucosal membrane and frequently causes erosion and ulcers. Normally, it presents with bloody diarrhea and various degrees of general symptoms. In general, it is categorized according to the spread of symptoms (pancolitis, left-sided colitis, proctitis or right-sided or segmental colitis), disease phase (such as an active phase or remission phase), severity (mild, moderate, severe) or clinical course (relapse-remission type, chronic sustained type, acute fulminant type or initial attack type). On the other hand, Crohn's disease is a disease in which granulomatous lesions accompanied by ulceration and fibrosis occur discontinuously throughout the digestive tract from the oral cavity to the anus. Although varying according to the site and range of the lesions, symptoms include fever, nutritional disorders and anemia, and systemic complications can also occur such as arthritis, iritis or liver disorders. In general, this disease is categorized according to, for example, the location of the lesions (small intestine type, small intestine-large intestine type, rectum type or gastroduodenal type) or the disease phase (such as an active phase or inactive phase).

In cases in which the occurrence of either ulcerative colitis or Crohn's disease is suspected on the basis of clinical symptoms, diagnosis is made on the basis of whether or not characteristic lesions are observed. Consequently, in making a diagnosis and determining the course of treatment of these diseases, endoscopic examination plays an important role since it allows direct observation of affected areas while also enabling histopathological examination. However, in cases of endoscopic examinations performed on critical patients, the examination itself may actually cause exacerbation. In addition, there is increasing reluctance to perform endoscopic examinations on the growing number of pediatric patients due to the highly invasive nature of the procedure and the need to perform the examination under anesthesia. Moreover, in order to observe the colon with an endoscope, preliminary treatment using laxatives and the like is required, and since this requires time, the level of acceptance to undergo an endoscopic examination among out-patients is not very high and it is difficult to perform the procedure easily. Consequently, there is a desire for an examination method that is less invasive and offers high sensitivity and specificity.

In addition, ulcerative colitis and Crohn's disease have unknown causes, there is no fundamental therapy and it is difficult to achieve a complete cure. Consequently, there is repeated relapse and remission, thereby considerably impairing patient quality of life. Thus, in these diseases, it is important to prolong the remission phase as long as possible and implement treatment promptly when relapse has occurred. In order to accomplish this as well, there is a strong desire for a non-invasive indicator that is effective for predicting disease activity and relapse.

Inflammatory bowel diseases (IBD), including, but not limited to Crohn's disease (CD) and ulcerative colitis (UC), are chronic intestinal disorders that affect approximately 3.4 million people in Western countries alone and result in enormous suffering and health-care costs. IBDs are heterogeneous diseases characterized by various genetic abnormalities that lead to overly aggressive inflammatory responses to a subset of commensal enteric bacteria. In clinical practice, 20 to 30% of patients with IBD colitis cannot be classified as CD or UC based upon usual endoscopic, radiologic, and histopathologic criteria, though this distinction may be crucial to guide therapeutic choices, especially when colonic resection is discussed.

IBD is a chronic and remitting disease causing inflammation of the intestinal diseases. UC and CD have symptoms and pathologies in common, but they differ in the severity and location of the inflammation along the intestinal tract. Inflammation in UC patients is limited to the mucosal layer, and involves only the rectum and colon, while inflammation in CD patients penetrates the entire wall of the intestine and can occur anywhere along the intestinal tract. A clear diagnosis of the type of IBD is crucial to treatment decisions.

Specifically, ulcerative colitis is a chronic inflammatory disease of the colon of unknown etiology. Ulcerative colitis often involves the lower part of the colon and the rectum and mucosal inflammation may extend to the caecum in a contiguous pattern. In its acute stages it resembles an infectious disease, but no microorganism has been definitively established as its cause. The disease causes inflammations of the mucosa of the colon, with extension to the submucosa in severe cases. Typically, not only the colon, but also the rectum is attacked, but only rarely is the ileum involved. The ulcer formation and its extent vary with the developmental stage of the disease, but can often be determined macroscopically (sigmoidoscopy and colonoscopy).

The related disease, Crohn's disease, also known as regional enteritis or colitis granulomatosa, is most frequently located in the small intestine (small bowel), especially in the ileum, but may also affect the jejunum and any part of the colon, including the rectum. Crohn's disease can affect all parts of the digestive tract and specially the ileum and/or colon and leads to mucosal ulcerations, fistula, and deep infiltration of inflammatory cells in the bowel wall. In the latter case the differentiation of Crohn's disease from ulcerative colitis gives rise to great diagnostic problems. Generally, the inflammation differs from that of ulcerative colitis by progressing to layers deeper than the mucosa and affecting the epithelium to a lesser degree.

Both diseases have become increasingly frequent especially in the developed countries. In the United States, the incidence of the ulcerative colitis is 5-15 cases per 100,000 inhabitants, whereas the incidence is approximately 5 per 100,000 inhabitants in the case of Crohn's disease, the figures continue to increase. Therefore, treatment of IBD has become an important problem of modern medicine.

Cathelicidin (LL-37 in human and mCRAMP in mice) represents a family of endogenous anti-microbial peptides. Endogenous cathelicidin mCRAMP deficiency leads to worsened acute dextran sulfate (DSS) colitis in mice through its anti-inflammatory role in bone marrow-derived cells (Koon H W, Shih D Q, Chen J, Bakirtzi K, Hing T C, Law I, et al. Cathelicidin signaling via the Toll-like receptor protects against colitis in mice. Gastroenterology. 2011; 141(5):1852-63 e1-3). A recent report suggests that intracolonic administration of exogenous cathelicidin could reduce the severity of DSS mediated acute colitis in mice (Tai E K, Wu W K, Wang X J, Wong H P, Yu L, Li Z J, et al. Intrarectal administration of mCRAMP-encoding plasmid reverses exacerbated colitis in Cnlp(−/−) mice. Gene Ther. 2012). Furthermore, cathelicidins are effective at significantly reducing intestinal fibrosis and treat inflammatory bowel diseases. However, the molecular mechanism of cathelicidin mediated anti-inflammatory effects in inflammatory bowel disease, e.g. colitis and Crohn's disease, is not fully understood.

As disclosed herein, the protein level of colonic cathelicidin is associated with clinical disease activity in inflammatory bowel disease patients. Induction of endogenous cathelicidin by sodium butyrate administration significantly ameliorates dextran sulfate induced colitis in wild-type but not mCRAMP deficient mice. Mechanistically, it was found that cathelicidin modulates colonic inflammation at least in part through anti-inflammatory pathway and antibacterial effects. Thus, Cathelicidin specifically reduced lipopolysaccharide (LPS) induced TNFα expression in macrophages via Akt dependent pathway.

Inflammatory Bowel Disease (IBD) includes two disease states, ulcerative colitis (UC) and Crohn's disease (CD). Both represent chronic debilitating diseases with increasing morbidity in both developing and developed countries. There are several IBD disease markers, including serum C-reactive protein, fecal calproteclin and erythrocyte sedimentation rate indicating disease activity of IBD; however, their value as biomarkers predicting future disease development is controversial. Therefore, new IBD disease markers are still being actively sought and evaluated.

As described herein, colonic cathelicidin can predict relapse of UC within 2 years. It was found that UC patients with high cathelicidin level in colonic biopsies have significantly longer disease free period, less chance of repeated surgery, repeated IBD related hospitalizations and abnormal white blood cell count and anemia, compared to patients with low colonic cathelicidin level. The criteria described herein was used in the format of disease development score to evaluate the future disease development of UC in a 2 year time frame and it was found that high cathelicidin levels are significantly correlated to low disease development score. These pieces of evidence suggest that colonic cathelicidin levels can be used as a biomarker that predicts UC development and chance of relapse.

There is no previously well established IBD disease marker to predict the chance of relapse or future development of the disease. As described herein, the colonic cathelicidin protein level of UC and CD patients were measured by ELISA and then followed up their disease development in the ensuing 2 years. Disease development was quantitatively measured by a set of criteria including disease free period, count of IBD related surgery, count of IBD related hospitalization, abnormal white blood cell count and anemia. These criteria are used to form a disease development score (see attached FIG. 1 for definition). UC patients with high colonic cathelicidin level (LL-37 above 35 pg/ug protein) have significantly lower disease development score (~45%), compared to those with lower colonic cathelicidin level (LL-37 below 20 pg/ug protein). Thus, colonic cathelicidin protein level can predict the future prognosis of UC patients for up to 2 years.

There is no prior report showing any correlation of colonic cathelicidin levels and UC development, although increased colonic cathelicidin mRNA expression in UC patients has been reported. Colonic cathelicidin can predict UC prognosis for about 2 years. Accordingly, the embodiments of the inventions described herein provide a novel discoveries for the treatment and diagnosis of inflammatory bowel diseases, e.g. ulcerative colitis.

In certain embodiments described herein, the methods and kits of this invention can be used to diagnose, treat, and prevent an inflammatory disease.

Inflammation is part of the complex biological response of vascular tissues to harmful stimuli, such as pathogens, damaged cells, or irritants. Inflammation is a protective attempt by the organism to remove the injurious stimuli and to initiate the healing process. Without inflammation, wounds and infections would never heal. Similarly, progressive destruction of the tissue would compromise the survival of the organism. However, chronic inflammation can also lead to a host of diseases, such as hay fever, periodontitis, atherosclerosis, rheumatoid arthritis, and even cancer (e.g., gallbladder carcinoma). It is for that reason that inflammation is normally closely regulated by the body.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

T-cells are involved in the promulgation of inflammation. Differentiation of naive T cells leads to the generation of T-cell subsets, each possessing distinct cytokine expression profiles for serving different immune functions. Through the activation of separate signaling pathways, this process results in both differentiated helper T (Th) cells, termed Th1, Th2 and Th17, and induced regulatory T cells, which suppress Th cells. These different cells are important for combating infectious diseases and cancers; however, when aberrant, they can be responsible for chronic inflammatory diseases. One such disease is inflammatory bowel disease (IBD), in which each T-cell subset can have a role in disease.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells Inhibition of angiogenesis by the pharmaceutical formulations of the present invention should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract Crohn's disease is an inflammatory bowel disease (IBD). Crohn's disease causes inflammation of the lining of a patient's digestive tract. The inflammation caused by Crohn's disease can be located through the digestive tract and the precise location(s) of the inflammation are patient-specific. For example, the inflammation can occur in the small intestines (e.g., the ileum), the large intestines (e.g., the colon), or the bowel wall (e.g., resulting in stenosis or fistula). In some patients the inflammation is isolated to one area of the digestive tract while in other patients the inflammation is present in two or more areas of the digestive tract.

This inflammation caused by Crohn's disease leads to abdominal pain, diarrhea, bloody stool, ulcers, reduced appetite, weight loss, fever, fatigue, arthritis, eye inflammation, mouth sores, skin disorders, inflammation of the liver or bile ducts, delayed growth or sexual development in children, and malnutrition. While these symptoms may not be present when the disease is in periods of remission, when the disease is active the symptoms can become debilitating and even life-threatening when disease-associated complications arise.

Furthermore, there are multiple disease-related complications that occur in patients with Crohn's disease. For example, because Crohn's disease affects the thickness of the intestinal wall and overtime the bowel can thicken, narrow, and eventually cause a bowel instruction. The chronic inflammation of Crohn's disease may also lead to ulcers throughout the digestive tract. Fistulas can also form when ulcers extend completely through the intestinal wall which can become infected and abscess. Perianal and anal fissures can also occur as a result of the chronic inflammation of Crohn's disease. Malnutrition and anemia can also be caused by diarrhea, loss of appetite, and inability to absorb nutrients. Furthermore, the chronic inflammation to the colon can increase the risk of a patient developing colon cancer.

In addition, Crohn's disease can also cause complications outside of the digestive tract. For example, Crohn's disease may cause arthritis, inflammation of the eyes or skin, clubbing of the fingernails, kidney stones, gallstones, inflammation of the bile ducts, and osteoporosis.

Risk factors for Crohn's disease may include age, ethnicity, family history, cigarette smoking, and environmental factors (e.g., pollution and diets high in fat or refined foods). Most patients who develop Crohn's disease are diagnosed as children or young adults, i.e., before they are 30 years old. Furthermore, because there is a genetic component and predisposition to Crohn's disease as described herein, patients are at an increased risk of developing the disease if they have a family member who is also afflicted with the condition.

There is no cure for Crohn's disease and treatment efficacy is patient dependent. The goal of treatment is to reduce the inflammation that triggers the symptoms, limit disease-related complications, and improve long-term prognosis. Because treatment regimes vary based on an individual patient's responsiveness, treatment plans often include anti-inflammatory drugs (e.g., sufasalazine, mesalamine, and corticosteroids), immune system suppressors (e.g., azathioprine, mercaptopurine, infliximab, adalimumab, certolizumab pegol, methodtrexate, cyclosporine, and natalizumab), antibiotics (e.g., metronidazol and ciprofloxacin), anti-diarrheals, laxatives, pain relievers, iron supplements, nutritional plan, vitamin B-12 shots, 6-thiopurine therapy, and surgery. However, many of these treatment regimes have their own side effects. For example, immune system suppressors are associated with an increased risk of developing cancer such as lymphoma.

Accordingly, because Crohn's disease is a lifelong, chronic disease that often presents symptoms in adolescents, there is a need to develop targeted therapies to treat the disease and minimize or eliminate unnecessary therapies that have detrimental side effects.

Inflammatory bowel disease patients are broadly classified into ulcerative colitis and Crohn's disease. Ulcerative colitis is a diffuse, non-specific inflammation of unknown etiology that affects the colon, and mainly invades the mucosal membrane and frequently causes erosion and ulcers. Normally, it presents with bloody diarrhea and various degrees of general symptoms. In general, it is categorized according to the spread of symptoms (pancolitis, left-sided colitis, proctitis or right-sided or segmental colitis), disease phase (such as an active phase or remission phase), severity (mild, moderate, severe) or clinical course (relapse-remission type, chronic sustained type, acute fulminant type or initial attack type). On the other hand, Crohn's disease is a disease in which granulomatous lesions accompanied by ulceration and fibrosis occur discontinuously throughout the digestive tract from the oral cavity to the anus. Although varying according to the site and range of the lesions, symptoms include fever, nutritional disorders and anemia, and systemic complications can also occur such as arthritis, iritis or liver disorders. In general, this disease is categorized according to, for example, the location of the lesions (small intestine type, small intestine-large intestine type, rectum type or gastroduodenal type) or the disease phase (such as an active phase or inactive phase).

In cases in which the occurrence of either ulcerative colitis or Crohn's disease is suspected on the basis of clinical symptoms, diagnosis is made on the basis of whether or not characteristic lesions are observed. Consequently, in making a diagnosis and determining the course of treatment of these diseases, endoscopic examination plays an important role since it allows direct observation of affected areas while also enabling histopathological examination. However, in cases of endoscopic examinations performed on critical patients, the examination itself may actually cause exacerbation. In addition, there is increasing reluctance to perform endoscopic examinations on the growing number of pediatric patients due to the highly invasive nature of the procedure and the need to perform the examination under anesthesia. Moreover, in order to observe the colon with an endoscope, preliminary treatment using laxatives and the like is required, and since this requires time, the level of acceptance to undergo an endoscopic examination among out-patients is not very high and it is difficult to perform the procedure easily. Consequently, there is a desire for an examination method that is less invasive and offers high sensitivity and specificity.

In addition, ulcerative colitis and Crohn's disease have unknown causes, there is no fundamental therapy and it is difficult to achieve a complete cure. Consequently, there is repeated relapse and remission, thereby considerably impairing patient quality of life. Thus, in these diseases, it is important to prolong the remission phase as long as possible and implement treatment promptly when relapse has occurred. In order to accomplish this as well, there is a strong desire for a non-invasive indicator that is effective for predicting disease activity and relapse.

Definitions

As used herein "chronic inflammatory disorder" or a "chronic inflammatory disease" may be defined herein as a disorder wherein at least one of the symptoms is chronic inflammation or wherein the disorder is caused at least in part by chronic inflammation. Chronic inflammation leads to a progressive shift in the type of cells which are present at the site of inflammation and involves destruction of the tissue from the inflammatory process.

Non-limiting examples of chronic inflammatory diseases include ileitis and inflammatory bowel disease (or "IBD"). In certain non-liming embodiments, the ileitis is Crohn's disease. In certain non-limiting embodiments, the inflammatory bowel disease is colitis. In certain non-limiting embodiments, the inflammatory bowel disease is ulcerative colitis (or "UC").

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "therapy," "therapeutic," "treating," "treat," "treatment," "treatment regimen," or "treatment regime" can be used interchangeably and refer broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and reducing or eliminating existing signs and/or symptoms. Therapy includes treating chronic disease ("maintenance") and acute disease. For example, treatment includes treating or preventing relapses or the recurrence of signs and/or symptoms (e.g., inflammation, pain).

Treatments include anti-inflammatory drugs (e.g., sufasalazine, mesalamine, NSAIDs, ImSAIDs, and corticosteroids), immune system suppressors (e.g., azathioprine, mercaptopurine, infliximab, adalimumab, certolizumab pegol, methodtrexate, cyclosporine, and natalizumab), antibiotics (e.g., metronidazol and ciprofloxacin), anti-diarrheals, laxatives, pain relievers, iron supplements, nutritional plan, vitamin B-12 shots, 6-thiopurine therapy, and surgery.

As used herein, the term "a pharmaceutical composition to increase the patient's cathelicidin protein levels" includes but is not limited to a cathelicidin peptide (e.g., LL-37), sodium butyrate, short chain fatty acids, vitamin D, PPAR gamma agonsits, lipopolysaccharides, Salmononella, and probiotics.

In certain embodiments the treatment regimen can include one or more of the above described treatments. In certain embodiments, the treatment regimen includes 1 or 2 or 3 or 4 or 5 or 6 or 7 or 8 or 9 or 10 or more of the above described treatments.

As used herein, "symptoms" of a disease refers broadly to any morbid phenomenon or departure from the normal in structure, function, or sensation, experienced by the patient and indicative of disease.

The term "conjugate" is used herein according to its broadest definition to mean joined or linked together. Molecules are "conjugated" when they act or operate as if joined.

As used herein, "solid support," "support," and "substrate" refer broadly to any material that provides a solid or semi-solid structure with which another material can be attached including but not limited to smooth supports (e.g., metal, glass, plastic, silicon, and ceramic surfaces) as well as textured and porous materials.

As used herein "diagnostic" refers broadly to identifying the presence or nature of a pathologic condition. Diagnostic methods differ in their sensitivity and specificity. The "sensitivity" of a diagnostic assay is the percentage of diseased individuals who test positive (percent of "true positives"). While a particular diagnostic method may not provide a definitive diagnosis of a condition, it suffices if the method provides a positive indication that aids in diagnosis.

As used herein, "diagnosing" refers broadly to classifying a disease or a symptom, determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

As used herein, "predisposition" or "predispose" refers to the increased likelihood or susceptibility of a patient acquiring or developing a disease. For example, it is known in the art that a patient with irritable bowel syndrome is predisposed to eventually developing Crohn's disease.

As used herein, "immunoassay" refers broadly to an assay that uses an antibody to specifically bind an antigen. The immunoassay may be characterized by the use of specific binding properties of a particular antibody to isolate, target, and/or quantify the antigen. Non-limiting examples of an immunoassay described herein include ELISA assays, FACS assays, Western blot assays, immunohistochemistry assays, and RT-PCR assays.

As used herein, "patient" or "subject" refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient." In preferred embodiments, a patient is a human.

Cathelicidin

In humans, there are several classes of known antimicrobial peptides (AMPS) including α-defensins, β-defensins, and cathelicidins. Cathelicidins are found in several mammalian species. Production of cathelicidins is induced in response to epithelial wounding or infectious challenge, or suppressed by the virulence mechanisms of certain bacterial pathogens. Cathelicidin expression is also differentially effected in certain chronic inflammatory disorders and the therapeutic benefits of cathelicidin have been demonstrated experimentally as described herein.

Cathelicidin proteins are composed of two distinct domains: an N-terminal "cathelin-like" or "prosequence" domain and the C-terminal domain of the mature AMP. The C-terminal domains of cathelicidins were among the earliest mammalian AMPs to show potent, rapid, and broad-spectrum killing activity. The term "cathelin-like" derives from the similarity of the N-terminal sequence with that of cathelin, a 12 kDa protein isolated from porcine neutrophils that shares similarity with the cystatin superfamily of cysteine protease inhibitors.

Cathelicidins are expressed in neutrophils and myeloid bone marrow cells and most epithelial sources, and were the first AMPs discovered in mammalian skin due to their presence in wound fluid. In the neutrophil, cathelicidins are synthesized as full-length precursor and targeted to the secondary granules where they are stored. Upon stimulation, the full-length cathelicidin protein is proteolytically processed to unleash the microbicidal activity of the C-terminal peptide from the cathelin-like domain.

The C-terminal 37 amino acids of human cathelicidin ("LL-37"; amino acid sequence LLGDFFRKSKEKIG-KEFKRIVQRIKDFLRNLVPRTES) has been characterized. LL-37 was originally referred to as FALL39, named for the first 4 N-terminal amino acids of this domain and the total number of residues (i.e., 39). LL-37 is a peptide predicted to contain an amphipathic alpha helix and lacks cysteine, making it different from all other previously isolated human peptide antibiotics of the defensin family, each of which contain 3 disulfide bridges. Full length human cathelicidin (i.e., full length LL-37) comprises the cathelin-like precursor protein and the C-terminal LL-37 peptide, thus comprising 170 amino acids.

Antimicrobial peptides are effector molecules of the innate immune system, which serve to protect the host against potentially harmful microorganisms. They are conserved through evolution and are widespread in nature. In human, only a handful has been identified so far; among which the defensins and the human cathelicidin antimicrobial peptide hCAP 18 have been implicated in epithelial defense (Selsted et al., J Biol Chem 258:14485-14489, 1983).

The proprotein was named hCAP18, human cationic anti-microbial protein, and is a member of the cathelicidin family of proteins consisting of cathelin, which has been conserved through evolution and a C-terminal part, variable in different species. In man, hCAP 18 is the only member of this protein family, whereas in other species, such as mouse and pig, there are several members. The C-terminal peptide LL-37 is thought to function extracellularly and there is no evidence for intracellular cleavage of the proprotein. hCAP18/LL-37 is present in leukocytes and in barrier organs such as skin, mucous membranes, respiratory epithelium and reproductive organs. The localization of hCAP18/LL-37 to barrier epithelia seems to be consistent with a protective role for the peptide in preventing local infection and systemic microbial invasion. LL-37 is described as a cysteine-free peptide that can adopt an amphipatic, or in other words amphiphilic, α-helical conformation. A high cationicity in combination with a stabilized amphipatic α-helical structure seems to be required for the anti-microbial effect of such peptides against gram-positive bacteria and fungi, as has been shown experimentally (Gianga-spero et al., Eur J Biochem 268:5589-5600, 2001). The amphipatic and α-helical structure seems to be less critical for killing of gram-negative bacteria. In association with inflammation hCAP18/LL-37 is upregulated in skin epithelium (Frohm et al., J Biol Chem 272:15258-15263, 1997) and mucous membranes (Frohm Nilsson et al., Infect Immun 67:2561-2566, 1999).

As described herein, cathelicidins are effective at significantly reducing intestinal fibrosis and treat inflammatory bowel diseases. In specific embodiments cathelicidin can be administered in a peptide form intracolonically or in a lientiviral expressing vector intravenously to mediate its anti-fibrogenic effects.

As described herein, cathelicidin significantly reduces TGF-b1 and IGF-1 induced collagen COL1A2 protein and mRNA expression in human colonic CCD-18Co fibroblasts. In specific embodiments 10 uM calthelicidin (LL-37 10 uM) significantly reduces TGF-b1 and IGF-1 induced collagen COL1A2 protein and mRNA expression in human colonic CCD-18Co fibroblasts. Cathelicidin (LL-37 10 uM) significantly induces ERK phosphorylation in human colonic CCD-18Co fibroblasts. Cathelicidin (mCRAMP 5 mg/kg) intracolonically significantly reduces TNBS induced intestinal fibrosis. Cathelicidin (mCRAMP expressing lentivirus 5 ng/mouse) intravenously significantly reduces TNBS induced intestinal fibrosis.

In specific embodiments, 1 uM, 2 uM, 3 uM, 4 uM, 5 uM, 6 uM, 7 uM, 8 uM, 9 uM, 10 uM, 11 uM, 12 uM, 13 uM, 14 uM, 15 uM, 16 uM, 17 uM, 18 uM, 19 uM, 20 uM, 21 uM, 22 uM, 23 uM, 24 uM, 25 uM, 26 uM, 27 uM, 28 uM, 29 uM, or 30 uM cathelicidin is administered to reduces TGF-b1 and IGF-1 induced collagen COL1A2 protein and mRNA expression in human colonic CCD-18Co fibroblasts. In specific embodiments, 35 uM, 40 uM, 45 uM, 50 uM, 55 uM, 60 uM, 70 uM, 75 uM, 80 uM, 85 uM, 90 uM, 95 uM, or 1 mM or more reduces TGF-b1 and IGF-1 induced collagen COL1A2 protein and mRNA expression in human colonic CCD-18Co fibroblasts.

In certain embodiments, cathelicidin (LL-37 and mCRAMP) peptide may be administered to patients with Crohn's disease via intracolonic administration (e.g., administered with an enema). In certain embodiments, cathelicidin (LL-37 and mCRAMP) peptide may be administered to patients with ulcerative colitis via intracolonic administration (e.g., administered with an enema). In certain embodiments, cathelicidin (LL-37 and mCRAMP) peptide may be administered to patients with a broad range of inflammatory bowel diseases via intracolonic administration (e.g., administered with an enema).

In certain embodiments, cathelicidin (LL-37 and mCRAMP) expressing lentivirus may be administered to patients with Crohn's disease via intravenous administration. In certain embodiments, cathelicidin (LL-37 and mCRAMP) expressing lentivirus may be administered to patients with ulcerative colitis via intravenous administration. In certain embodiments, cathelicidin (LL-37 and mCRAMP) expressing lentivirus may be administered to patients with inflammatory bowel disease via intravenous administration.

In certain embodiments, cathelicidin (LL-37 and mCRAMP) expressing lactobacilli may be administered to patients with Crohn's disease via oral administration. In certain embodiments, cathelicidin (LL-37 and mCRAMP) expressing lactobacilli may be administered to patients with ulcerative colitis via oral administration. In certain embodiments, cathelicidin (LL-37 and mCRAMP) expressing lactobacilli may be administered to patients with inflammatory bowel disease via oral administration.

In certain embodiments, cathelicidin may be modified. In specific embodiments, one or more amino acids of the cathelicidin protein can be substituted. In specific embodiments, one or more amino acids of the cathelicidin protein can be deleted. In specific embodiments, one or more amino acids can be added to the native cathelicidin protein. In specific embodiments, 1, 2, 3, 4, 5, 6, 7, 8, 9, or 10 or more amino acids of the cathelicidin protein can be substituted, deleted, or added.

In certain embodiments, artificially modified cathelicidin with increased stability may be administered to patients with Crohn's disease. In certain embodiments, artificially modified cathelicidin with increased stability may be administered to patients with ulcerative colitis. In certain embodiments, artificially modified cathelicidin with increased stability may be administered to patients with inflammatory bowel disease. In specific embodiments, the artificially modified cathelicidin can be administered via intracolonic administration, via intravenous administration, or via oral administration.

In certain embodiments, induction of endogenous cathelicidin expression via histone deacetylase inhibitors such as sodium butyrate, trichostatin A, valproic acid or equivalents via oral, intravenous or intracolonic administration may be used. In certain embodiments, consumption of high fiber diet may indirect promote conversion of fiber into short chain fatty acid including butyrate by gut bacteria. Such short chain fatty acid may induce endogenous cathelicidin in the gut that in turn inhibits Crohn's disease associated fibrosis.

In certain embodiments, modified cathelicidin can be administered to a patient and exert anti-fibrogenic effects. For example, cathelicidin (LL-37 and mCRAMP) peptide or artificially modified cathelicidin can be used to treat patients with Crohn's disease. For example, cathelicidin (LL-37 and mCRAMP) peptide or artificially modified cathelicidin can be used to treat patients with Crohn's disease who develop fibrosis. For example, cathelicidin (LL-37 and mCRAMP) peptide or artificially modified cathelicidin can be used to treat patients with ulcerative colitis who develop fibrosis. For example, cathelicidin (LL-37 and mCRAMP) peptide or artificially modified cathelicidin can be used to treat patients with inflammatory bowel disease, particularly patients with inflammatory bowel disease who develop fibrosis.

In certain embodiments, cathelicidin (LL-37 and mCRAMP) peptide or artificially modified cathelicidin can be expressed in bacterium. Specifically, cathelicidin (LL-37 and mCRAMP) peptide or artificially modified cathelicidin can be expressed in lactobacilli.

Inflammatory Bowel Disease Marker

As described herein, colonic biopsies were obtained from the actively inflamed sections of the colons by colonoscopy to determine inflammatory bowel disease biomarkers. Specifically, cathelicidin was measured by a commercially available ELISA. Disease development scores were calculated by a point system based on the disease free period, count of IBD related surgery, count of hospitalization since the biopsies taking, WBC count and hemoglobin level in blood measured within a 2 years follow-up period after the initial biopsy is obtained. High colonic cathelicidln levels are correlated to lower disease development score among UC patients. It means better prognosis in the upcoming 2 years after the biopsy is taken.

In specific embodiments, biopsies were obtained from the inflamed section of UC patients. Multiple biopsy per patients were taken when possible for accurate evaluation. Measurements of cathelicidin LL-37 protein were taken by ELISA. If LL-37 levels were higher than 35 pg/ug protein, patients had a good prognosis of UC. If LL-37 levels were lower than 20 pg/ug protein, patients had a bad prognosis of UC.

In some embodiments, serum LL-37 levels can be correlated to inflammatory bowel disease development. In specific embodiments, serum LL-37 levels can be correlated to ulcerative colitis development. In specific embodiments, serum LL-37 levels can be correlated to Crohn's disease development. In some embodiments, inflammatory bowel disease progression can be measured by taking measurements of the cathelicidin LL-37 protein. In specific embodiments, Crohn's disease progression can be measured by taking measurements of the cathelicidin LL-37 protein. In specific embodiments, ulcerative colitis progression can be measured by taking measurements of the cathelicidin LL-37 protein.

In one aspect, provided herein is a method of diagnosing inflammatory bowel disease activity. The method includes detecting cathelicidin protein expression levels using a probe (e.g., an antibody) that specifically binds cathelicidin in a biological sample from a patient. In some embodiments, the inflammatory bowel disease is ulcerative colitis (UC). Ulcerative colitis activity can be measured using suitable method. In some embodiments, ulcerative colitis activity is measured using a partial Mayo score (see, e.g., Lewis et al. *Inflamm Bowel Dis.* 14(12): 1660-1666 (2008), which is incorporated herein by reference). In exemplary embodiments, the biological sample is a blood sample. As described herein, low serum cathelicidin protein expression levels is indicative of moderate or active UC (partial Mayo score 5-8), whereas high serum cathelicidin protein expression levels is indicative of UC remission (partial Mayo score 0-2).

In some embodiments, a low cathelicidin protein expression level in the blood sample is indicative of moderate or active UC (e.g., partial Mayo score 5-8). In certain embodiments, the low cathelicidin protein expression level is 50 ng/ml or lower, 49 ng/ml or lower, 48 ng/ml or lower, 47 ng/ml or lower, 46 ng/ml or lower, 45 ng/ml or lower, 44 ng/ml or lower, 43 ng/ml or lower, 42 ng/ml or lower, 41 ng/ml or lower, 40 ng/ml or lower, 39 ng/ml or lower, 38 ng/ml or lower, 37 ng/ml or lower, 36 ng/ml or lower, or 35 ng/ml or lower. In exemplary embodiments, the low cathelicidin protein expression level is 40 ng/ml or lower.

In some embodiments, a high cathelicidin protein expression level is indicative of an UC that is in remission in the patient (e.g., partial Mayo score 0-2). In some embodiments, the high cathelicidin protein expression level is 40 ng/ml or greater, 41 ng/ml or greater, 42 ng/ml or greater, 43 ng/ml or greater, 44 ng/ml or greater, 45 ng/ml or greater, 46 ng/ml or greater, 47 ng/ml or greater, 48 ng/ml or greater, 49 ng/ml or greater, 50 ng/ml or greater, 51 ng/ml or greater, 52 ng/ml or greater, 53 ng/ml or greater, 54 ng/ml or greater, or 55 ng/ml or greater. In certain embodiments, the high cathelicidin protein expression level is 54 ng/ml or greater.

In some embodiments, the inflammatory bowel disease is Crohn's disease. In some embodiments, the biological sample is a blood sample. In some embodiments, a low cathelicidin protein expression level is indicative that the patient has stricture associated with Crohn's disease. In some embodiments, a high cathelicidin protein expression level is indicative that the patient does not have stricture associated with Crohn's disease. As described herein, low serum cathelicidin protein expression levels are indicative of strictured CD patients, whereas high serum cathelicidin protein expression levels are indicative of non-strictured CD patients.

In some embodiments, the low cathelicidin protein expression level indicative of strictured CD is 50 ng/ml or lower, 49 ng/ml or lower, 48 ng/ml or lower, 47 ng/ml or lower, 46 ng/ml or lower, 45 ng/ml or lower, 44 ng/ml or lower, 43 ng/ml or lower, 42 ng/ml or lower, 41 ng/ml or lower, 40 ng/ml or lower, 39 ng/ml or lower, 38 ng/ml or lower, 37 ng/ml or lower, 36 ng/ml or lower, or 35 ng/ml or lower. In certain embodiments, the low cathelicidin protein expression level is 45 ng/ml or lower.

In some embodiments, the high cathelicidin protein expression level indicative of non-strictured CD is 65 ng/ml or greater, 66 ng/ml or greater, 67 ng/ml or greater, 68 ng/ml or greater, 69 ng/ml or greater, 70 ng/ml or greater, 71 ng/ml or greater, 72 ng/ml or greater, 73 ng/ml or greater, 74 ng/ml or greater, 75 ng/ml or greater, 76 ng/ml or greater, 77 ng/ml or greater, 78 ng/ml or greater, 79 ng/ml or greater, or 80 ng/ml or greater. In certain embodiments, the high cathelicidin protein expression level is 75 ng/ml or greater.

In another aspect, provided herein is a method for detecting an active inflammatory bowel disease in a patient. In an exemplary embodiment, the method includes the step of detecting cathelicidin protein levels and C-reactive protein (CRP) levels in a biological sample from the patient, wherein low levels of cathelicidin protein and high CRP levels are indicative of an active inflammatory bowel disease. As described herein, the combination of low levels of cathelicidin protein expression and high levels of CRP protein expression is indicative of active inflammatory bowel disease (e.g., ulcerative colitis having a partial Mayo score of 5-8). Without being bound by any particular theory of operation, it is believed that the combination of cathelicidin and CRP protein expression levels is a more accurate indicator of active ulcerative colitis than the expression levels of each of these biomarkers taken individually. In some embodiments, the cathelicidin protein levels are LL-37 peptide levels. In certain embodiments, the inflammatory bowel disease is ulcerative colitis (UC). In some embodiments, the cathelicidin protein levels and CRP protein levels are serum cathelicidin protein levels and serum CRP protein levels. In certain embodiments, the patient has active ulcerative colitis if the patient has a serum cathelicidin protein level of 55 ng/ml or below and a serum CRP level of 2 mg/L or above. In exemplary embodiments, the biological sample is a blood sample. In some embodiments, the serum cathelicidin protein level is 60 ng/ml or below, 59 ng/ml or below, 58 ng/ml or below, 57 ng/ml or below, 56 ng/ml or below, 55 ng/ml or below, 54 ng/ml or below, 53 ng/ml or below, 52 ng/ml or below, 51 ng/ml or below, 50 ng/ml or below, 49 ng/ml or below, 48 ng/ml or below, 47 ng/ml or below, 46 ng/ml or below, or 45 ng/ml or below. In some embodiments, the CRP level is 1 mg/L or above, 2 mg/L or above, 3 mg/L or above, 4 mg/L or above, 5 mg/L or above, 6 mg/L or above, 7 mg/L or above, 8 mg/L or above, 9 mg/L or above, or 10 mg/L or above.

In some embodiments, the cathelicidin protein levels and CRP protein levels are detected using a cathelicidin binding probe and a CRP binding probe. In certain embodiments, the cathelicidin binding probe is an antibody that binds cathelicidin and the CRP binding probe is an antibody that binds CRP. In some embodiments, the cathelicidin binding probe and the CRP binding probe are attached to a solid support. In certain embodiments, the cathelicidin and CRP protein levels are detected by ELISA. In other embodiments, the cathelicidin protein levels are detected by assay selected from the group consisting of FACS, Western blot, and immunohistochemistry. In some embodiments, the patient is a human.

In another aspect, provided herein is an antibody cocktail that includes a plurality of antibodies and a buffer solution, where the plurality of antibodies includes an anti-CRP antibody and an anti-cathelicidin antibody. Such antibody cocktails that include such antibodies are useful, for example, for the methods of detection of IBD activity (e.g., ulcerative colitis) described herein.

As used herein, an "antibody" includes full length antibody and antibody fragments. As used herein, an "antibody fragment" refers to a polypeptide or polypeptides that include one or more portions of an antibody, Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546, entirely incorporated by reference) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883, entirely incorporated by reference), all entirely incorporated by reference). In some embodiments, the antibody fragment is modified. For example, the molecules may be stabilized by the incorporation of disulphide bridges linking the VH and VL domains (Reiter et al., 1996, Nature Biotech. 14:1239-1245, entirely incorporated by reference).

In some embodiments, the binding moiety is an scFv. By "scFv" herein is meant an artificial construct that links a variable heavy chain region (VH) and a variable light chain region (VL) of an antibody, generally linked as is well known in the art using flexible peptide linkers of glycine and serine, for example $Gly_4Ser$ or repeats thereof. An scFv is an antibody component in the context of the invention.

Any suitable buffer the antibodies and facilitates detection after the antibodies have bound to the antigen can be used. In certain embodiments, the anti-cathelicidin antibody binds LL-37. In exemplary embodiments, the antibodies in the plurality of antibodies are monoclonal antibodies.

Administration and Treatment Modalities

The cathelicidin polypeptides of the invention are administered to a subject, in accord with known methods, such as intracolonic, intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In certain aspects, thecathelicidin polypeptides are administered to a subject with an inflammatory bowel disease. In certain aspects, thecathelicidin polypeptides are administered to a subject with ulcerative colitis. In certain aspects, the cathelicidin polypeptides are administered to a subject with Crohn's disease.

In the methods of the invention, therapy is used to provide a positive therapeutic response with respect to a disease or condition. By "positive therapeutic response" is intended an improvement in the disease or condition, and/or an improvement in the symptoms associated with the disease or condition. For example, a positive therapeutic response would refer to one or more of the following improvements in the disease: (1) a reduction in inflammation; (2) a reduction in fibrosis; (3) inhibition of progressive inflammation; (5) inhibition of progressive fibrosis; (6) an increased patient survival rate; and (7) some relief from one or more symptoms associated with the disease or condition. Positive therapeutic responses in any given disease or condition can be determined by standardized response criteria specific to that disease or condition.

In addition to these positive therapeutic responses, the subject undergoing therapy may experience the beneficial effect of an improvement in the symptoms associated with the disease.

Treatment according to the present invention includes a "therapeutically effective amount" of the medicaments used. A "therapeutically effective amount" refers to an amount effective, at dosages and for periods of time necessary, to achieve a desired therapeutic result.

A therapeutically effective amount may vary according to factors such as the disease state, age, sex, and weight of the individual, and the ability of the medicaments to elicit a desired response in the individual. A therapeutically effective amount is also one in which any toxic or detrimental effects of the antibody or antibody portion are outweighed by the therapeutically beneficial effects. A "therapeutically effective amount" for treatment of an inflammatory bowel disease may also be measured by its ability to stabilize the progression of disease.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The efficient dosages and the dosage regimens for the cathelicidin polypeptides used in the present invention depend on the disease or condition to be treated and may be determined by the persons skilled in the art.

An exemplary, non-limiting range for a therapeutically effective amount of an cathelicidin polypeptides used in the present invention is about 0.1-100 mg/kg, such as about 0.1-50 mg/kg, for example about 0.1-20 mg/kg, such as about 0.1-10 mg/kg, for instance about 0.5, about such as 0.3, about 1, or about 3 mg/kg. In another embodiment, the antibody is administered in a dose of 1 mg/kg or more, such as a dose of from 1 to 20 mg/kg, e.g. a dose of from 5 to 20 mg/kg, e.g. a dose of 8 mg/kg. A second exemplary, non-limiting range for a therapeutically effective amount of an cathelicidin polypeptides used in the present invention is about 0.1-100 ug/kg, such as about 0.1-50 ug/kg, for example about 0.1-20 ug/kg, such as about 0.1-10 ug/kg, for instance about 0.5, about such as 0.3, about 1, or about 3 ug/kg. A third exemplary, non-limiting range for a therapeutically effective amount of an cathelicidin polypeptides used in the present invention is about 100-500 mg/kg, such as about 100-400 mg/kg, for example about 100-300 mg/kg, or such as about 100-300 mg/kg.

A medical professional having ordinary skill in the art may readily determine and prescribe the effective amount of the pharmaceutical composition required. For example, a physician or a veterinarian could start doses of the medicament employed in the pharmaceutical composition at levels lower than that required in order to achieve the desired therapeutic effect and gradually increase the dosage until the desired effect is achieved.

In one embodiment, the cathelicidin polypeptide is administered by infusion in a weekly dosage of from 1 to 500 mg/kg. In one embodiment, the cathelicidin polypeptide is administered intracolonically in a weekly dosage of from 1 to 500 mg/kg. Such administration may be repeated, e.g., 1 to 8 times, such as 3 to 5 times. Such administration may be repeated daily, weekly, or monthly.

In one embodiment the cathelicidin polypeptide is administered in a weekly dosage of from 250 mg to 2000 mg, such as for example 300 mg, 500 mg, 700 mg, 1000 mg, 1500 mg or 2000 mg, for up to 8 times, such as from 4 to 6 times. The administration may be performed by continuous infusion over a period of from 2 to 24 hours, such as from 2 to 12 hours. Such regimen may be repeated one or more times as necessary, for example, after 6 months or 12 months. The dosage may be determined or adjusted by measuring the amount of compound of the present invention in the blood upon administration.

In one embodiment, the cathelicidin polypeptides of this invention are conjugated to an imaging molecule for diagnostic tests. Specifically in one embodiment, the cathelicidin polypeptides of this invention are conjugated to an imaging molecule for the diagnosis of an inflammatory bowel disease. Specifically in one embodiment, the cathelicidin polypeptides of this invention are conjugated to an imaging molecule for the diagnosis of ulcerative colitis. Specifically in one embodiment, the cathelicidin polypeptides of this invention are conjugated to an imaging molecule for the diagnosis of Crohn's disease. In one embodiment, the cathelicidin polypeptides of this invention are conjugated to additional therapeutic molecules for the treatment of inflammatory bowel disease. Specifically, in one embodiment the cathelicidin polypeptides of this invention are conjugated to additional therapeutic molecules for the treatment of ulcerative colitis. Specifically, in one embodiment the cathelicidin polypeptides of this invention are conjugated to additional therapeutic molecules for the treatment of Crohn's disease.

In one embodiment, the cathelicidin polypeptides of this invention are administered in a combination therapy. In specific embodiments, the combination therapy comprises a cathelicidin polypeptide and an anti-inflammatory therapy. In certain embodiments, the anti-inflammatory drug is one or more of sufasalazine, mesalamine, NSAIDs, ImSAIDs, and corticosteroids), immune system suppressors (e.g., azathioprine, mercaptopurine, infliximab, adalimumab, certolizumab pegol, methotrexate, cyclosporine, and natalizumab), antibiotics (e.g., metronidazol and ciprofloxacin), anti-diarrheals, laxatives, pain relievers, iron supplements, nutritional plan, vitamin B-12 shots, thiopurine and thioguanine therapies (e.g., 6-thiopurine therapy, and surgery. In specific embodiments, a cathelicidin polypeptide may be administered in combination with a therapeutic TNFα agent. In specific embodiments, the TNFα agent is Infliximab®.

In specific embodiments, the combination therapy comprises one or more cathelicidin polypeptides and 1, 2, 3, 4, 5, 6, 7, 8, or 9 additional agents. In specific embodiments the combination treatment is administered such that the cathelicidin polypeptide(s) are administered at the same time as the second, third, fourth, fifth, sixth, seventh, eighth, ninth, or tenth agent. In specific embodiments the combination treatment is administered such that the cathelicidin polypeptide(s) are administered before the second, third, fourth, fifth, sixth, seventh, eighth, ninth, or tenth agent. In specific embodiments the combination treatment is administered such that the cathelicidin polypeptide(s) are administered after the second, third, fourth, fifth, sixth, seventh, eighth, ninth, or tenth agent. In certain embodiments, the second, third, fourth, fifth, sixth, seventh, eighth, ninth, or tenth agent is an agent that increases the cellular production of cathelicidin in vivo.

In specific embodiments, an agent that upregulates cellular cathelicidin in vivo is administered instead of a cathelicidin polypeptide.

In other embodiments, this disclosure relates to companion diagnostic methods and products. In one embodiment, the companion diagnostic method and products can be used to monitor the treatment of inflammatory bowel diseases, specifically ulcerative colitis or Crohn's disease, as described herein. In some embodiments, the companion diagnostic methods and products include molecular assays to measure levels of proteins, genes or specific genetic mutations. Such measurements can be used, for example, to predict whether the cathelicidin polypeptide therapy will benefit a specific individual, to predict the effective dosage of cathelicidin polypeptide therapy, to monitor cathelicidin polypeptide therapy, adjust cathelicidin polypeptide therapy, tailor the cathelicidin polypeptide therapy to an individual, and track the progression and remission of inflammation, fibrosis, and all other symptoms (as described herein and as would be known by one of skill in the art) of inflammatory bowel diseases.

In some embodiments, the companion diagnostic can be used to monitor a combination therapy.

In some embodiments, the companion diagnostic can include cathelicidin polypeptide described herein.

In some embodiments, the companion diagnostic can be used before, during, or after cathelicidin polypeptide therapy.

Articles of Manufacture

In other embodiments, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

Also within the scope of the invention are kits.

In certain embodiments, the kits contain necessary reagents and the method for diagnosis, monitoring or assessing chronic inflammatory disease (e.g., Crohn's disease) using an immunoassay such as an ELISA, a western blot, a protein array, a reverse phase protein array, a single cell barcode chip, flow cytometry, a single cell cytokine analysis assay, immunofluorescent staining, or any other means of detecting cytokine expression in cells known to one of skill in the art.

In certain embodiments the kit comprises probe(s), wherein the probe(s) are attached to a solid support. This solid support preferably comprises beads (more preferably, inmunobeads), a gel (e.g., agarose or polyacylamide gel), or any array-type solid matrix such as a slide made of distinct materials, such as glass with or without a gold-covered surface.

As described herein, the kits may include instructions, directions, labels, marketing information, warnings, or information pamphlets.

In another preferred embodiment, the probes are antibodies used to recognize the protein of the present invention, or a fragment thereof. The antibodies can be monoclonal or polyclonal.

In another preferred embodiment, the probes are used to recognize cathelicidln. In another preferred embodiment, the probes are used to recognize LL-37.

EXAMPLES

Human intestinal biopsies from normal and IBD patients, cathelicidin deficient (Camp$^{-/-}$) mice, human peripheral blood monocytes and mouse Raw264.7 macrophages were used. In UC patients (human clinical data), patients with intestinal LL-37 below 20 pg/µg protein level have significantly higher serum C-reactive protein (CRP) than those with intestinal LL-37 above 35 pg/µg protein level. In CD patients, patients with intestinal LL-37 below 20 pg/µg protein level have significantly higher erythrocyte sedimentation rate (ESR) than those with intestinal LL-37 above 35 pg/µg protein level. This finding indicates that cathelicidin level is inversely proportional to the disease activity of IBD patients. Also, plasma cathelicidin levels of UC but not CD patients were significantly decreased. (Mouse colitis model) Camp$^{-/-}$ mice developed more severe colitis than WT mice when exposed to DSS for 5 days. Sodium butyrate induced endogenous cathelicidin expression in colons that partially inhibited DSS mediated colitis in WT mice but not Camp$^{-/-}$ mice. (Mechanistic study) LPS induced TNFalpha secretion from Raw264.7 macrophages that was significantly reduced by cathelicidin via Akt dependent mechanism. Based on the experiments described herein, intestinal cathelicidin level represents a novel biomarker to indicate IBD disease activity. Sodium butyrate induced cathelicidin expression may represent a new therapeutic approach against colitis.

Example 1. Human Intestinal Biopsies and Blood Collection

Human intestinal biopsies were obtained from normal patients, UC patients and CD patients after informed consent in accordance with procedures established by the Cedars-Sinai Institutional Review Board, IRBs 3358 and 23705 and UCLA Institutional Review Board IRB 11-001527. Inclusion and exclusion criteria were listed in FIG. 12A. Baseline characteristics were outlined in FIG. 12B. Some fresh biopsies were frozen until homogenization. Some fresh colonic biopsies were cut into ~3×3 mm pieces and incubated in serum free DMEM with 1% penicillin/streptomycin (Invitrogen) and exposed to LPS and/or LL-37.

Human blood samples were collected from healthy normal patients, UC patients and CD patients after informed consent in accordance with procedures established by the UCLA. Inclusion criteria, exclusion criteria and baseline characteristics are outlined in FIG. 14A and FIG. 14B. Blood plasma samples were centrifuged by UCLA pathology department. The plasma samples were diluted by sample assay buffer 20× before loading into ELISA plates.

Example 2. Colonic LL-37 Protein Expression Indicates IBD Disease Activity

Figures 12C, 12D:
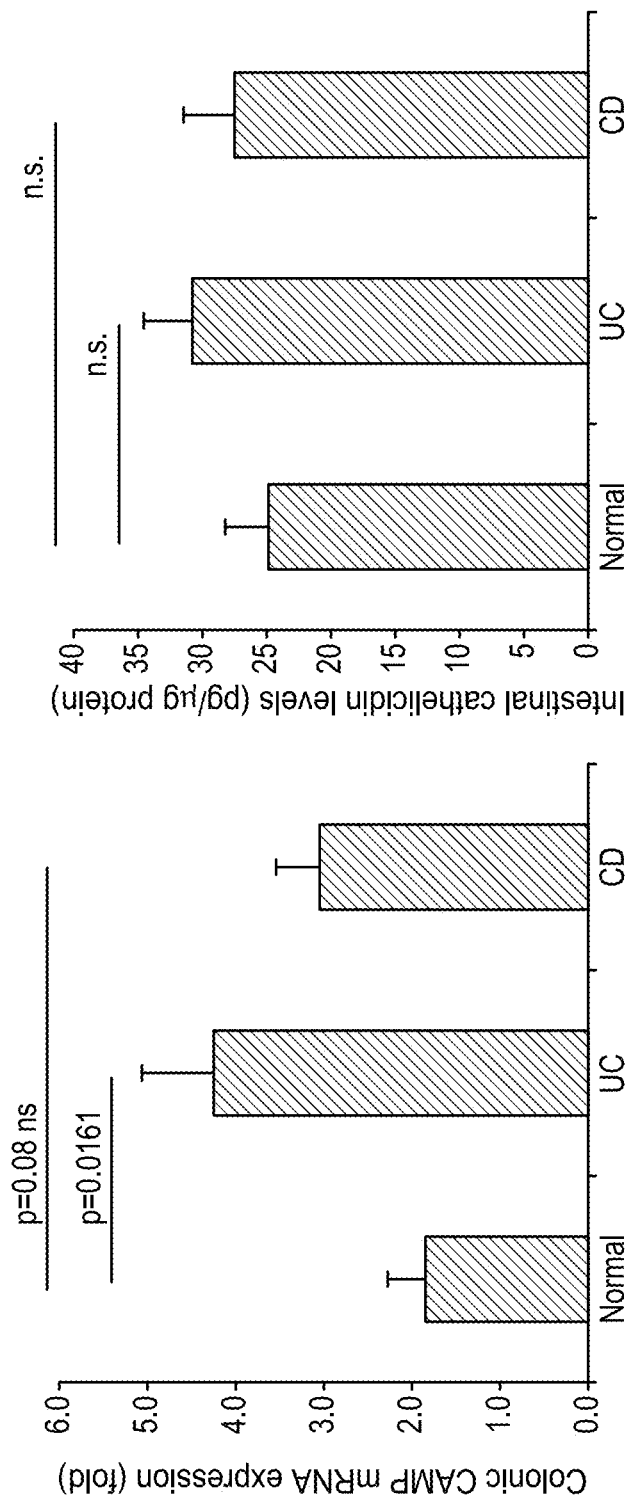
Figure 12E:
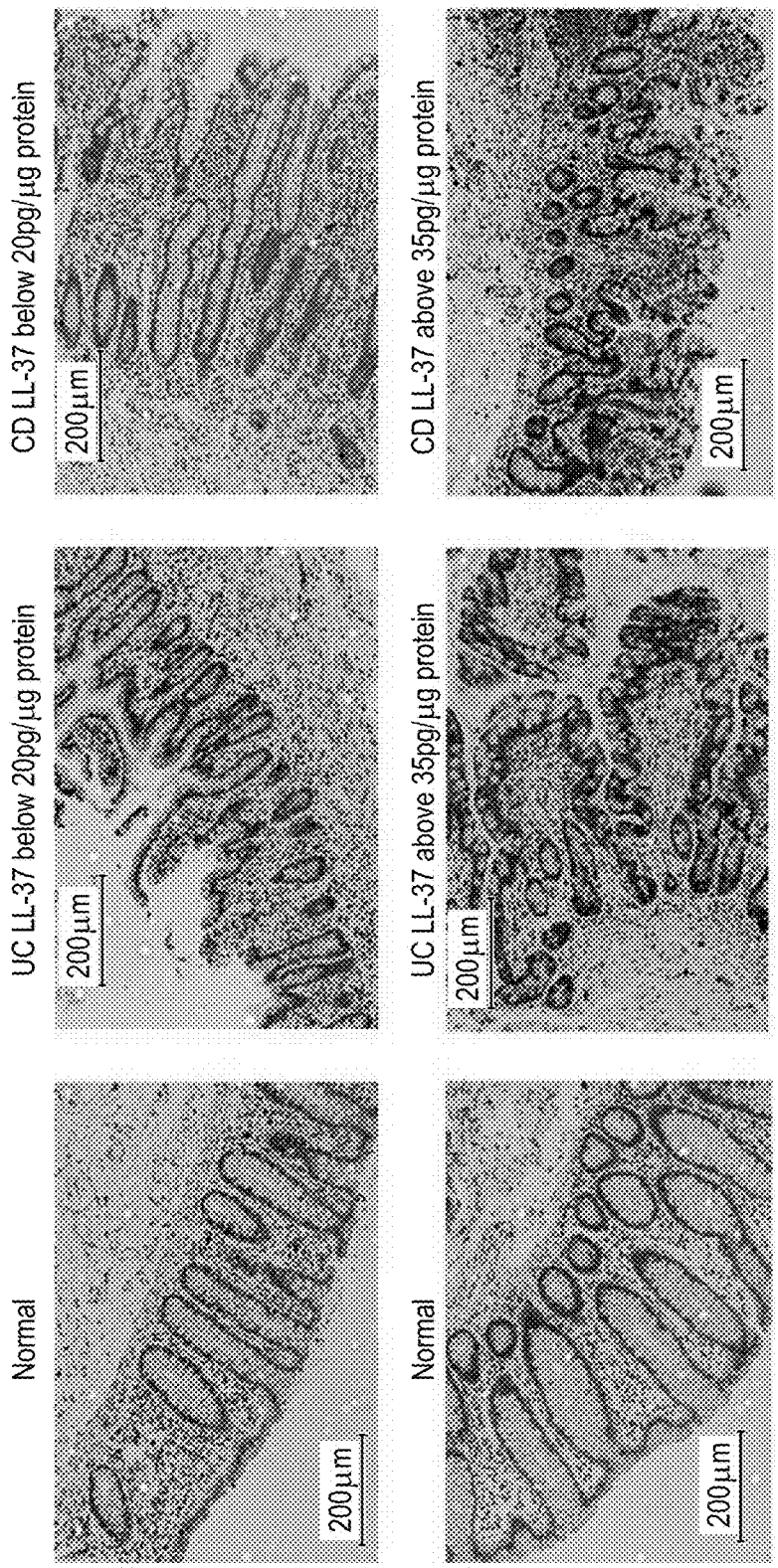

The colonic tissues of 40 normal, 52 UC and 52 CD patients were analyzed. Inclusion and exclusion criteria as well as baseline characteristics are shown in FIG. 12A and FIG. 12B. In agreement with a previous report (Schauber J, Rieger D, Weiler F, Wehkamp J, Eck M, Fellermann K, et al. Heterogeneous expression of human cathelicidin hCAP18/LL-37 in inflammatory bowel diseases. Eur J Gastroenterol Hepatol. 2006; 18(6):615-21), it was found that the colons of UC patients, but not the those of CD patients, had significantly higher mRNA expression than those of normal patients (FIG. 12C). Interestingly, average colonic LL-37 protein levels in both UC and CD patients were not significantly altered significantly higher than those of normal patients (FIG. 12D). As shown by immunohistochemistry, LL-37 protein was mainly expressed in colonic mucosa and sub-mucosa with large variation in expression intensity (FIG. 12E).

Figure 20B:
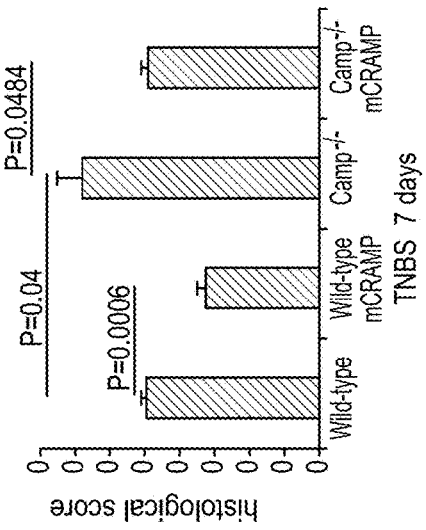
FIGS. 20A-20E shows that mCRAMP treatment significantly reduced histological damage in mice.
Figure 20E:
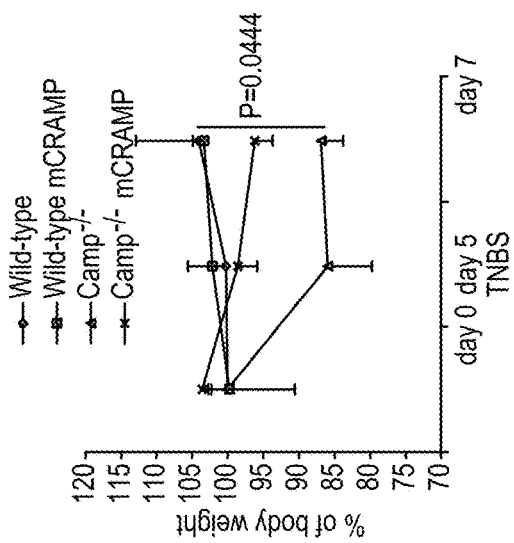
Figure 20A:
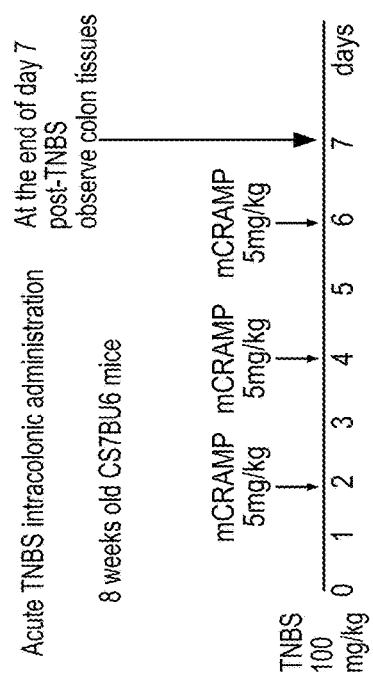
Figure 20C:
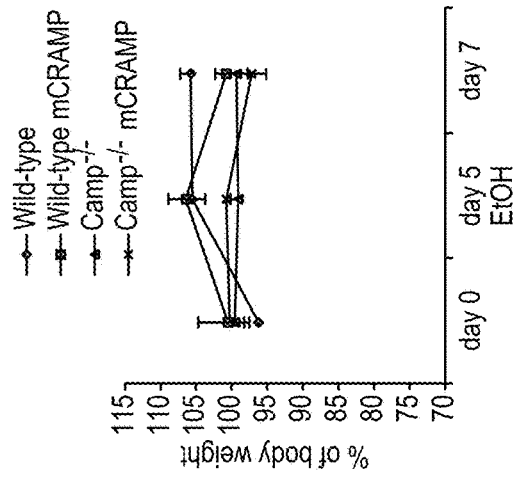
Figure 20D:
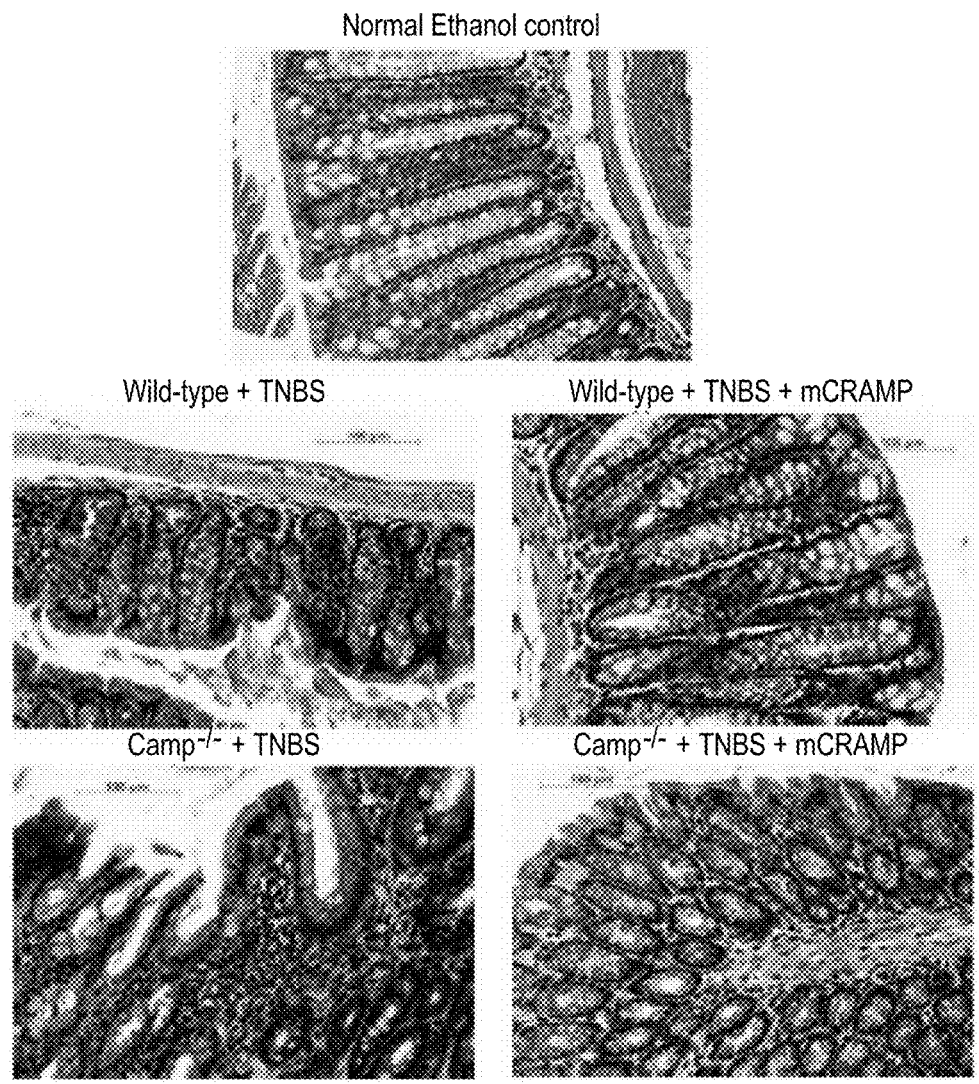

To understand the relationship of colonic LL-37 protein expression and IBD disease activity, each patient group was divided into high and low cathelicidin groups (FIG. 13A). Colonic LL-37 protein expression was not correlated to histology scores as most of biopsies taken from IBD patients were severely inflamed as reflected by high histology scores (FIG. 20A and FIG. 20B).

The UC patients with low colonic LL-37 protein levels in the biopsies had significantly higher serum C-reactive protein levels than those with high colonic LL-37 protein levels (FIG. 13B). The CD patients with low colonic LL-37 protein levels in the biopsies had significantly higher erythrocyte sedimentation rate than those with high colonic LL-37 protein levels (FIG. 13C). Thus, colonic endogenous cathelicidin protein level can indicate disease activity of IBD patients.

Example 3. Plasma Cathelicidin Levels in UC Patients are Reduced

Figures 14A, 14B, 14C:
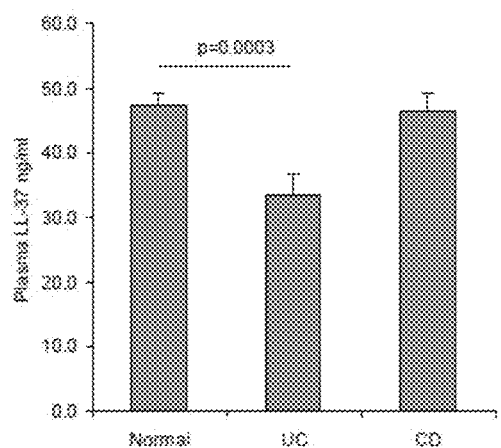
FIGS. 14A-14C show that plasma cathelicidin levels in UC patients are decreased.

The plasma samples of 40 normal, 27 UC and 30 CD patients were analyzed. Inclusion and exclusion criteria as well as baseline characteristics are shown in FIG. 14A and FIG. 14B. The plasma cathelicidin levels of UC, but not CD, patients were significantly decreased (FIG. 14C).

Figure 15C:
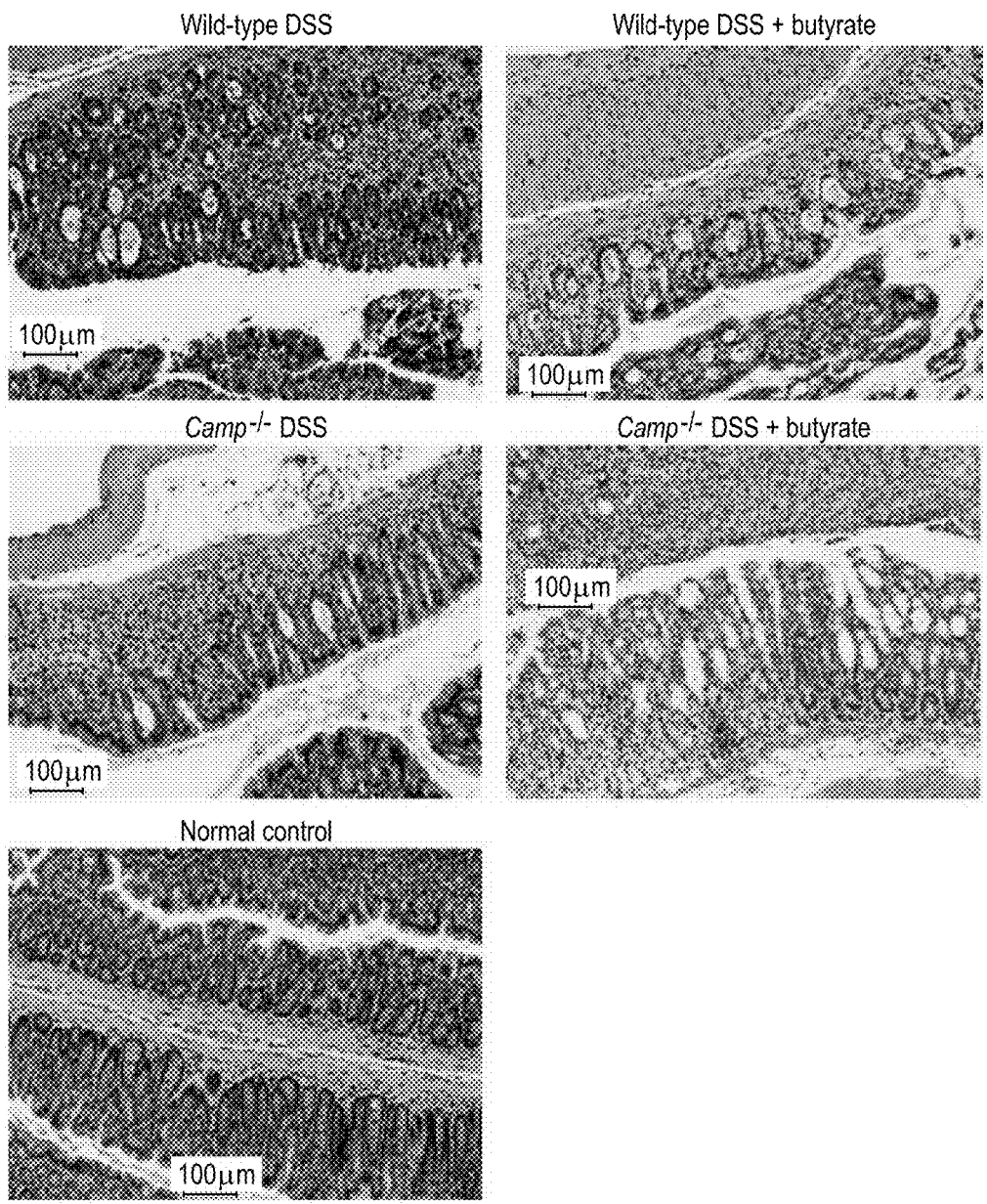

Example 4. Sodium Butyrate Ameliorates Colitis in Mice Via Induced Endogenous Cathelicidin Expression To investigate the role of endogenous cathelicidin induction in the amelioration of acute colitis, mCRAMP deficient (Camp$^{-/-}$) and wild-type mice were administered with DSS and/or sodium butyrate as illustrated in FIG. 15A. DSS colitis led to significant tissue damages (FIG. 15C) with body weight loss (FIG. 15B) and increased histology score (FIG. 15C). Camp$^{-/-}$ mice had significantly worse colitis than wild-type mice when exposed to DSS (FIG. 15C and FIG. 15D). It was found that intraperitoneal sodium butyrate administration led to significant decrease of histology score in wild-type but not Camp$^{-/-}$ deficient mice (FIG. 15C).

Figure 16A:
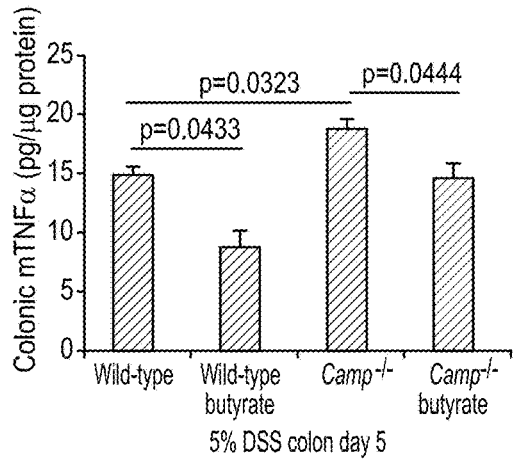
FIGS. 16A-16F show sodium butyrate inhibited colonic TNFα expression but not colonic microflora load.
Figure 16B:
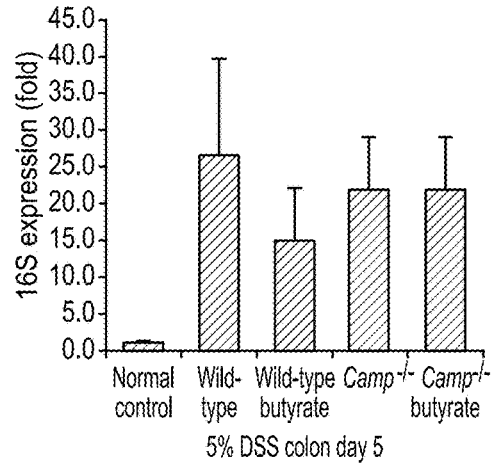
Figure 16C:
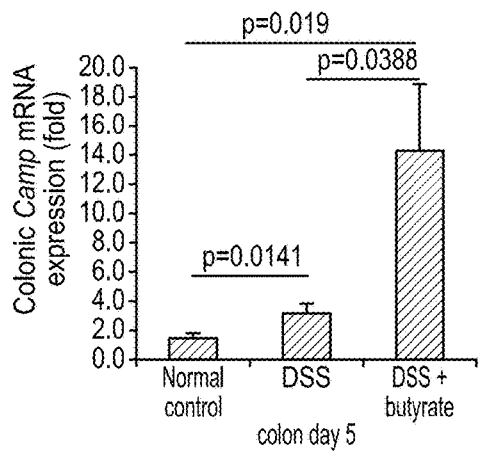
Figure 16D:
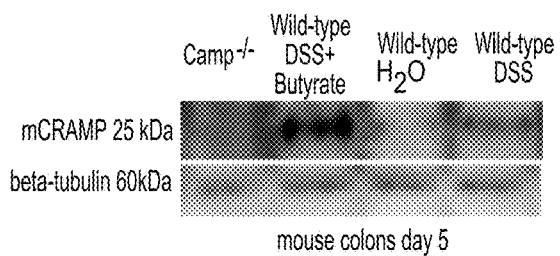
Figure 16E:
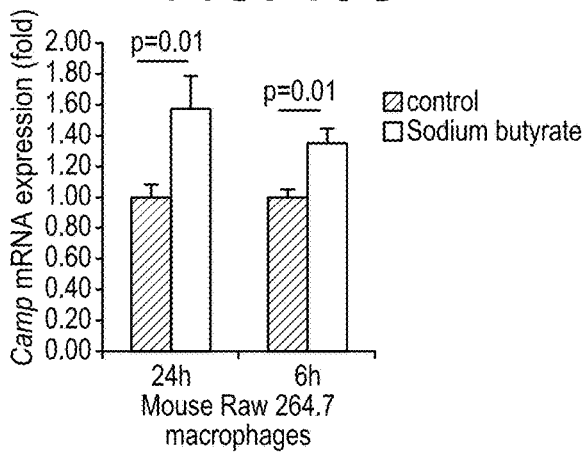
Figure 16F:
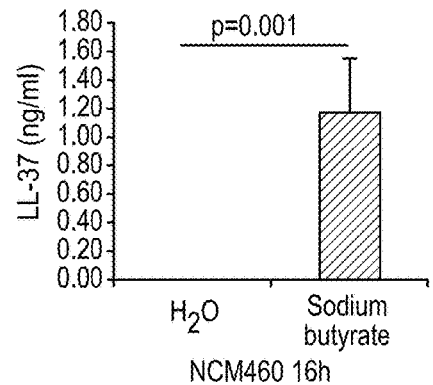

Also sodium butyrate administration caused greater decrease of colonic TNFα levels in wild-type mice (40% reduction) than Camp$^{-/-}$ mice (21% reduction) (FIG. 16A). This indicates that the anti-inflammatory effect of sodium butyrate is at least partially dependent on endogenous cathelicidin induction. However, sodium butyrate did not cause significant change of colonic microflora load as reflected by 16S expression (FIG. 16B). Sodium butyrate administration significantly induced colonic Camp mRNA expression and protein expression in mice (FIG. 16C and FIG. 16D). Sodium butyrate could also induce cathelicidin mRNA in mouse Raw264.7 macrophages and human LL-37 in NCM460 cells (FIG. 16E and FIG. 16F).

Figure 19A:
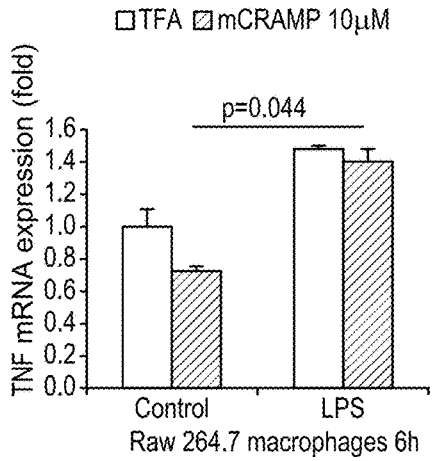
FIGS. 19A-19E show that LPS induced TNFα expression was not affected by IGF-1R inhibition.
Figure 19B:
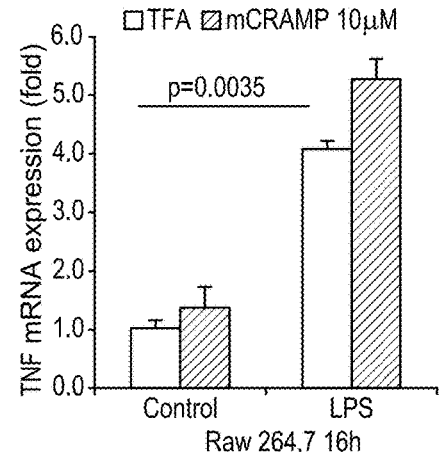
Figure 19C:
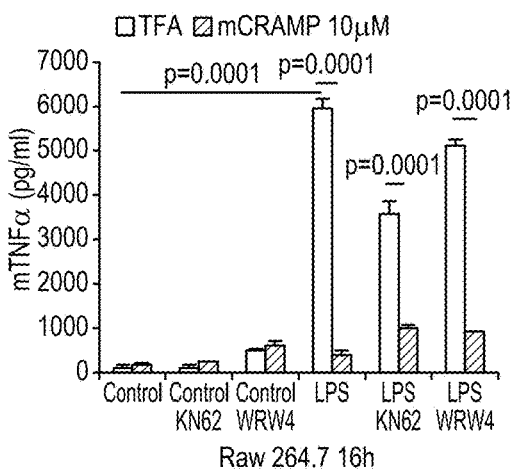

Example 5. Cathelicidin Modulates LPS Induced TNFα Expression Via Akt Dependent Pathway To identify the anti-inflammatory mechanism of cathelicidin, human PBMCs and mouse macrophages to were exposed to PAMP signals (LPS and E. coli DNA) in the presence of cathelicidin LL-37 or mCRAMP (1-10 µM). Cathelicidin significantly inhibited LPS, but not bacterial DNA, induced TNFα protein expression in PBMCs (FIG. 17A and FIG. 17C). Cathelicidin did not affect LPS induced TNFα mRNA expression in Raw264.7 macrophages (FIG. 19A and FIG. 19B). Similar anti-inflammatory effects also existed in fresh human colonic biopsies against LPS (FIG. 17B). However, cathelicidin did not possess anti-inflammatory effects against flagellin in mouse Raw264.7 macrophages (FIG. 17D). The anti-inflammatory effect of cathelicidin against LPS was reversed by pretreatment of G-protein coupled receptor inhibitor pertussis toxin but not formyl peptide receptor antagonist WRW4 or purinoceptor 7 antagonist KN62. This indicates that cathelicidin mediates its anti-inflammatory effects via G protein coupled receptor but not formyl peptide receptor (FPR2) or purinoceptor 7 (P2RX7) (FIG. 17E and FIG. 19C).

Figure 18A:
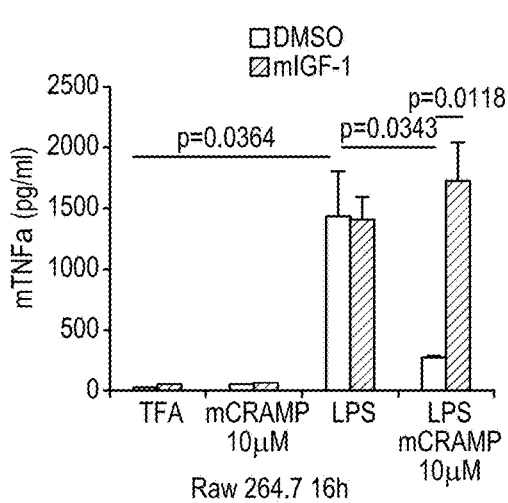
FIGS. 18A-18F shows that cathelicidin inhibited LPS induced TNFα expression in macrophages was Akt dependent.
Figure 18B:
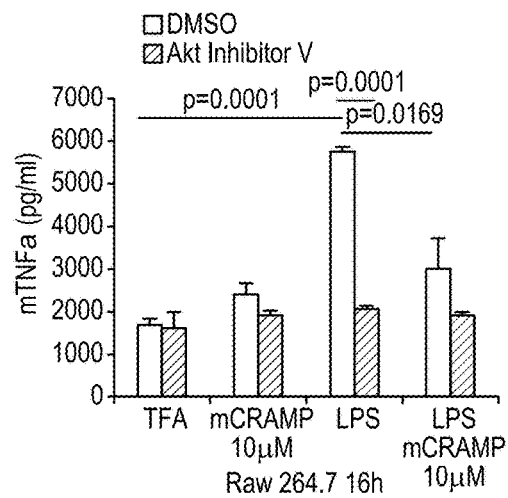
Figure 18C:
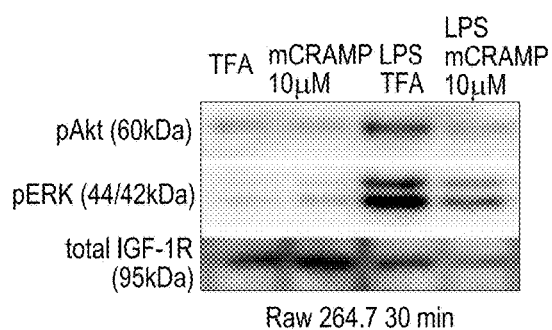
Figure 18D:
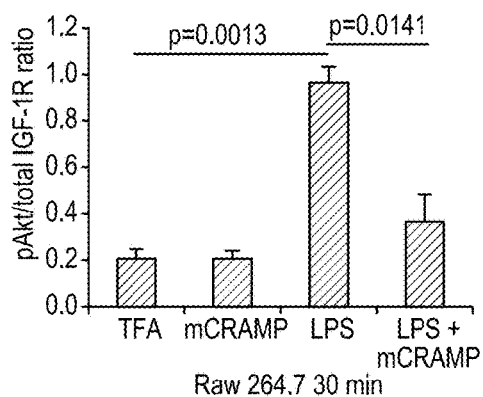
Figure 18E:
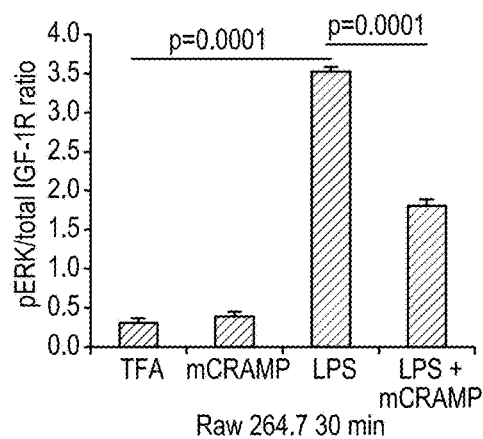
Figure 19D:
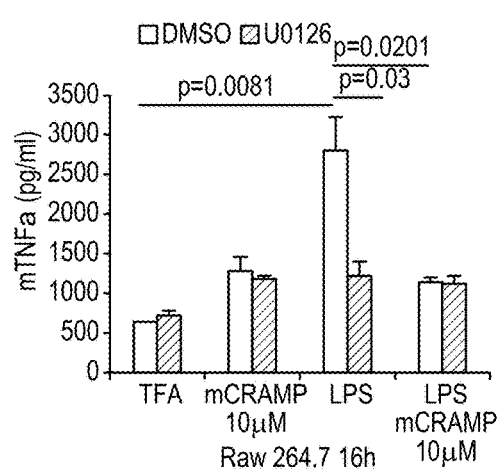

Consistent with previous reports (Pinheiro da Silva F, Gallo R L, Nizet V. Differing effects of exogenous or endogenous cathelicidin on macrophage toll-like receptor signaling. Immunol Cell Biol. 2009; 87(6):496-500), the data presented herein shows that cathelicidin reduced LPS mediated MAP kinase phosphorylation in macrophages (FIG. 19D). LPS induced TNFα expression was inhibited by Akt inhibitor V Triciribine (FIG. 18B) and MAP kinase inhibitor U0126 (FIG. 19D). This suggested that LPS induced TNFα expression via Akt and ERK. Mouse cathelicidin suppressed LPS induced Akt and ERK phosphorylation (FIG. 18C, FIG. 18D, and FIG. 18E) while addition of mouse IGF-1 reversed cathelicidin mediated inhibition of LPS induced TNFα expression in Raw264.7 macrophages (FIG. 18A). This indicates that cathelicidin modulates LPS induced TNFα expression by modulating Akt activity. This suggests that cathelicidin inhibits TNFα expression via Akt dependent mechanism in macrophages.

Example 6

The anti-inflammatory effects of cathelicidin in immune cells as a part of innate immunity had been previously reported (Koon H W, Shih D Q, Chen J, Bakirtzi K, Hing T C, Law I, et al. Cathelicidin signaling via the Toll-like receptor protects against colitis in mice. Gastroenterology. 2011; 141(5):1852-63 e1-3; Di Nardo A, Braff M H, Taylor K R, Na C, Granstein R D, McInturff J E, et al. Cathelicidin antimicrobial peptides block dendritic cell TLR4 activation and allergic contact sensitization. J Immunol. 2007; 178(3): 1829-34; Nagaoka I, Hirota S, Niyonsaba F, Hirata M, Adachi Y, Tamura H, et al. Cathelicidin family of antibacterial peptides CAP18 and CAP11 inhibit the expression of TNF-alpha by blocking the binding of LPS to CD14(+) cells. J Immunol. 2001; 167(6):3329-38).

Several antimicrobial peptides including lactoferrin, hepcidin and defensin had been found to be correlated to IBD disease activity (Ho S, Pothoulakis C, Koon H W. Antimicrobial peptides and colitis. Curr Pharm Des. 2012; 19(1): 40-7). Although increased colonic mRNA expression of cathelicidin in UC patients had been reported previously (Schauber J, Rieger D, Weiler F, Wehkamp J, Eck M, Fellermann K, et al. Heterogeneous expression of human cathelicidin hCAP18/LL-37 in inflammatory bowel diseases. Eur J Gastroenterol Hepatol. 2006; 18(6):615-21), the data described herein does not show a significant increase of colonic cathelicidin protein expression in IBD patients (FIG. 12D), compared to normal control group. Instead, there is a large variation of colonic cathelicidin levels among IBD patients as detected by ELISA and immunohistochemistry (FIG. 12D and FIG. 12E). The large variation of colonic cathelicidin expression may be influenced by IBD disease activity of patients individually. The data shows that colonic cathelicidin protein level is correlated to common clinical IBD disease markers such as CRP and ESR (FIG. 13). This novel finding is supported by another report as low plasma LL-37 levels also predicted increased infection and mortality in renal hemodialysis patients (Gombart A F, Bhan I, Borregaard N, Tamez H, Camargo C A, Jr., Koeffler H P, et al. Low plasma level of cathelicidin antimicrobial peptide (hCAP18) predicts increased infectious disease mortality in patients undergoing hemodialysis. Clin Infect Dis. 2009; 48(4):418-24). Since there is no absolute correlation between colonic cathelicidin mRNA and protein expression (FIG. 12C and FIG. 12D), colonic cathelicidin mRNA expression is not correlated to IBD disease marker (CRP or ESR) levels (data not shown).

Accordingly, the endogenous cathelicidin can modulate colitis development. The data herein (FIG. 15) and previous reports both indicated that mCRAMP deficient (Camp$^{-/-}$) mice developed more severe DSS mediated colitis than wild-type mice (Koon H W, Shih D Q, Chen J, Bakirtzi K, Hing T C, Law I, et al. Cathelicidin signaling via the Toll-like receptor protects against colitis in mice. Gastroenterology. 2011; 141(5):1852-63 e1-3). Along the same line, it is also possible to induce endogenous cathelicidin to achieve therapeutic effects against colonic inflammation. Sodium butyrate is short chain fatty acid and bacterial metabolite of gut microflora mediated carbohydrate fermentation that had been shown to reduce clinical UC disease activity in humans and DSS mediated colitis in animal models (Vernia P, Monteleone G, Grandinetti G, Villotti G, Di Giulio E, Frieri G, et al. Combined oral sodium butyrate and mesalazine treatment compared to oral mesalazine alone in ulcerative colitis: randomized, double-blind, placebo-controlled pilot study. Dig Dis Sci. 2000; 45(5):976-81; Vieira E L, Leonel A J, Sad A P, Beltrao N R, Costa T F, Ferreira T M, et al. Oral administration of sodium butyrate attenuates inflammation and mucosal lesion in experimental acute ulcerative colitis. J Nutr Biochem. 2011; 23(5):430-6). The data herein is novel evidence that endogenous cathelicidin is partially involved in the anti-inflammatory effects of sodium butyrate in DSS colitis in mice (FIG. 15 and FIG. 16). Intraperitoneal sodium butyrate administration induced colonic cathelicidin mRNA and protein expression (FIG. 16). Induction of endogenous cathelicidin by sodium butyrate may be a potential therapeutic approach against IBD.

As shown in a previous report, intracolonic exogenous cathelicidin mCRAMP peptide administration ameliorates DSS mediated colitis (Tai E K, Wu W K, Wong H P, Lam E K, Yu L, Cho C H. A new role for cathelicidin in ulcerative colitis in mice. Exp Biol Med (Maywood). 2007; 232(6): 799-808). It is demonstrated herein that the same approach significantly ameliorated TNBS mediated colitis (FIG. 20 and FIG. 21). Similar to DSS model, Camp$^{-/-}$ mice developed more severe colitis than wild-type mice when exposed to TNBS. Camp$^{-/-}$ mice had significantly higher histology score and colonic TNFα levels than wild-type mice that were reduced by exogenous cathelicidin (FIG. 20 and FIG. 21). Colonic cathelicidin mRNA expression was transiently increased on day 3 but not day 7 of TNBS mediated colitis (FIG. 21B and FIG. 21C) while colonic cathelicidin protein level was still significantly increased on day 5 of DSS mediated colitis (Koon H W, Shih D Q, Chen J, Bakirtzi K, Hing T C, Law I, et al. Cathelicidin signaling via the Toll-like receptor protects against colitis in mice. Gastroenterology. 2011; 141(5):1852-63 e1-3).

On the other hand, the major difference of therapeutic mechanism of exogenous cathelicidin and endogenous cathelicidin is the change of microflora load. It was found that there was no significant difference of colonic 16S expression in wild-type and Camp$^{-/-}$ mice of both DSS and TNBS colitis models (FIG. 16B and FIG. 22D). Also, sodium butyrate administration did not alter colonic 16S expression in DSS exposed mice (FIG. 16B). This data indicated that endogenous cathelicidin exerts anti-inflammatory effects in colitis without involvement of anti-microbial effects. In contrast, exogenous cathelicidin significantly reduced microflora load (16S ribosome) in both TNBS model (FIG. 22D) and DSS model Tai E K, Wu W K, Wong H P, Lam E K, Yu L, Cho C H. A new role for cathelicidin in ulcerative colitis in mice. Exp Biol Med (Maywood). 2007; 232(6):799-808. As antibiotics therapy is able to induce remission in IBD (Khan K J, Ullman T A, Ford A C, Abreu M T, Abadir A, Marshall J K, et al. Antibiotic therapy in inflammatory bowel disease: a systematic review and meta-analysis. Am J Gastroenterol. 2011; 106(4):661-73), the antimicrobial effects may be involved in the exogenous cathelicidin mediated amelioration of colitis.

Figure 22A:
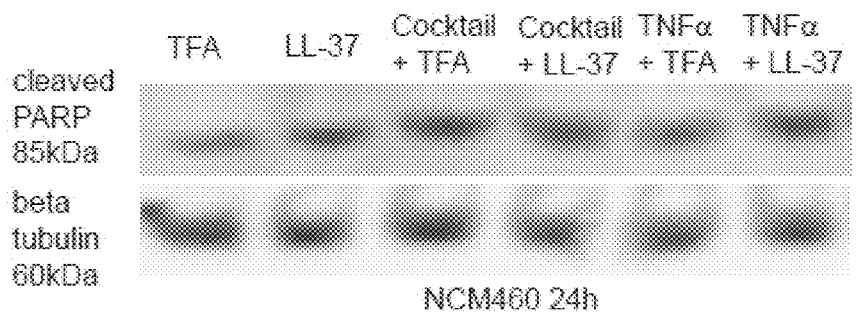
FIGS. 22A and 22B show that cathelicidin reduces colonic apoptosis in mice with acute colitis. NCM460 cells were treated with proinflammatory cytokines cocktail or TNFα (10 ng/ml) with or without LL-37 (10 μM) for 24 hours. Apoptosis signaling molecule cleaved PARP was determined by Western blot and quantification. LL-37 did not affect apoptosis in NCM460 colonocytes in the presence of proinflammatory cytokine cocktail or TNFα. All experiments are representative of 3 independent experiments.
Figure 22B:
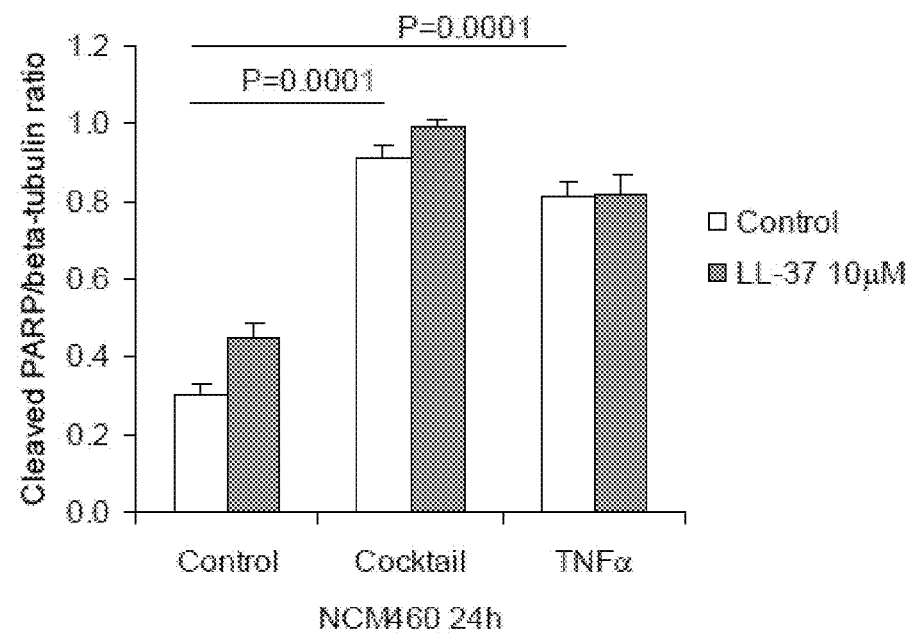

LL-37 (10 µM) failed to reverse PARP cleavage (apoptosis) induced by TNFα or proinflammatory cytokine cocktail in NCM460 colonocytes (FIG. 22A and FIG. 22B). Cathelicidin does not alter cell viability and also cannot reverse C. difficile toxin A mediated loss of cell viability in NCM460 colonocytes, PBMCs and Raw264.7 macrophages (Hing T C, Ho S, Shih D Q, Ichikawa R, Cheng M, Chen J, et al. The antimicrobial peptide cathelicidin modulates Clostridium difficile-associated colitis and toxin A-mediated enteritis in mice. Gut. 2012). Thus, cathelicidin does not mediate direct anti-apoptotic or wound healing effects during colitis.

To further characterize the anti-inflammatory mechanisms of cathelicidin, the inhibitory effects of cathelicidin in the expression of TNFα in PBMCs and macrophages in vivo and in vitro were studied. TNFα is an important therapeutic target of IBD as Infliximab® is efficacious to treat IBD patients (Peyrin-Biroulet L. Anti-TNF therapy in inflammatory bowel diseases: a huge review. Minerva Gastroenterol Dietol. 2010; 56(2):233-43). Inhibition of TNFα expression in immune cells may help ameliorate colitis by reducing the augmentation and/or perpetuation of inflammatory cascade such as tissue damage and apoptosis (Wang Q Y, Sun A M, Song J, Chen Y, Wang J D, Li C G. Cytokine tumor necrosis factor alpha induces intestinal epithelial barrier dysfunction. Cytokine 2012; 58(2):226-30). On the other hand, our bone marrow transplantation experiments demonstrated that endogenous cathelicidin from bone-marrow derived cells including monocytes are responsible for modulating DSS mediated colitis (Koon H W, Shih D Q, Chen J, Bakirtzi K, Hing T C, Law I, et al. Cathelicidin signaling via the Toll-like receptor protects against colitis in mice. Gastroenterology. 2011; 141(5):1852-63 e1-3). PBMCs and macrophages are thus important target cells of cathelicidin mediated anti-inflammatory effects in colitis.

Moreover, this is the first time in literature to find that the plasma cathelicidin levels of UC, but not CD, patients are significantly reduced (FIG. 14C). Although we don't fully understand the mechanism and the cause of this decrease, we speculate that cathelicidin expressing immune cells may concentrate in the inflamed colons as there is increased cathelicidin mRNA expression in UC colonic tissues (FIG. 12C). This may deplete the cathelicidin secreting cells and then subsequently reduce the circulating cathelicidin levels.

Figure 18F:
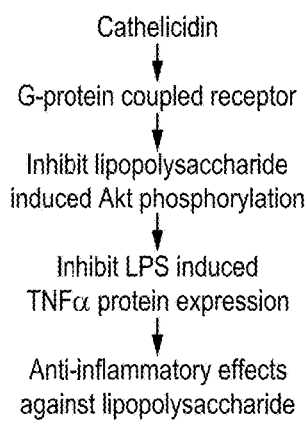
Figure 19E:
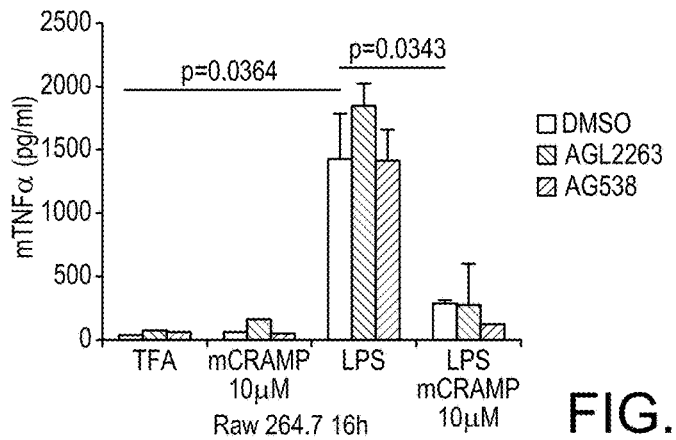

A previous report showed that cathelicidin can bind to LPS and neutralize its toxicity extracellularly (Scott A, Weldon S, Buchanan P J, Schock B, Ernst R K, McAuley D F, et al. Evaluation of the ability of LL-37 to neutralise LPS in vitro and ex vivo. PLoS One. 2011; 6(10):e26525). The data disclosed herein shows the anti-inflammatory effects of cathelicidin was GPCR dependent (FIG. 17F), suggesting intracellular mechanism. Two putative cathelicidin receptors (FPR2 and P2X7) and insulin like growth factor receptor 1 (IGF-1R) were not involved in the anti-inflammatory effects of cathelicidin in the macrophages (FIG. 19C and FIG. 19E). Instead, GPCR mediated cathelicidin modulated inhibition of Akt phosphorylation and subsequent TNFα expression (FIG. 18).

In summary, the inventions disclosed herein provide novel evidence of the value of cathelicidin as a novel diagnostic IBD marker. Sodium butyrate induced cathelicidin expression may be a novel therapeutic approach against colitis. Cathelicidin suppressed LPS induced inflammatory responses via Akt dependent mechanism (FIG. 18F).

Example 7

Figure 23:
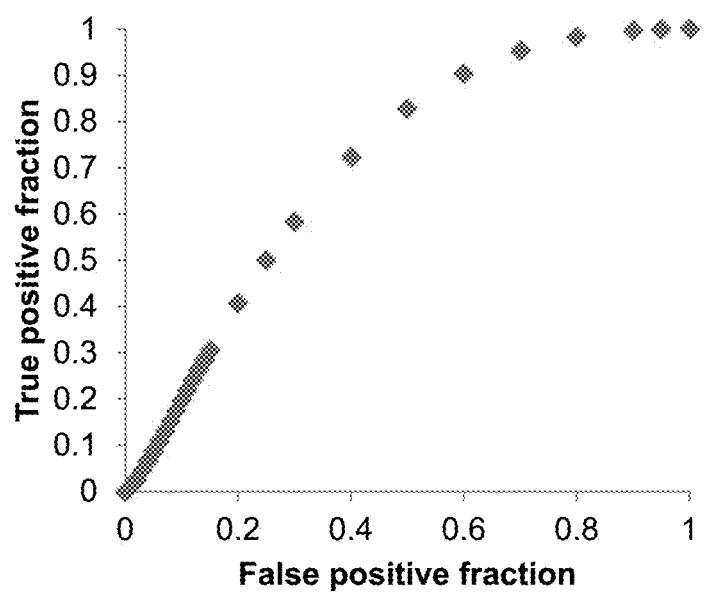
FIG. 23 is a receiver operating characteristics (ROC) curve, showing that low serum LL-37 levels (below 40 ng/ml) is indicative of ulcerative colitis (UC) activity, as reflect by partial Mayo score. The ROC curve area is 0.708, indicating that there is a 71% chance of UC patients with moderate or active UC (partial Mayo score of 5-8) having a lower serum LL-37 level than those who are not.
Figure 24:
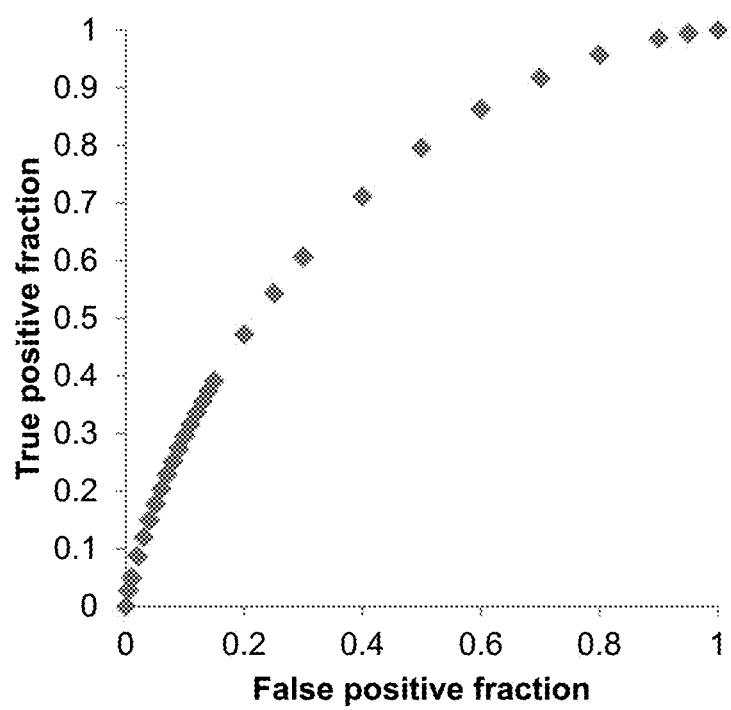
FIG. 24 is a receiver operating characteristics (ROC) curve, showing that high serum LL-37 levels (below 40 ng/ml) is indicative of ulcerative colitis (UC) in remission, as reflect by partial Mayo score. The ROC curve area is 0.714, indicating that there is a 71% chance of UC patients with UC in remission (Partial Mayo score of 0-2) having a higher serum LL-37 level than those who are not.

The use cathelicidin protein expression levels as a diagnostic marker for ulcerative colitis (UC) activity was assessed. Briefly, inflammatory bowel disease samples were obtained from the UCLA Center for Inflammatory Bowel Diseases. Serum LL-37 expression levels were measured by LL-37 ELISA and CRP levels were downloaded from the UCLA CareConnect Epic Clinical Data System. Mayo scores for UC were determined using standard techniques (see, e.g., Lewis et al. *Inflamm Bowel Dis.* 14(12): 1660-1666 (2008). Receiver Operating Characteristics (ROC) curves were determined based on the LL-37 protein expression levels obtained. FIG. 23 is a receiver operating characteristics (ROC) curve, showing that low serum LL-37 levels (below 40 ng/ml) is indicative of ulcerative colitis (UC) activity, as reflect by partial Mayo score. The ROC curve area is 0.708, indicating that there is a 71% chance of UC patients with moderate or active UC (Partial Mayo score of 5-8) having a lower serum LL-37 level than those who are not. FIG. 24 is a ROC curve, showing that high serum LL-37 levels (below 40 ng/ml) is indicative of ulcerative colitis (UC) in remission, as reflect by partial Mayo score. The ROC curve area is 0.714, indicating that there is a 71% chance of UC patients with UC in remission (Partial Mayo score of 0-2) having a higher serum LL-37 level than those that do not. As a comparison, fitted ROC curve area=0.71-0.80 for CRP to reflect UC disease activity (see J Chron's Colitis 5(5):423-9 doi: 10.1016/j.crohns/2011.05.003. Epub 2011 Jun. 2. This study demonstrates that LL-37 is as accurate as CRP in reflecting UC activity.

Example 8

Figure 25:
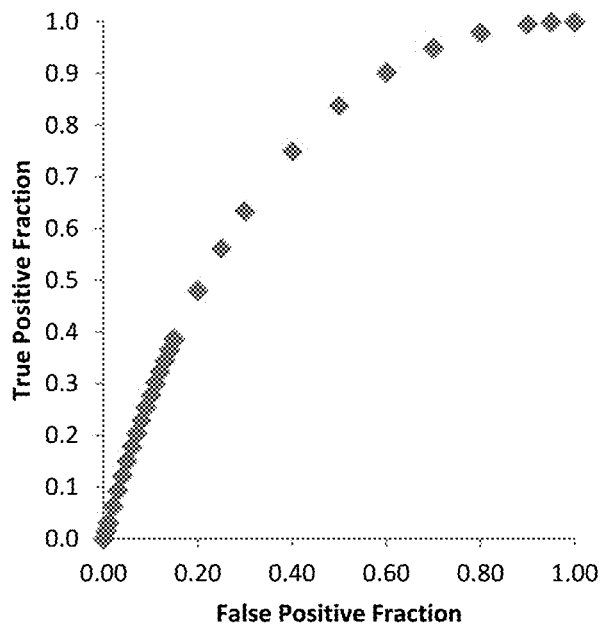
FIG. 25 is a receiver operating characteristics (ROC) curve, showing that serum LL-37 levels is indicative of stricture in patients having Crohn's disease (CD). The ROC curve area is 0.733, indicating that there is a 73% chance of strictured CD patients having a lower serum LL-37 level than non-strictured CD patients.

The use of serum LL-37 as a diagnostic marker for stricture associate with Crohn's disease was also assessed. Presence of stricture was written in progress note of each patient and this information was downloaded from UCLA CareConnect Epic Clinical Data System. FIG. 25 is a receiver operating characteristics (ROC) curve, showing that serum LL-37 levels is indicative of stricture in patients having Crohn's disease (CD). The ROC curve area is 0.733, indicating that there is a 73% chance of strictured CD patients having a lower serum LL-37 level than non-strictured CD patients. This study shows that LL-37 is a biomarker for stricture associated with CD patients.

Example 9

Figure 26A:
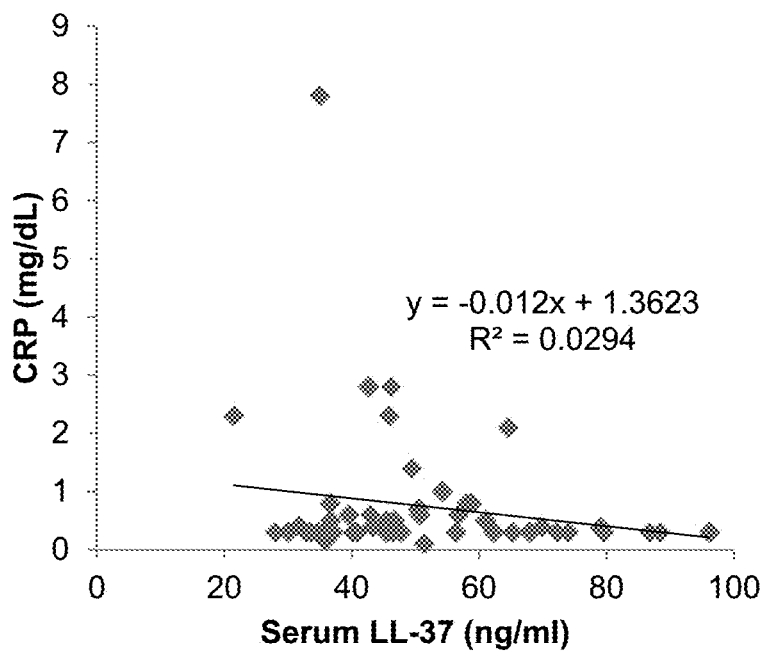
FIGS. 26 A and B are graphs showing the correlation of serum LL-37 and serum CRP in ulcerative colitis patients. As shown in these graphs, high serum LL-37 levels correlated with low serum CRP levels among these UC patients.
Figure 26B:
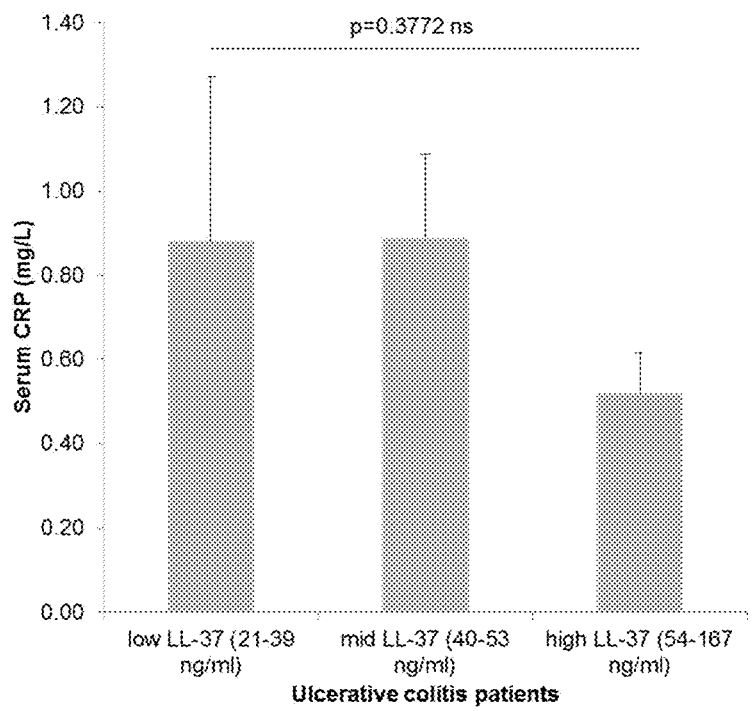
Figure 27:
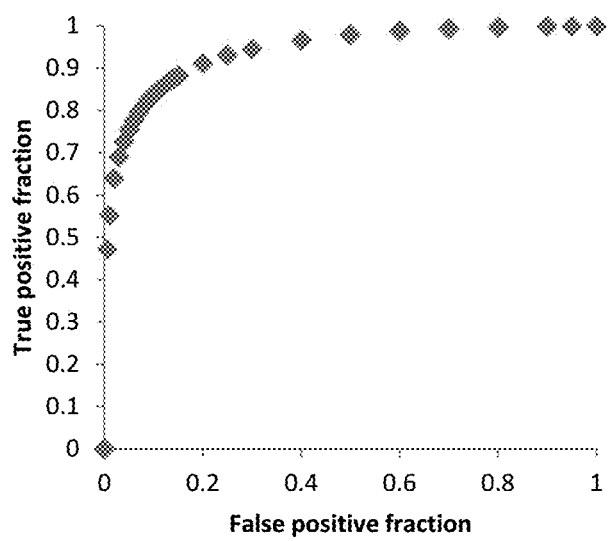
FIG. 27 is a receiver operating characteristics (ROC) curve, showing that low serum LL-37 levels (below 54 ng/ml) and high serum CRP levels (above 2 mg/L) is indicative of moderate or active ulcerative colitis (UC), as reflected by Mayo score (5-8). The ROC curve area is 0.942, indicating that there is a 94% chance of UC patients with moderate/active UC (Partial Mayo score of 5-8) having a lower serum LL-37 level and a higher serum CRP level than those who are not.
Figure 28:
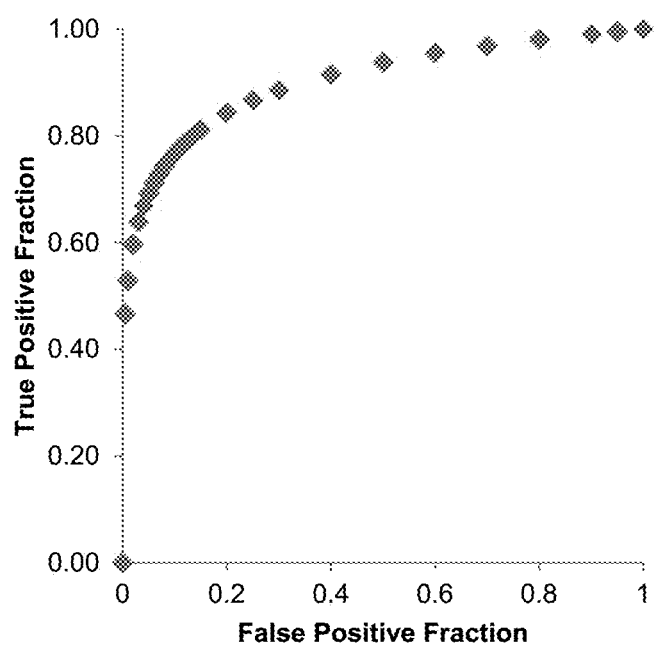
FIG. 28 is a receiver operating characteristics (ROC) curve, showing that high serum LL-37 levels (above 54 ng/ml) and low serum CRP levels (below 2 mg/L) is indicative of ulcerative colitis (UC) in remission, as reflected by Mayo score (0-2). The ROC curve area is 0.903, indicating that there is a 90% chance of UC patients with UC in remission (Partial Mayo score of 0-2) having a higher LL-37 level and a lower CRP level than those who do not.
Figure 29A:
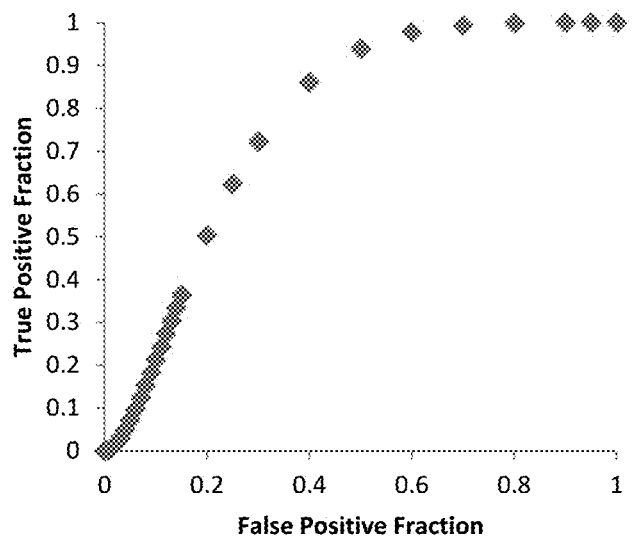
Figure 29B:
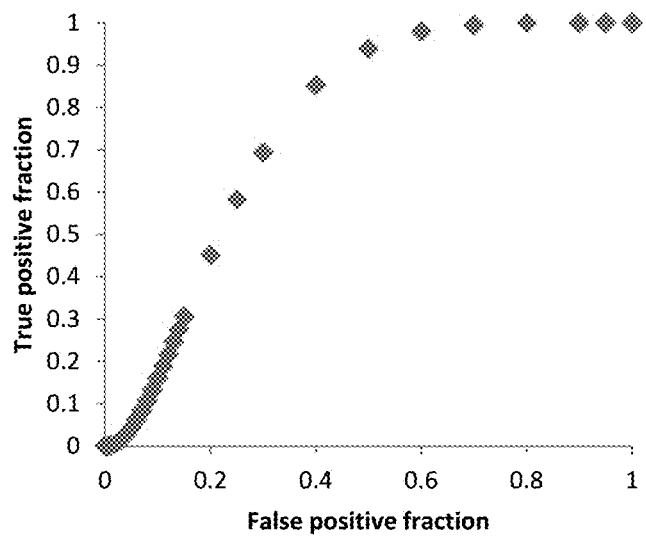

The use of serum LL-37 and CRP protein expression levels as diagnostic markers for UC activity was assessed. FIGS. 26 A and B are graphs showing the correlation of serum LL-37 and serum CRP in ulcerative colitis patients. As shown in these graphs, high serum LL-37 levels correlated with low serum CRP levels among these UC patients. FIG. 27 is a receiver operating characteristics (ROC) curve, showing that low serum LL-37 levels (below 54 ng/ml) and high serum CRP levels (above 2 mg/L) is indicative of moderate or active ulcerative colitis (UC), as reflected by Mayo score (5-8). The ROC curve area is 0.942, indicating that there is a 94% chance of UC patients with moderate/active UC (Partial Mayo score of 5-8) having a lower serum LL-37 level and a higher serum CRP level than those who are not. As shown in FIG. 28, high serum LL-37 levels (above 54 ng/ml) and low serum CRP levels (below 2 mg/L) is indicative of ulcerative colitis (UC) in remission, as reflected by Mayo score (0-2). The ROC curve area is 0.903, indicating that there is a 90% chance of UC patients with UC in remission (Partial Mayo score of 0-2) having a higher LL-37 level and a lower CRP level than those who do not. FIGS. 29A-C are receiver operating characteristics (ROC) curves showing the ability of CRP expression levels alone to diagnose moderate/active ulcerative colitis (UC) (FIG. 29 A, ROC curve area=0.771) and UC remission (FIG. 29B, ROC curve area=0.712). Fitted ROC curve area for LL-37 alone is 0.708 with respect to moderate/active ulcerative colitis diagnosis and 0.714 for UC remission diagnosis (data not shown). Taken altogether, this data demonstrates that the combination of LL-37 and CRP together is more accurate than either LL-37 or CRP alone in reflecting UC activity.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for detecting an active inflammatory bowel disease in a patient, the method comprising detecting cathelicidin protein levels and C-reactive protein (CRP) levels in a blood sample from the patient, wherein low levels of cathelicidin protein and high CRP levels are indicative of an active inflammatory bowel disease; and
administering to the patient a pharmaceutical composition to increase the patient's cathelicidin protein levels when the serum cathelicidin protein level is 60 ng/ml or below and the serum CRP level is 1 mg/L or above.

2. The method of claim 1, wherein the cathelicidin protein levels are LL-37 peptide levels.

3. The method of claim 1, wherein the inflammatory bowel disease is ulcerative colitis (UC).

4. The method of claim 1, wherein the patient is administered treatment for ulcerative colitis if the patient has a serum cathelicidin protein level of 55 ng/ml or below and a serum CRP level of 2 mg/L or above.

5. The method of claim 1 wherein the cathelicidin protein levels and CRP protein levels are detected using a cathelicidin binding probe and a CRP binding probe.

6. The method of claim 5, wherein the cathelicidin binding probe is an antibody that binds cathelicidin and the CRP binding probe is an antibody that binds CRP.

7. The method of claim 5 wherein the cathelicidin binding probe and the CRP binding probe are attached to a solid support.

8. The method of claim 1, wherein the cathelicidin and CRP protein levels are detected by ELISA.

9. The method of claim 1 wherein the cathelicidin protein levels are detected by assay selected from the group consisting of FACS, Western blot, and immunohistochemistry.

10. The method of claim 1 wherein the patient is a human.

11. The method of claim 1, wherein the pharmaceutical composition comprises a cathelicidin polypeptide.

12. The method of claim 11, wherein the cathelicidin polypeptide is administered at a dose of about 0.1-100 mg/kg body weight.

13. The method of claim 1, wherein the wherein the patient is administered treatment for Crohn's disease if the patient has a serum cathelicidin protein level of 45 ng/ml or below.

* * * * *